US011172851B2

(12) United States Patent
Pushpala et al.

(10) Patent No.: US 11,172,851 B2
(45) Date of Patent: *Nov. 16, 2021

(54) SYSTEM FOR MONITORING BODY CHEMISTRY

(71) Applicant: One Drop Biosensor Technologies, LLC, New York, NY (US)

(72) Inventors: Ashwin Pushpala, San Francisco, CA (US); Dominic Pitera, San Francisco, CA (US); Matthew Chapman, Oakland, CA (US); Michael Gifford, San Francisco, CA (US)

(73) Assignee: One Drop Biosensor Technologies, LLC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/182,097

(22) Filed: Feb. 22, 2021

(65) Prior Publication Data
US 2021/0236057 A1    Aug. 5, 2021

Related U.S. Application Data

(63) Continuation of application No. 16/791,518, filed on Feb. 14, 2020, which is a continuation of application
(Continued)

(51) Int. Cl.
*A61B 5/1473* (2006.01)
*A61B 5/145* (2006.01)
(Continued)

(52) U.S. Cl.
CPC .......... *A61B 5/1451* (2013.01); *A61B 5/0022* (2013.01); *A61B 5/0537* (2013.01);
(Continued)

(58) Field of Classification Search
CPC .. A61B 5/685; A61B 5/1473; A61B 2560/063
See application file for complete search history.

(56) References Cited

U.S. PATENT DOCUMENTS 4,953,552 A    9/1990    DeMarzo
5,215,088 A    6/1993    Normann et al.
(Continued)

FOREIGN PATENT DOCUMENTS

CN    1735375    2/2006
CN    102469941    5/2012
(Continued)

OTHER PUBLICATIONS

Adhikari, Basudam, et al., "Polymers in sensor applications", Prog. Polym. Sci. vol. 29, pp. 699-766, Jan. 1, 2004.
(Continued)

*Primary Examiner* — Meredith Weare
(74) *Attorney, Agent, or Firm* — Perkins Coie LLP

(57) ABSTRACT

A system and method for monitoring body chemistry of a user, the system comprising: a housing supporting: a microsensor comprising a first and second working electrode, a reference electrode, and a counter electrode, and configured to access interstitial fluid of the user, and an electronics subsystem comprising a signal conditioning module that receives a signal stream, from the microsensor, wherein the electronics subsystem is configured to detect an impedance signal derived from two of the first working electrode, the second working electrode, the reference electrode, and the counter electrode; and a processing subsystem comprising: a first module configured to generate an analysis indicative of an analyte parameter of the user and derived from the signal stream and the impedance signal, and a second module configured to transmit information derived
(Continued)

from the analysis to the user, thereby facilitating monitoring of body chemistry of the user.

39 Claims, 31 Drawing Sheets

Related U.S. Application Data

No. 15/601,204, filed on May 22, 2017, now Pat. No. 10,595,754, which is a continuation-in-part of application No. 15/412,229, filed on Jan. 23, 2017, now abandoned, which is a continuation of application No. 14/657,973, filed on Mar. 13, 2015, now abandoned.

(60) Provisional application No. 62/025,174, filed on Jul. 16, 2014, provisional application No. 62/012,874, filed on Jun. 16, 2014, provisional application No. 61/952,594, filed on Mar. 13, 2014.

(51) Int. Cl.
*A61B 5/00* (2006.01)
*A61B 5/0538* (2021.01)
*A61B 5/0537* (2021.01)
*G16H 40/67* (2018.01)

(52) U.S. Cl.
CPC .......... *A61B 5/0538* (2013.01); *A61B 5/1473* (2013.01); *A61B 5/14532* (2013.01); *A61B 5/14546* (2013.01); *A61B 5/685* (2013.01); *A61B 5/688* (2013.01); *A61B 5/6833* (2013.01); *A61B 5/6834* (2013.01); *A61B 5/6849* (2013.01); *A61B 5/7275* (2013.01); *A61B 5/7278* (2013.01); *A61B 5/746* (2013.01); *G16H 40/67* (2018.01); *A61B 5/0002* (2013.01); *A61B 5/6885* (2013.01); *A61B 5/7285* (2013.01); *A61B 2560/063* (2013.01); *A61B 2562/028* (2013.01); *A61B 2562/0214* (2013.01); *A61B 2562/046* (2013.01); *A61B 2562/164* (2013.01)

(56) References Cited

U.S. PATENT DOCUMENTS

| | | | |
|---|---|---|---|
| 5,863,833 A | 1/1999 | Shin | |
| 5,949,739 A | 9/1999 | Reese | |
| 6,001,067 A | 12/1999 | Shults et al. | |
| 6,275,717 B1 | 8/2001 | Gross et al. | |
| 6,424,847 B1 | 7/2002 | Mastrototaro et al. | |
| 6,501,976 B1 | 12/2002 | Sohrab | |
| 6,560,471 B1 | 5/2003 | Heller et al. | |
| 6,582,573 B2 | 6/2003 | Douglas et al. | |
| 6,619,093 B2 | 9/2003 | Dawson et al. | |
| 6,690,959 B2 | 2/2004 | Thompson | |
| 6,699,667 B2 | 3/2004 | Keen | |
| 6,743,211 B1 | 6/2004 | Prausnitz et al. | |
| 6,749,792 B2 | 6/2004 | Olson | |
| 6,790,179 B2 | 9/2004 | Skover | |
| 6,793,632 B2 | 9/2004 | Sohrab | |
| 6,837,988 B2 | 1/2005 | Leong et al. | |
| 6,863,833 B1 | 3/2005 | Bloom et al. | |
| 6,875,613 B2 | 4/2005 | Shartle et al. | |
| 6,923,764 B2 | 8/2005 | Aceti et al. | |
| 7,029,444 B2 | 4/2006 | Shin et al. | |
| 7,295,867 B2 | 11/2007 | Berner et al. | |
| 7,322,960 B2 | 1/2008 | Yamamoto et al. | |
| 7,361,307 B2 | 4/2008 | Shartle et al. | |
| 7,399,585 B2 | 7/2008 | Gau | |
| 7,585,278 B2 | 9/2009 | Aceti et al. | |
| 7,591,801 B2 | 9/2009 | Brauker et al. | |
| 7,732,002 B2 | 6/2010 | Kodas et al. | |
| 7,753,888 B2 | 7/2010 | Mukerjee et al. | |
| 7,783,442 B2 | 8/2010 | Mueller et al. | |
| 7,885,697 B2 | 2/2011 | Brister et al. | |
| 7,920,906 B2 | 4/2011 | Goode et al. | |
| 7,946,984 B2 | 5/2011 | Brister et al. | |
| 7,949,382 B2 | 5/2011 | Jina | |
| 7,951,300 B2 | 5/2011 | Bhandari et al. | |
| 8,080,385 B2 | 12/2011 | Heller et al. | |
| 8,114,269 B2 | 2/2012 | Cooper et al. | |
| 8,224,414 B2 | 7/2012 | Kellogg et al. | |
| 8,280,475 B2 | 10/2012 | Brister et al. | |
| 8,280,476 B2 | 10/2012 | Jina | |
| 8,290,559 B2 | 10/2012 | Shariati et al. | |
| 8,361,037 B2 | 1/2013 | Gonnelli | |
| 8,386,027 B2 | 2/2013 | Chuang et al. | |
| 8,478,557 B2 | 7/2013 | Hayter et al. | |
| 8,565,849 B2 | 10/2013 | Kamath et al. | |
| 8,604,810 B2 | 12/2013 | Sheppard | |
| 8,608,924 B2 | 12/2013 | Cooper et al. | |
| 8,615,282 B2 | 12/2013 | Brister et al. | |
| 8,641,672 B2 | 2/2014 | Yodfat et al. | |
| 8,663,106 B2 | 3/2014 | Stivoric et al. | |
| 8,668,645 B2 | 3/2014 | Drucker et al. | |
| 8,677,188 B2 | 3/2014 | Eickmeyer et al. | |
| 8,700,114 B2 | 4/2014 | Gottlieb et al. | |
| 8,718,742 B2 | 5/2014 | Beck et al. | |
| 8,734,348 B2 | 5/2014 | Say et al. | |
| 8,744,545 B2 | 6/2014 | Say et al. | |
| 8,744,547 B2 | 6/2014 | Budiman et al. | |
| 8,774,887 B2 | 7/2014 | Say et al. | |
| 8,792,953 B2 | 7/2014 | Brister et al. | |
| 8,808,532 B2 | 8/2014 | Yang et al. | |
| 8,858,912 B2 | 10/2014 | Boyden et al. | |
| 8,865,288 B2 | 10/2014 | Bhandari et al. | |
| 8,882,670 B2 | 11/2014 | Hancock | |
| 8,886,279 B2 | 11/2014 | Tathireddy et al. | |
| 8,965,477 B2 | 2/2015 | Hoss et al. | |
| 9,011,332 B2 | 4/2015 | Heller et al. | |
| 9,044,199 B2 | 6/2015 | Brister et al. | |
| 9,055,901 B2 | 6/2015 | Brister et al. | |
| 9,192,328 B2 | 11/2015 | Brauker et al. | |
| 9,195,799 B2 | 11/2015 | Sze et al. | |
| 9,215,995 B2 | 12/2015 | Gottlieb et al. | |
| 9,220,483 B2 | 12/2015 | Frankhouser et al. | |
| 9,278,174 B2 | 3/2016 | Gray | |
| 9,357,951 B2 | 6/2016 | Simpson et al. | |
| 9,387,000 B2 | 7/2016 | Corrie et al. | |
| 9,402,544 B2 | 8/2016 | Yee et al. | |
| 9,414,777 B2 | 8/2016 | Brister et al. | |
| 9,474,478 B2 | 10/2016 | Bhavaraju et al. | |
| 9,498,159 B2 | 11/2016 | Heller et al. | |
| 9,504,411 B2 | 11/2016 | Engelhardt et al. | |
| 9,532,741 B2 | 1/2017 | Brauker et al. | |
| 9,603,557 B2 | 3/2017 | Brister et al. | |
| 9,615,851 B2 | 4/2017 | Neinast et al. | |
| 9,632,060 B2 | 4/2017 | Shah et al. | |
| 9,662,047 B2 | 5/2017 | Barman et al. | |
| 9,737,247 B2 | 8/2017 | Wang et al. | |
| 9,743,870 B2 | 8/2017 | Wang et al. | |
| 9,814,389 B2 | 11/2017 | DeHennis | |
| 9,974,471 B1 | 5/2018 | Kam et al. | |
| 10,046,114 B1 | 8/2018 | Biederman et al. | |
| 10,070,820 B2 | 9/2018 | Huang | |
| 10,136,846 B2 | 11/2018 | Wang et al. | |
| 10,238,289 B2 | 3/2019 | Hagi | |
| 10,321,858 B2 | 6/2019 | Maiz-Aguinaga et al. | |
| 10,327,678 B2 | 6/2019 | Gottlieb et al. | |
| 10,383,558 B2 | 8/2019 | Cho et al. | |
| 10,524,730 B2 | 1/2020 | Reitz et al. | |
| 10,595,754 B2 | 3/2020 | Pushpala et al. | |
| 10,667,733 B2 | 6/2020 | Simpson et al. | |
| 10,765,369 B2 | 9/2020 | Antonio et al. | |
| 10,799,158 B2 | 10/2020 | Brister et al. | |
| 10,799,159 B2 | 10/2020 | Brister et al. | |
| 10,806,384 B2 | 10/2020 | Frey et al. | |
| 10,813,577 B2 | 10/2020 | Brister et al. | |
| 10,827,954 B2 | 11/2020 | Hoss et al. | |
| 10,835,161 B2 | 11/2020 | Simpson et al. | |
| 10,874,335 B2 | 12/2020 | Cho et al. | |
| 2002/0015963 A1 | 2/2002 | Keen | |

(56) References Cited

U.S. PATENT DOCUMENTS

| | | |
|---|---|---|
| 2002/0062202 A1 | 5/2002 | Arai |
| 2002/0123048 A1 | 9/2002 | Gau |
| 2003/0100821 A1 | 5/2003 | Heller et al. |
| 2004/0060902 A1 | 4/2004 | Evans et al. |
| 2004/0260241 A1 | 12/2004 | Yamamoto et al. |
| 2005/0004438 A1 | 1/2005 | Ward et al. |
| 2005/0245839 A1 | 11/2005 | Stivoric et al. |
| 2006/0015058 A1 | 1/2006 | Kellogg et al. |
| 2006/0016700 A1 | 1/2006 | Brister et al. |
| 2006/0258929 A1 | 11/2006 | Goode et al. |
| 2006/0264716 A1 | 11/2006 | Zander |
| 2007/0032717 A1 | 2/2007 | Brister et al. |
| 2007/0179371 A1 | 8/2007 | Peyser et al. |
| 2007/0208245 A1 | 9/2007 | Brauker et al. |
| 2007/0219480 A1 | 9/2007 | Kamen et al. |
| 2008/0033254 A1 | 2/2008 | Kamath et al. |
| 2008/0058726 A1 | 3/2008 | Jina et al. |
| 2008/0114280 A1* | 5/2008 | Stafford ............... A61B 5/1468 604/19 |
| 2008/0138582 A1 | 6/2008 | Bhandari et al. |
| 2008/0154107 A1 | 6/2008 | Jina |
| 2008/0319285 A1 | 12/2008 | Hancock |
| 2009/0036794 A1 | 2/2009 | Stubhaug et al. |
| 2009/0156924 A1 | 6/2009 | Shariati et al. |
| 2009/0294307 A1 | 12/2009 | Liu et al. |
| 2009/0301994 A1 | 12/2009 | Bhandari et al. |
| 2009/0321277 A1 | 12/2009 | Heller et al. |
| 2010/0010601 A1 | 1/2010 | Negi et al. |
| 2010/0016687 A1 | 1/2010 | Brauker et al. |
| 2010/0030045 A1 | 2/2010 | Gottlieb et al. |
| 2010/0075353 A1 | 3/2010 | Heaton |
| 2010/0112195 A1 | 5/2010 | Kodas et al. |
| 2010/0113897 A1* | 5/2010 | Brenneman .......... A61B 5/6833 600/310 |
| 2010/0152651 A1 | 6/2010 | Boyden et al. |
| 2010/0298895 A1 | 11/2010 | Ghaffari et al. |
| 2010/0324392 A1 | 12/2010 | Yee et al. |
| 2011/0009824 A1 | 1/2011 | Yodfat et al. |
| 2011/0029269 A1 | 2/2011 | Hayter et al. |
| 2011/0053121 A1 | 3/2011 | Heaton |
| 2011/0089957 A1 | 4/2011 | Sheppard |
| 2011/0125058 A1 | 5/2011 | Levinson et al. |
| 2011/0237917 A1 | 9/2011 | Roy et al. |
| 2011/0257456 A1 | 10/2011 | Kinn et al. |
| 2011/0257495 A1 | 10/2011 | Hoss et al. |
| 2011/0319734 A1 | 12/2011 | Gottlieb et al. |
| 2012/0035442 A1 | 2/2012 | Barman et al. |
| 2012/0046533 A1 | 2/2012 | Voskanyan et al. |
| 2012/0078071 A1 | 3/2012 | Bohm et al. |
| 2012/0108931 A1 | 5/2012 | Taub et al. |
| 2012/0165639 A1 | 6/2012 | Engelhardt et al. |
| 2012/0190950 A1 | 7/2012 | Yang et al. |
| 2012/0190952 A1 | 7/2012 | Stafford |
| 2012/0203078 A1 | 8/2012 | Sze et al. |
| 2012/0209244 A1 | 8/2012 | Gray |
| 2012/0209303 A1 | 8/2012 | Frankhouser et al. |
| 2012/0215087 A1 | 8/2012 | Cobelli et al. |
| 2012/0238841 A1 | 9/2012 | Castle et al. |
| 2012/0265042 A1 | 10/2012 | Neinast et al. |
| 2013/0150691 A1* | 6/2013 | Pace .................. A61B 50/3001 600/347 |
| 2013/0178726 A1 | 7/2013 | Wang et al. |
| 2013/0190583 A1 | 7/2013 | Grosman et al. |
| 2013/0225956 A1 | 8/2013 | Huang et al. |
| 2013/0245401 A1 | 9/2013 | Estes et al. |
| 2013/0248364 A1 | 9/2013 | Kahn et al. |
| 2013/0267811 A1 | 10/2013 | Pryor et al. |
| 2013/0310665 A1 | 11/2013 | Crean et al. |
| 2013/0328578 A1 | 12/2013 | Shah et al. |
| 2013/0331676 A1 | 12/2013 | Morgan et al. |
| 2013/0338598 A1 | 12/2013 | Gyrn |
| 2014/0012510 A1 | 1/2014 | Mensinger et al. |
| 2014/0066735 A1 | 3/2014 | Engelhardt et al. |
| 2014/0275897 A1 | 9/2014 | Pushpala et al. |
| 2015/0038897 A1* | 2/2015 | Daddona ........... A61M 37/0015 604/46 |
| 2015/0182725 A1* | 7/2015 | Finger .................. A61F 9/0017 600/1 |
| 2015/0257687 A1* | 9/2015 | Pushpala .............. A61B 5/1118 600/345 |
| 2016/0038180 A1* | 2/2016 | Kube .................... A61B 5/6832 600/309 |
| 2017/0172475 A1* | 6/2017 | Pushpala ................ G06F 19/00 |
| 2017/0188912 A1* | 7/2017 | Halac ................. A61B 5/14865 |
| 2018/0368771 A1* | 12/2018 | Gray .................. A61B 5/14532 |
| 2020/0178853 A1* | 6/2020 | Pushpala .............. A61B 5/1473 |
| 2021/0204845 A1 | 7/2021 | Pushpala et al. |

FOREIGN PATENT DOCUMENTS

| | | |
|---|---|---|
| CN | 103458810 | 12/2013 |
| EP | 1266608 | 8/2006 |
| EP | 2327362 | 6/2011 |
| JP | 4112499 | 7/2008 |
| JP | 4373604 | 11/2009 |
| JP | 4439733 | 3/2010 |
| JP | 4574847 | 11/2010 |
| JP | 4905906 | 3/2012 |
| JP | 5021115 | 9/2012 |
| JP | 2013502978 | 1/2013 |
| JP | 5591715 | 9/2014 |
| JP | 5640110 | 12/2014 |
| JP | 2015505251 | 2/2015 |
| JP | 5680960 | 3/2015 |
| JP | 5749751 | 7/2015 |
| JP | 5795584 | 10/2015 |
| JP | 2016508763 | 3/2016 |
| JP | 2016517601 | 6/2016 |
| JP | 2016518881 | 6/2016 |
| WO | 1994020602 | 9/1994 |
| WO | 1999045387 | 9/1999 |
| WO | 2000074763 | 12/2000 |
| WO | 2002062202 | 8/2002 |
| WO | 2002097414 | 12/2002 |
| WO | 2008028087 | 3/2008 |
| WO | 2008157820 | 12/2008 |
| WO | 2009082699 | 7/2009 |
| WO | 2009105145 | 8/2009 |
| WO | 2011025549 | 3/2011 |
| WO | 2013058879 | 4/2013 |
| WO | 2013163035 | 10/2013 |
| WO | 2014145001 | 9/2014 |
| WO | 2014145049 | 9/2014 |
| WO | 2015002940 | 1/2015 |

OTHER PUBLICATIONS

AFD China, Summary Report of the First Office Action issued for Chinese Patent Application No. 2014800271779, dated Feb. 8, 2017. 14 pages.

AFD China, Summary Report of the First Office Action issued for Chinese Patent Application No. 2015800127310. dated Aug. 24, 2018. 10 pages.

EPO, Extended European Search Report for European Patent Application No. 15762313.3, dated Sep. 29, 2017. 9 pages.

EPO, Examination Report for European Patent Application No. 15762313.3, dated Mar. 20, 2019. 6 pages.

EPO, Office Action received for European Patent Application No. 14770855.6, dated Nov. 25, 2016.

ISA, International Search Report and Written Opinion for International Patent Application No. PCT/US2014/027655. dated Sep. 5, 2014. 10 pages.

ISA, International Search Report and Written Opinion for International Patent Application No. PCT/US2015/020586. dated Jun. 24, 2015. 9 pages.

\* cited by examiner

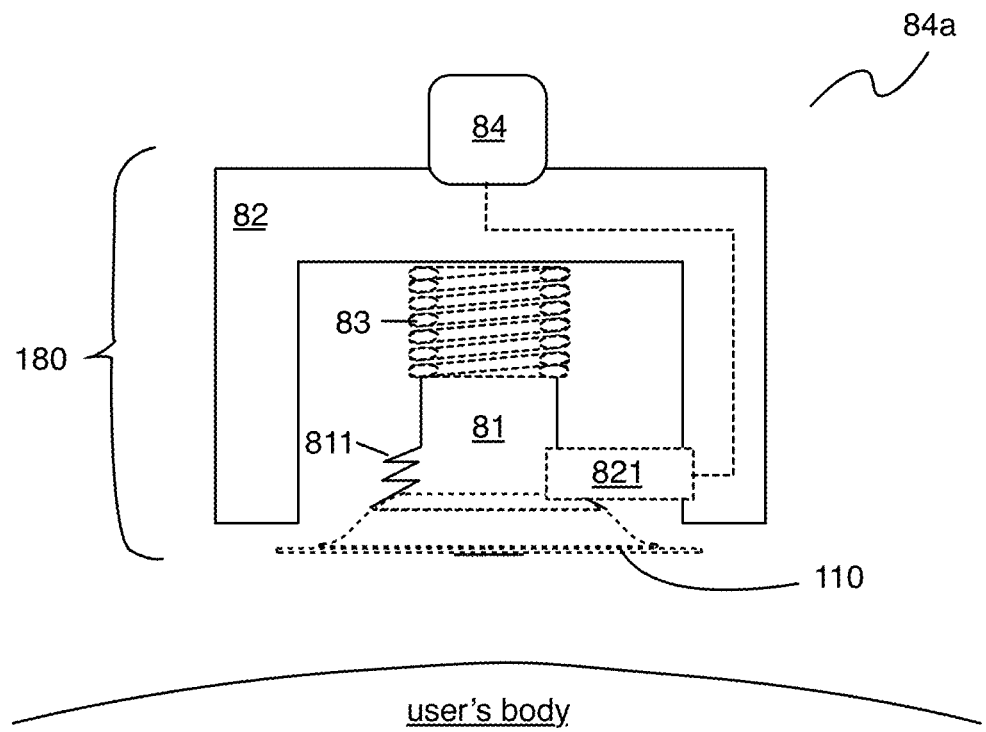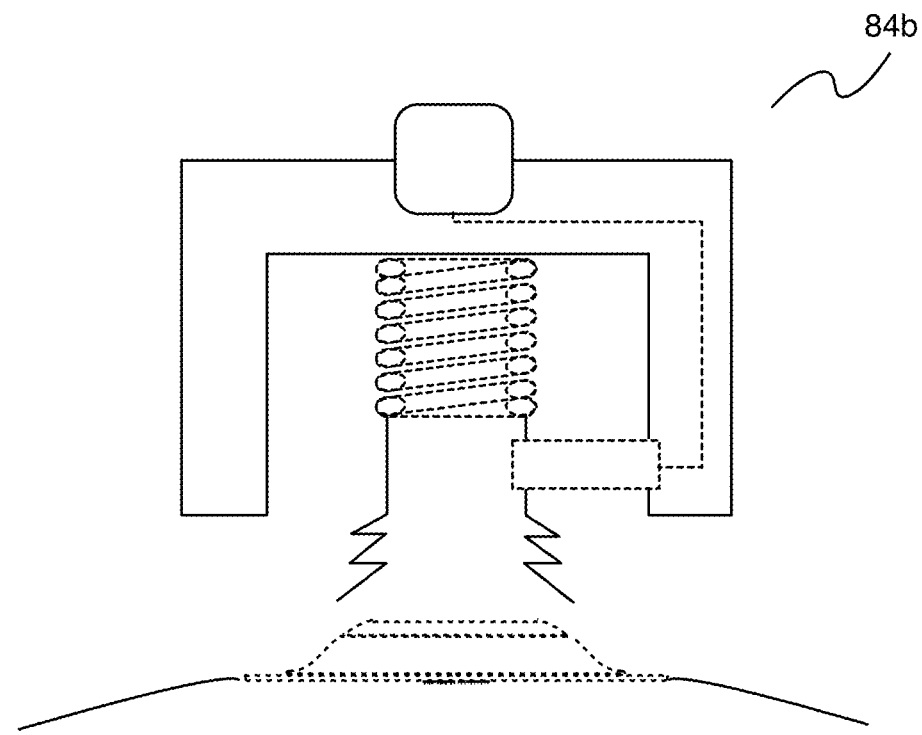
FIGURE 15

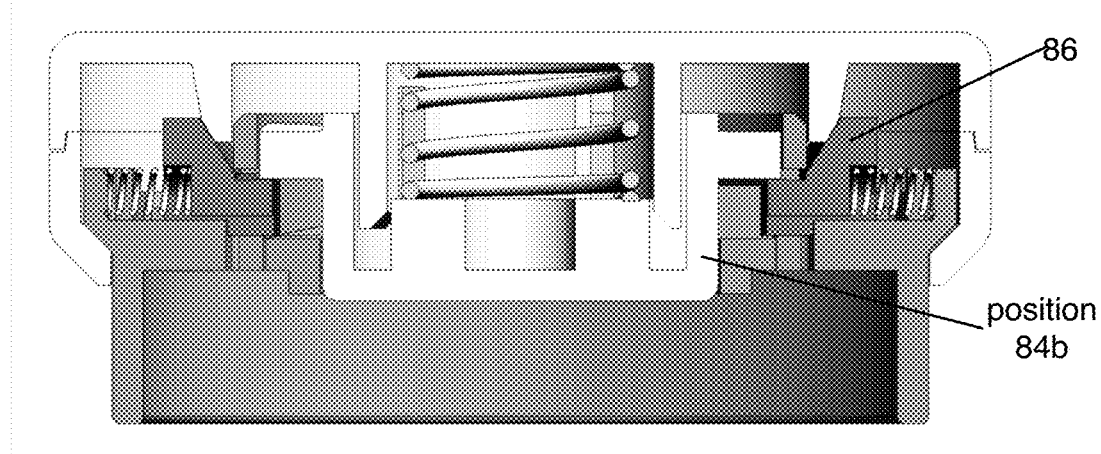
FIGURE 19C
downward force places outward biasing
force on triggers, 86
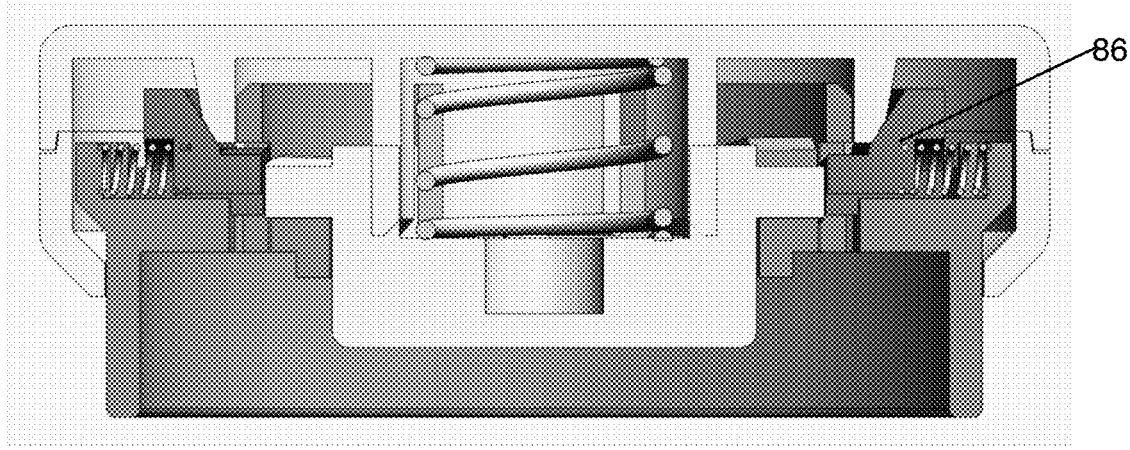
FIGURE 19D Shown in configuration 188a. Downward force on 88 releases trigger (188) to accelerate plunger (184') downward in configuration 188b.

200

receiving a second housing portion into an opening of a first housing portion, the first housing portion supporting a microsensor including a first working electrode, a second working electrode, a reference electrode, and a counter electrode, and the second housing portion supporting an electronics subsystem configured to receive a signal stream from the microsensor — S210 after interfacing with the second housing portion, accelerating the second housing portion toward skin of the user thereby delivering sensing regions of the microsensor into interstitial fluid of the user — S220 generating an impedance signal, from two of the first working electrode, the second working electrode, the reference electrode, and the counter electrode, in response to applying a voltage, near a shifted potential different than a reference potential of the reference electrode — S230 at a processing system in communication with the electronics subsystem, receiving the signal stream and the impedance signal — S240 at the processing system, generating an analysis indicative of an analyte parameter of the user and derived from the signal stream and the impedance signal — S250 transmitting information derived from the analysis to an electronic device associated with the user, thereby facilitating monitoring of body chemistry of the user — S260

FIGURE 23

SYSTEM FOR MONITORING BODY CHEMISTRY

CROSS-REFERENCE TO RELATED APPLICATIONS

This application is a continuation of U.S. application Ser. No. 16/791,518, filed Feb. 14, 2020, which is a continuation of U.S. application Ser. No. 15/601,204, filed May 22, 2017, which is a continuation-in-part of U.S. application Ser. No. 15/412,229, filed Jan. 23, 2017, which is a continuation of U.S. application Ser. No. 14/657,973, filed Mar. 13, 2015, which claims priority to U.S. Provisional Application No. 62/025,174, filed Jul. 16, 2014, U.S. Provisional Application No. 62/012,874, filed Jun. 16, 2014, and U.S. Provisional Application No. 61/952,594, filed Mar. 13, 2014, all of which are incorporated by reference herein in their entireties.

TECHNICAL FIELD

This invention relates generally to the biometric device field, and more specifically to a new and useful system for monitoring body chemistry in the biometric device field.

BACKGROUND

Biomonitoring devices are commonly used, particularly by health-conscious individuals and individuals diagnosed with ailments, to monitor body chemistry. Such biomonitoring devices perform the tasks of determining an analyte level in a user's body, and providing information regarding the analyte level to a user; however, these current biomonitoring devices typically convey information to users that is limited in detail, intermittent, and prompted by the command of the user. Such biomonitoring devices, including blood glucose meters, are also inappropriate for many applications outside of intermittent use, and place significant burdens on users (e.g., in requiring finger sticks, in requiring lancing, etc.) due to design and manufacture considerations. Additionally, current devices are configured to analyze one or a limited number of analytes contributing to overall body chemistry, due to limitations of sensors used in current biomonitoring devices.

There is thus a need in the biometric device field to create a new and useful system for monitoring body chemistry. This invention provides such a new and useful system.

BRIEF DESCRIPTION OF THE FIGURES

FIG. 15 depicts an embodiment of an applicator system in an embodiment of a system for monitoring body chemistry;

FIGS. 19A-19D depict a first specific example of a applicator system in an embodiment of a system for monitoring body chemistry;

FIG. 23 depicts an embodiment of a method for monitoring body chemistry;

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. System

Figure 1:
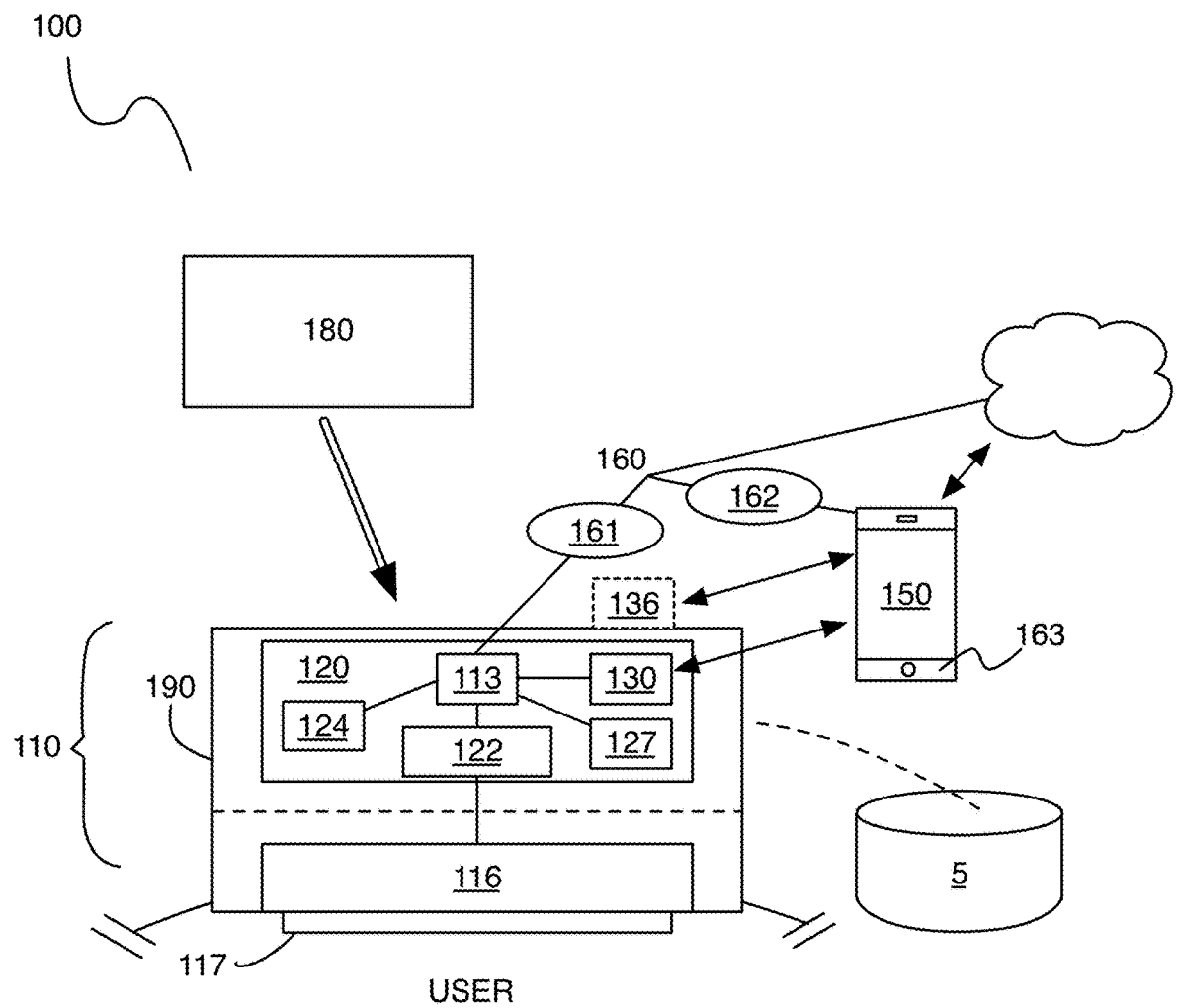
FIG. 1 depicts elements of an embodiment of a system for monitoring body chemistry.

As shown in FIG. 1, an embodiment of the system 100 for monitoring body chemistry of a user comprises a housing 190 that supports a microsensor 116 and an electronics subsystem 120 in communication with the microsensor 116; and a processing subsystem 160 configured to generate an analysis indicative of an analyte parameter of the user, wherein the analysis is derived from a signal stream of the microsensor and an impedance signal from the electronics subsystem. In more detail, the housing 190, microsensor 116, and the electronics subsystem 120 can be configured as a microsensor patch 110 configured to sense analyte levels in a user's body, wherein the electronics subsystem includes a signal conditioning module 122, a power management module 124, a storage module 127, and a transmitting unit 130 in communication with the processing subsystem 160 and/or an electronic device (e.g., mobile computing device 150) associated with the user.

In some variations, the system 100 can further include an applicator system 180 configured to facilitate application of the microsensor patch 110 onto the body of a user in a reliable manner. The system 100 functions to provide continuous monitoring of a user's body chemistry through reception and processing of signals associated with one or more analytes present in the body of the user, and to provide an analysis of the user's body chemistry to the user and/or an entity (e.g., health care professional, caretaker, relative, friend, acquaintance, etc.) associated with the user. Alternatively, the system 100 can function to detect a user's body chemistry upon the user's request or sporadically, and/or can provide an analysis of the user's body chemistry only to the user.

The system 100 is configured to be worn by the patient outside of a clinical (e.g., hospital) or research (e.g., laboratory) setting, such that the patient can be in a non-contrived environment as he or she is interfacing with the microsensor patch 110 for monitoring of body chemistry. Furthermore, elements of the system 100 can be reusable or disposable (e.g., based upon modularity of the system 100), or the entire system 100 can be configured to be disposable. In one specific example, the system 100 adheres to the patient (thus not compelling the patient to hold any part of the system 100 by hand), has a low profile that conforms to the patient, and is configured to receive and transmit signals indicative of body chemistry parameters of the user, for downstream analysis and information transfer to the user. Alternatively, the system 100 can be substantially non-portable, non-wearable, and/or intended for use in a clinical or research setting.

As indicated above and further below, elements of the system can be implemented on one or more computer networks, computer systems, or applications servers, etc. The computer system(s) can comprise one or more of: a cloud-based computer, a mainframe computer system, a grid-computer system, or any other suitable computer system, and the computer system can support collection of data from a wearable device and/or a base station, processing of these data, and transmission of alerts, notifications, and/or user interface updates to one or more electronic computing devices (e.g., mobile computing device, wrist-borne mobile computing device, head-mounted mobile computing device, etc.) linked to or affiliated with an account of the user. For example, the computer system can receive signals indicative of one or more analyte parameters of the user and distribute alerts and notifications over a distributed network, such as over a cellular network or over an Internet connection. In this example, the computer system can upload alerts and notifications to a native body chemistry monitoring application including the user interface and executing on a mobile computing device associated with the user.

Additionally or alternatively, an electronic computing device (e.g., a laptop computer, a desktop computer, a tablet, a smartphone, a smart watch, a smart eyewear accessory, a personal data assistant, etc.) associated with the system (e.g., with the account of the user) can maintain the account of the user, create and maintain a user-specific model within the account, and execute a native body chemistry monitoring application (including the user interface) with functions including one or more of: generating alerts or notifications, receiving alerts or notifications, displaying alerts or notifications, updating predictions of changes in state of the user, and any other suitable function that enhances body chemistry monitoring of the user. The system 100 is preferably configured to implement at least a portion of the method 200 described in Section 2 below; however, the system 100 can additionally or alternatively be configured to implement any other suitable method.

1.1 System—Microsensor Patch

As shown in FIG. 1, the microsensor patch 110 comprises a microsensor 116 and an electronics subsystem 120 in communication with the microsensor 116, wherein the microsensor 116 and the electronics subsystem 120 are supported by a housing 190. The microsensor patch no can be configured to detect and sense only a single analyte; however, the microsensor patch no can alternatively be configured to detect and sense multiple analytes in order to provide an analysis based on multiple analytes. Preferably, the microsensor patch no is configured to be disposable; however, the microsensor patch no can alternatively be configured to be reusable for any suitable duration or number of uses. In one variation, the microsensor patch no is configured to be a semi-permanent component (e.g., wearable for a week before replacement, wearable for a month before replacement, etc.) configured to sense the user's body chemistry with minimal signal degradation for at least a week post-coupling of the microsensor patch no to the body of the user. However, in another variation, the microsensor patch no can be configured to be a permanent component configured to permanently couple to a user. Modularity of the microsensor patch no is described in further detail below.

1.1.1 System—Microsensor

Figure 2A:
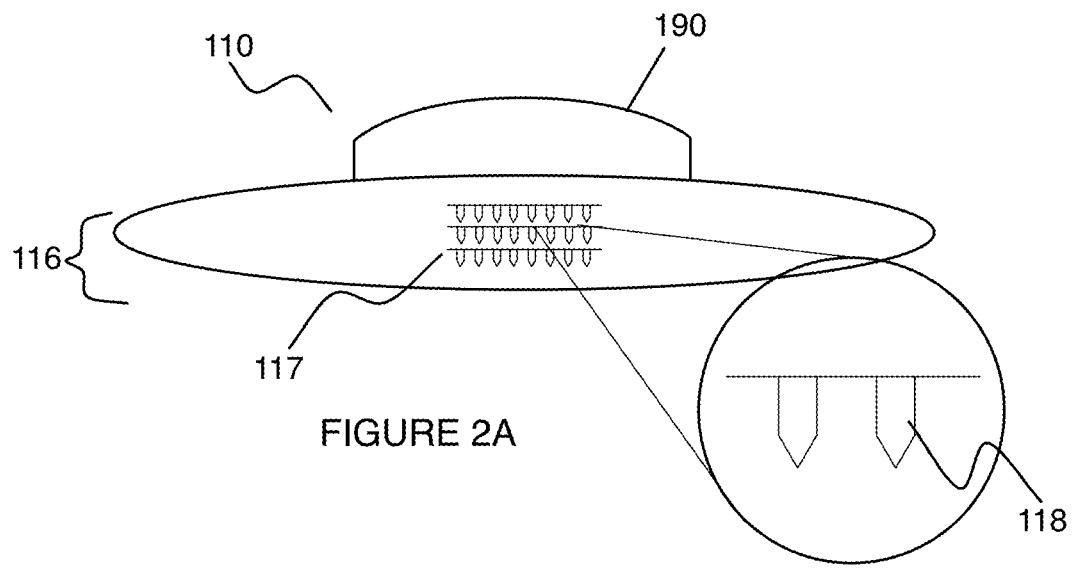
FIGS. 2A and 2B depict embodiments of a microsensor patch, a transmitting unit, a housing, and an array of filaments in an embodiment of a system for monitoring body chemistry.

The microsensor 116 of the microsensor patch no preferably comprises an array of filaments 117, as shown in FIGS. 1 and 2A, and functions to penetrate skin of the user in order to sense one or more analytes characterizing the user's body chemistry. Preferably, the array of filaments 117 is configured to penetrate the user's stratum corneum (i.e., an outer skin layer) in order to sense analytes within interstitial (extracellular) fluid, which is throughout the body; however, the array of filaments 117 can be configured to penetrate the user's skin to any other suitable depth. For instance, the microsensor 116 can alternatively be configured to penetrate deeper layers, or various depth layers of a user's skin in order to sense analytes within any appropriate bodily fluid of the user. The microsensor 116 can be configured to sense analytes/ions characterizing a user's body chemistry using a potentiometric measurement (e.g., for small analytes including potassium, sodium calcium, etc.), using an amperometric measurement (e.g., for large analytes including glucose, lactic acid, creatinine, etc.), using a conductometric measurement, and/or using any other suitable measurement.

Preferably, sensed analytes result in a signal (e.g., voltage, current, resistance, capacitance, impedance, gravimetric, etc.) detectable by the electronics subsystem 120 in communication with the microsensor 116; however, analyte sensing can comprise any other appropriate mechanism using the microsensor 116. As mentioned earlier, the microsensor 116 is also preferably integrated with the electronics subsystem 120. In a first variation, the microsensor 116 is coupled to the semiconductor architecture of the electronics subsystem 120 (e.g., the microsensor 116 is coupled to an integrated circuit comprising the electronics subsystem 120), in a second variation, the microsensor 116 is more closely integrated into the semiconductor architecture of the electronics subsystem 120 (e.g., there is closer integration between the microsensor 116 and an integrated circuit including the electronics subsystem 120), and in a third variation, the microsensor 116 and the electronics subsystem 120 are constructed in a system-on-a-chip fashion (e.g., all components are integrated into a single chip). As such, in some variations, filaments the array of filaments 117 of the microsensor 116 can be directly or indirectly integrated with electronics components, such that preprocessing of a signal from the microsensor 116 can be performed using the electronics components (e.g., of the array of filaments 117, of the electronics subsystem 120) prior to or after transmitting signals to the electronics subsystem 120 (e.g., to an analog front end, to an analog to digital converter). The electronics components can be coupled to a filament substrate, or otherwise integrated with the filaments in any suitable fashion (e.g., wired, using a contact pad, etc.). Alternatively, the electronics components can be fully integrated into the electronics subsystem 120 and configured to communicate with the microsensor 116, or the electronics components can be split between the microsensor and the electronics subsystem 120. The microsensor 116 can, however, comprise any other suitable architecture or configuration.

The microsensor 116 preferably senses analyte parameters using the array of filaments 117, such that absolute values of specific analytes/ions can be detected and analyzed. The microsensor 116 can additionally be configured to sense analyte parameters using the array of filaments 117, such that changes in values of specific analyte/ion parameters or derivatives thereof (e.g., trends in values of a parameter, slopes of curves characterizing a trend in a parameter vs. another parameter, areas under curves characterizing a trend, a duration of time spent within a certain parameter range, etc.) can be detected and analyzed. In one variation, sensing by the microsensor 116 is achieved at a low frequency at discrete time points (e.g., every minute, or every hour), and in another variation, sensing by the microsensor 116 is achieved substantially continuously at a high frequency (e.g., every picosecond, every millisecond, every second). In one specific example for blood chemistry analysis, the array of filaments 117 of the microsensor 116 is configured to sense one or more of: electrolytes, glucose, bicarbonate, creatinine, body urea nitrogen (BUN), sodium, iodide, iodine and potassium of a user's blood chemistry. In another specific example, the array of filaments 117 of the microsensor 116 is configured to sense at least one of biomarkers, cell count, hormone levels, alcohol content, gases (e.g. carbon dioxide, oxygen, etc.), drug concentrations/metabolism, pH and analytes within a user's body fluid.

As shown in FIG. 2A, the array of filaments 117 is preferably located at the base surface of the microsensor patch 110, and functions to interface directly with a user in a transdermal manner (e.g., in accessing interstitial fluid) in order to sense at least one analyte/ion characterizing the user's body chemistry. The array of filaments 117 is preferably arranged in a uniform pattern with a specified density optimized to effectively penetrate a user's skin and provide an appropriate signal, while minimizing pain to the user. Additionally, the array of filaments 117 can be arranged in a manner to optimize coupling to the user, such that the microsensor firmly couples to the user over the lifetime usage of the system. For example, the filaments 118 can comprise several pieces and/or be attached to a flexible base to allow the array of filaments 117 to conform to a user's body. In one variation, the array of filaments 117 is arranged in a rectangular pattern, and in another variation, the array of filaments 117 is arranged in a circular or ellipsoid pattern. However, in other variations, the array of filaments 117 can be arranged in any other suitable manner (e.g., a random arrangement). The array of filaments 117 can also be configured to facilitate coupling to a user, by comprising filaments of different lengths or geometries. Having filaments 118 of different lengths can further function to allow measurement of different ions/analytes at different depths of penetration (e.g., a filament with a first length can sense one analyte at a first depth, and a filament with a second length can sense another analyte at a second depth). The array of filaments 117 can also comprise filaments 118 of different geometries (e.g., height, diameter) to facilitate sensing of analytes/ions at lower or higher concentrations. In one specific example, the array of filaments 117 is arranged at a density of 100 filaments per square centimeter and each filament 118 in the array of filaments 117 has a length of 250-350 microns, which allows appropriate levels of detection, coupling to a user, and pain experienced by the user.

Figure 2B:
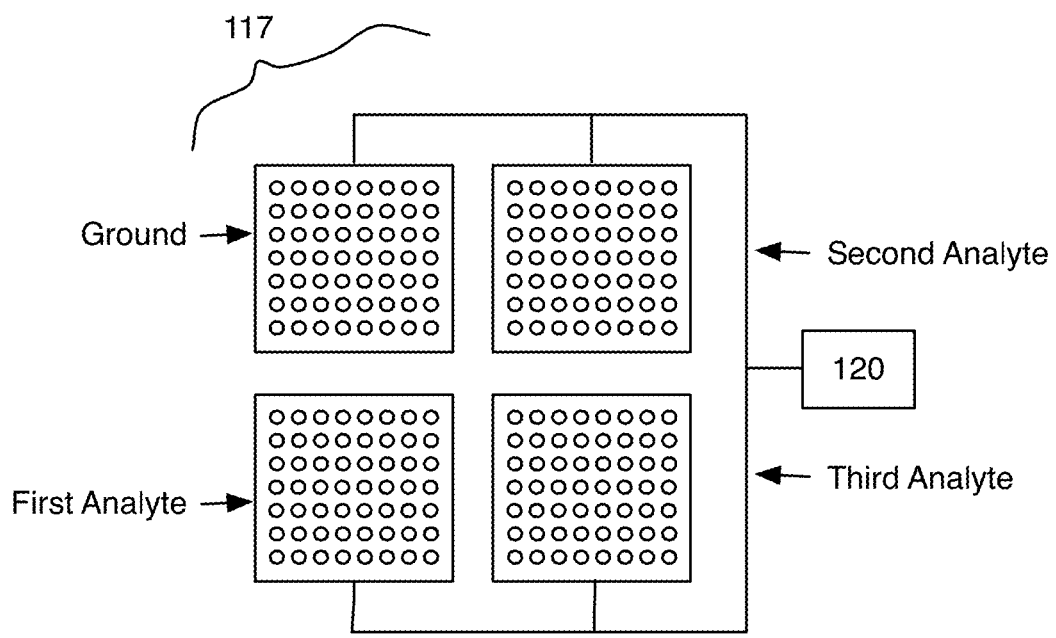
Figure 2C:
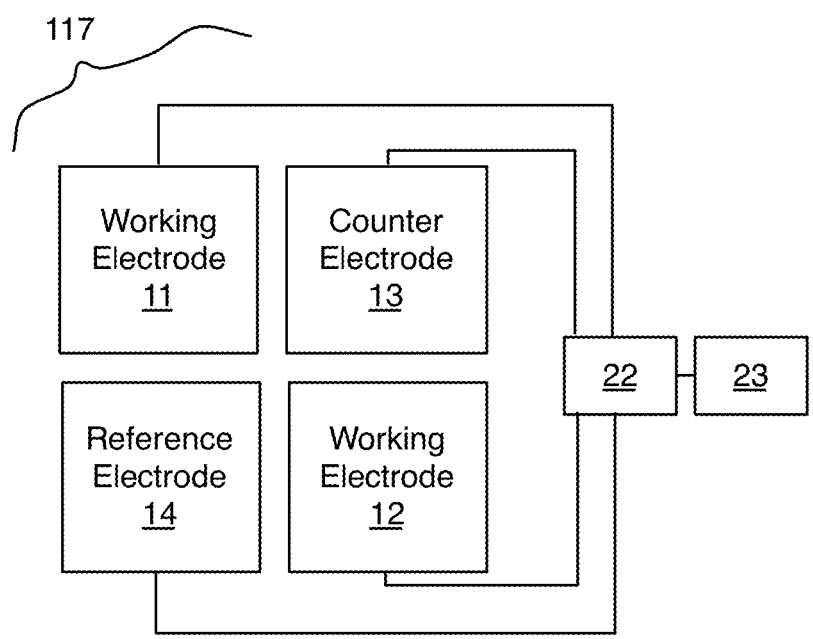
FIG. 2C depict a variation of electrodes in an embodiment of a system for monitoring body chemistry.
Figure 3A:
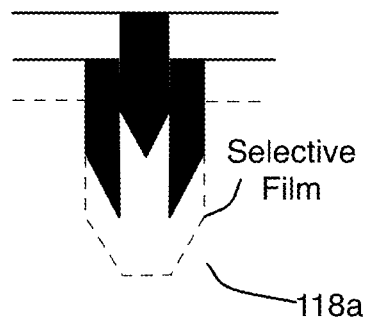
FIGS. 3A-3H depict examples of filament variations in an embodiment of a system for monitoring body chemistry.
Figure 3B:
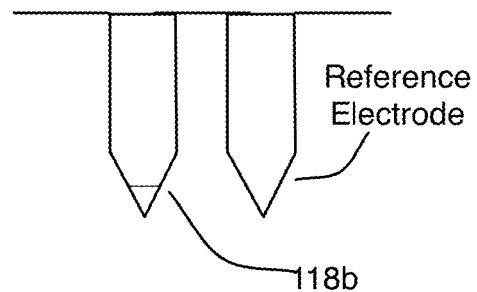
Figure 3C:
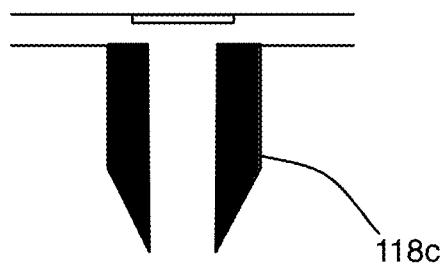
Figure 3D:
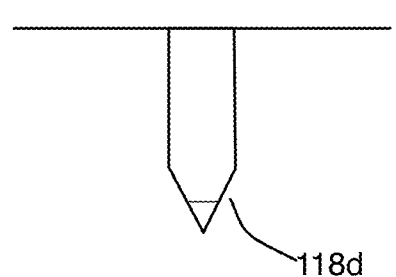
Figure 3E:
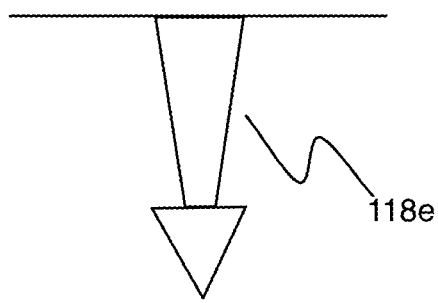
Figure 3F:
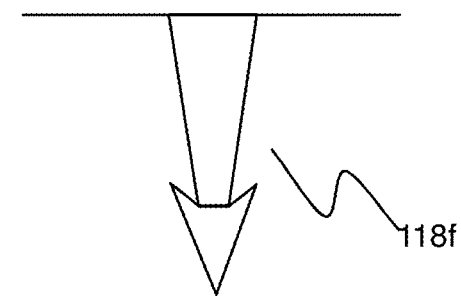
Figure 3G:
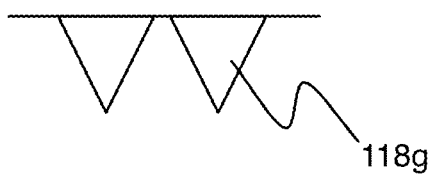
Figure 3H:
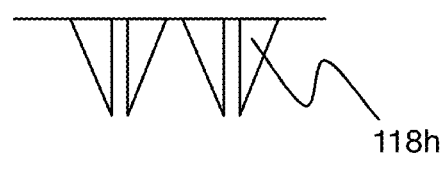

Each filament 118 in the array of filaments 117 preferably functions to sense a single analyte; however, each filament 118 in the array of filaments 117 can additionally be configured to sense more than one analyte. Furthermore, the array of filaments 117 can be further configured, such that a subarray of the array of filaments 117 functions as a single sensor configured to sense a particular analyte or biomarker, as shown in FIG. 2B. Furthermore, any configuration of subarrays of the array of filaments 117 can additionally or alternatively be configured as one or more of: a working electrode, a counter electrode (i.e., auxiliary electrode), and a reference electrode, for instance, in a two-electrode cell, a three-electrode cell, or a more-than-three-electrode cell. In one variation, as shown in FIG. 2C, the array of filaments 117 of the microsensor 116 is configured as a first working electrode 11 (corresponding to a first subarray of filaments), a second working electrode 12 (corresponding to a second subarray of filaments), a counter electrode 13 (corresponding to a third subarray of filaments), and a reference electrode 14 (corresponding to a fourth subarray of filaments). In a specific example of this variation, each subarray associated with the first working electrode 11, the second working electrode 12, the counter electrode 13, and the reference electrode 14, respectively, is substantially identical in morphology (e.g., area of the microsensor). Furthermore, in the specific example, each subarray has a square footprint, and the subarrays are configured in a 2×2 arrangement to define a larger square footprint. However, the array of filaments 117 can be configured as one or more of: a working electrode, a counter electrode, and a reference electrode in any other suitable manner, and can furthermore have any other suitable morphology(ies) and/or configuration relative to each other.

Additionally or alternatively, any subarray of the array of filaments 117 can be configured to release biomaterials (e.g., therapeutic substances, drugs) for treating a medical condition of a user (e.g., as facilitated by biomaterial dissolution in interstitial fluid). Multiple subarrays of the array of filaments can then be configured to sense different analytes/biomarkers, or the same analyte/biomarker. Furthermore, a subarray or a single filament 118 of the array of filaments 117 can be configured as a ground region of the microsensor 116, such that signals generated by the microsensor 116 in response to analyte detection can be normalized by the signals generated by the subarray or single filament 118 serving as a ground region. Preferably, all subarrays of the array of filaments 117 are substantially equal in size and density; however, each subarray of the array of filaments 117 can alternatively be optimized to maximize signal generation and detection in response to a specific analyte. In an example, analytes that are known to have a lower concentration within a user's body fluid can correspond to a larger subarray of the array of filaments 117. In another example, analytes that are known to have a higher concentration within a user's body fluid can correspond to a smaller subarray of the array of filaments 117. In one extreme example, an entire array of filaments can be configured to sense a single analyte, such that the microsensor 116 and microsensor patch 110 is configured to sense and detect only one analyte. In another extreme example, each single filament in an array can be configured to detect a single analyte allowing for detection of multiple analytes within a single array (e.g., for a 100-filament array, 100 analytes can be tested).

In other variations, a subarray of the array of filaments 117 can also be used to detect other physiologically relevant parameters, such as electrophysiological signals (e.g., electrocardiogram, electroencephalogram), body temperature, respiration, and skin impedance change (e.g., to measure hydration state or inflammatory response). In these other variations, the subarray can be dedicated to measuring these physiologically relevant parameters, which could be combined with analyte/ion parameter measurements in order to provide meaningful information to a user. As an example, the simultaneous measurement of potassium levels and electrocardiogram measurements, enabled by subarrays of the array of filaments 117, can provide a more complete diagnosis of cardiovascular problems or events than either measurement by itself.

A filament 118 of the array of filaments can comprise one or more of: a substrate core, the substrate core including a base end coupled to the substrate, a columnar protrusion having a proximal portion coupled to the base end and a distal portion, and a tip region coupled to the distal portion of the columnar protrusion and that facilitates access to the body fluid of the user; a conductive layer, isolated to the tip region of the substrate core and isolated away from the base end and the columnar protrusion as an active region that enables transmission of electronic signals generated upon detection of an analyte; an insulating layer ensheathing the columnar protrusion and base end of the substrate core and exposing a portion of the conductive layer, thereby defining a boundary of the active region; a sensing layer, in communication with the active region, characterized by reversible redox behavior for transduction of an ionic concentration of the analyte into an electronic signal; an intermediate selective layer superficial to the conductive layer and deeper than the sensing layer, relative to a most distal point of the tip region of the filament, that facilitates detection of the analyte; an intermediate protective layer, superficial to the intermediate selective layer, including a functional compound that promotes generation of a protective barrier; and a selective coating superficial to the intermediate protective layer, having a distribution of molecules that respond to presence of the analyte, superficial to the sensing layer. Thus, a filament can comprise one or more regions, morphologies (examples of which are shown in FIGS. 3A-3H, with elements 118a-118h), compositions, and/or configurations as described in U.S. Pub. No. 2014/0275897, entitled "On-Body Microsensor for Biomonitoring" and filed on 14 Mar. 2014 and/or U.S. App. No. 62/025,174, and entitled "System for Monitoring Body Chemistry" and filed on 16 Jul. 2014, which are each incorporated herein in their entirety by this reference. However, the filament can additionally or alternatively comprise any other suitable region, composition, morphology, and/or configuration.

Figure 24:
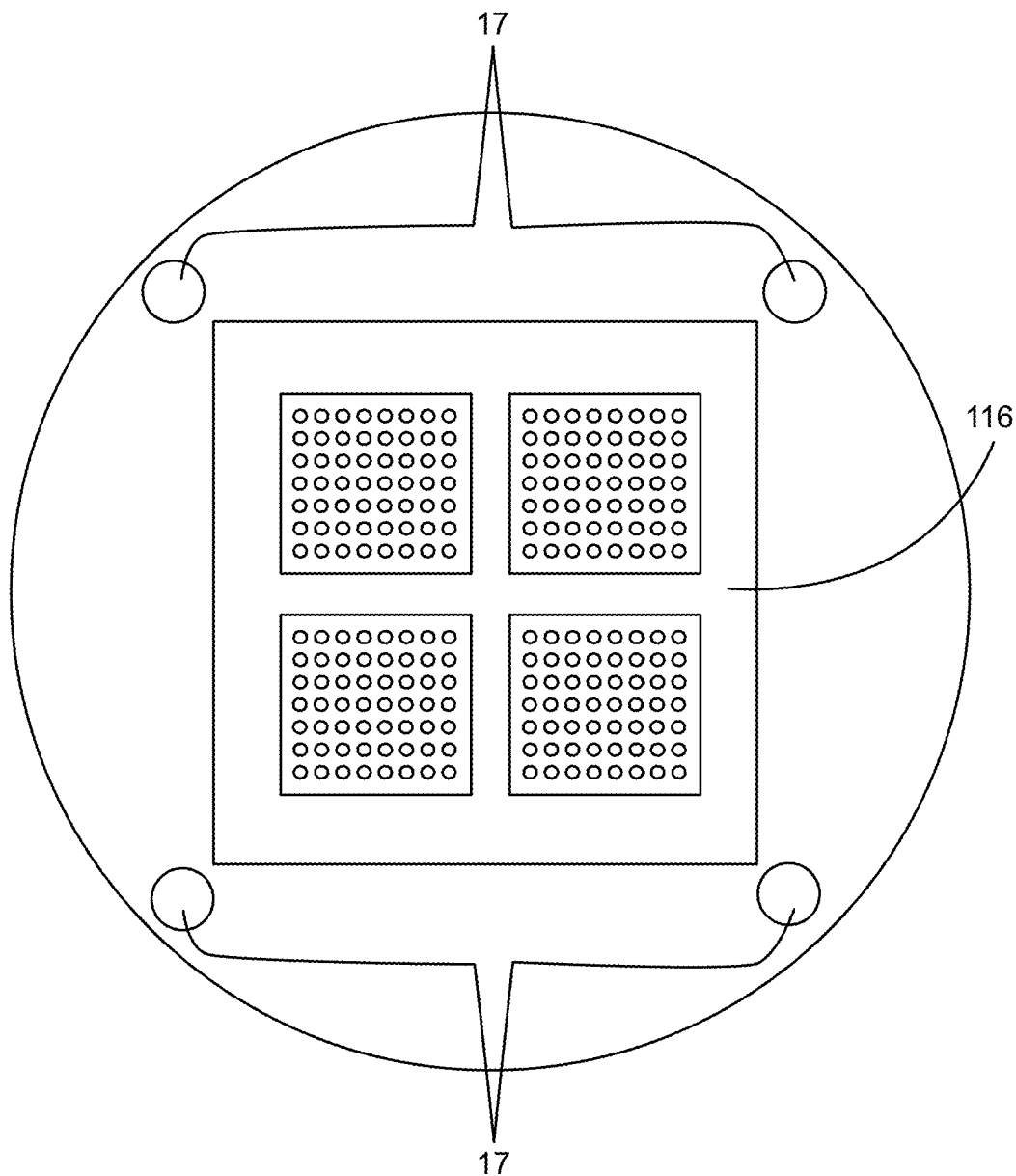
FIG. 24 depicts a portion of a variation of a system for monitoring body chemistry.

In general, the system 100 can include components configured to protect portions of the microsensor 116 during manufacturing, packaging, and/or use of the system 100. For instance, a mold of impact-absorbing material 17 can be positioned about the edge regions of the microsensor 116, in order to protect edges of the microsensor 116 from damage (e.g., as a barrier). The mold of impact-absorbing material 17 can additionally or alternatively function to protect skin of the user from irritation caused by edge-regions of the microsensor. The mold can comprise a continuum of material (e.g., polymeric material), or can include a set of bumpers or spacers of material (e.g., polymeric material) to protect the microsensor 116, an example of which is shown in FIG. 24. Additionally or alternatively, the material of the edge-protecting portion can be dispensed (e.g., as a gel, as an epoxy) during manufacture. However, the system 100 can additionally or alternatively include any other suitable microsensor 116 supporting elements.

1.1.2 System—Electronics Subsystem

Figure 4:
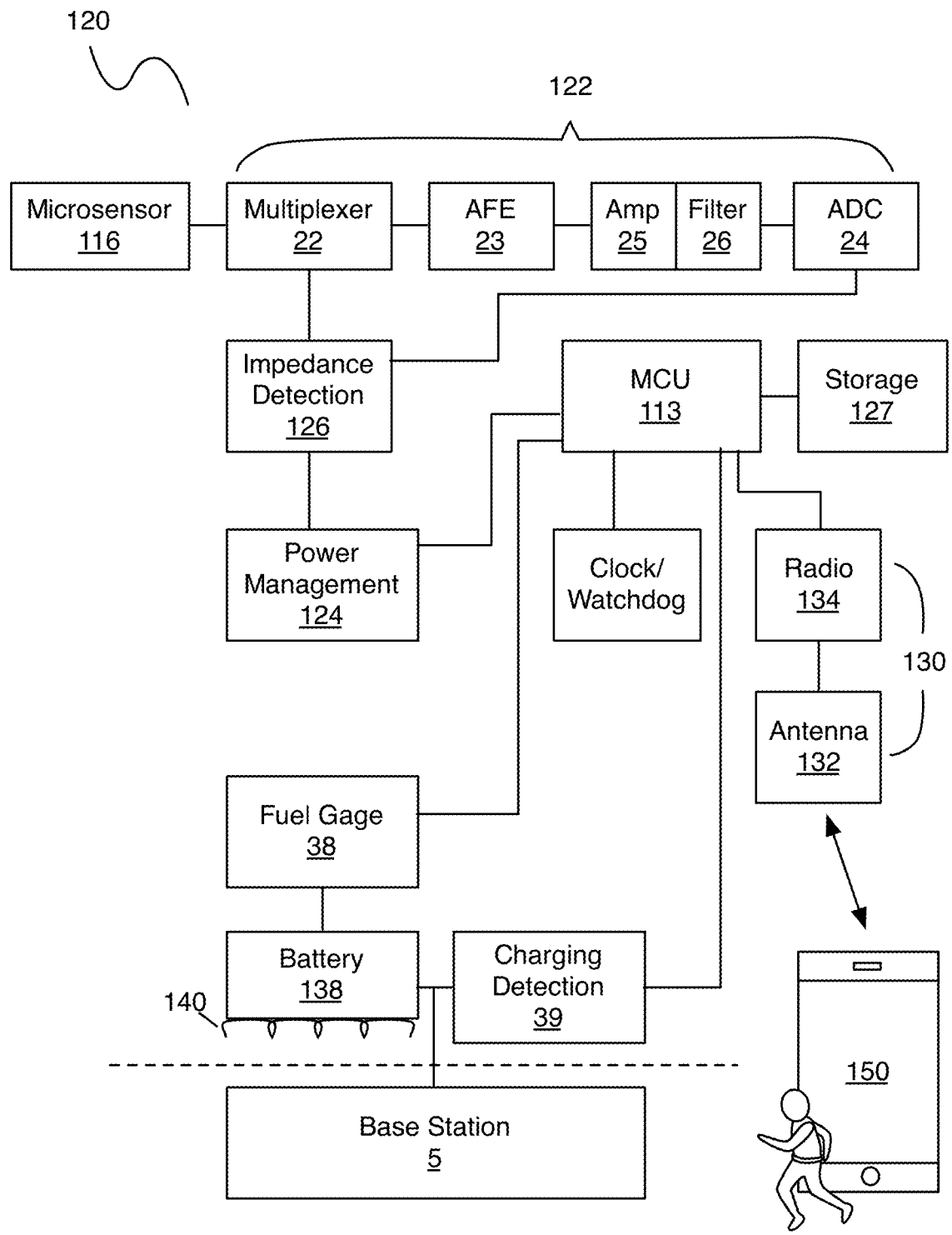
FIG. 4 depicts an embodiment of an electronics subsystem in an embodiment of a system for monitoring body chemistry.

The electronics subsystem 120 functions to receive analog signals from the microsensor 116 and to convert them into digital signals to be processed by a microprocessor 113 of the electronics subsystem 120. In receiving signals, processing signals, regulating function, storing data, and/or transmitting data, the electronics subsystem 120 preferably includes a microprocessor 113 interfacing with one or more of: a signal conditioning module 122, a power management module 124, an impedance detection module 126, a storage module 127, and a transmitting unit 130, as shown in FIG. 4. However, the electronics subsystem 120 can additionally or alternatively include any other suitable modules configured to facilitate signal reception, signal processing, and data transfer in an efficient manner.

The microprocessor 113 preferably includes memory and/or is coupled to a storage module 127 (e.g., flash storage). The microprocessor 113 can also include and/or be coupled to a clock/watchdog module (which can be incorporated into a microcontroller unit) for control of timing between different functions of the electronics subsystem 120. The microprocessor 113 functions to process received signals, enable power distribution, enable impedance monitoring, and enable data transmission from the electronics subsystem 120, in relation to other portions of the electronics subsystem 120 described below; however, the microprocessor 113 can alternatively or additionally be configured to perform any other suitable function.

The signal conditioning module 122 functions to preprocess signals detected and received using the microsensor 116, thereby producing conditioned data prior to processing at the processing subsystem 160. The signal conditioning module 122 can include one or more of: a signal multiplexer, an analog front end, an amplifier (e.g., a variable gain amplifier), a filter (e.g., low pass filter, high pass filter, band pass filter, etc.), an analog-to-digital converter (ADC), and a digital-to-analog converter (DAC). In one variation, as shown in FIG. 4, the signal conditioning module 122 comprises a multiplexer 22 in communication with the microsensor 116, wherein the multiplexer 22 is configured to communicate an output to an analog front end 23 that interfaces the microsensor 116 with an ADC 24 by way of a variable gain amplifier 25 coupled to a filter 26. In a specific example of this variation, the analog front end 23 circuitry is configured with a shifted potential different than a reference potential of the reference electrode 14 of the microsensor 116, wherein the shifted potential is different (e.g., −2V to 2V different) from the reference potential of the reference electrode 14. The configuration involving a difference between the shifted potential and the reference potential can allow the system 100 to drive redox reactions at the surface of the microsensor 110. However, in alternative variations of the specific example, the analog front end (or any other element of the signal conditioning module 122) can be configured with any other suitable potential relative to potentials of electrodes of the microsensor 116.

In more detail, the multiplexer 22 of the signal conditioning module 122 is preferably configured to receive multiple signals from the microsensor 116 (e.g., from subarrays of the array of filaments 117) and to forward the multiple signals received at multiple input lines in a single line at the analog front end. The multiplexer 22 thus increases an amount of data that can be transmitted within a given time constraint and/or bandwidth constraint. The number of input channels to the multiplexer 22 is preferably greater than or equal to the number of output channels of the microsensor 116, and can have any suitable relationship between the number of input lines into the multiplexer 22, select lines of the multiplexer, and output lines from the multiplexer 22. In some variations, the multiplexer 22 can include a post-multiplexer gain in order to reduce capacitance values of the analog front end 23 coupled to the multiplexer 22, and which can also be used to limit a number of amplifiers of the electronics 120, such that a single amplifier is coupled to the multiplexer 22 (as opposed to amplifiers coupled to each individual sensor); however, the multiplexer 22 can alternatively not include any gain producing elements. In some variations, the multiplexer 22 can additionally or alternatively include high frequency and/or low frequency limiting elements. However, the multiplexer 22 can additionally or alternatively be configured in any other suitable manner. Furthermore, in alternative variations, the signal conditioning module 122 can omit a multiplexer and/or comprise or omit any other suitable element.

Figure 5A:
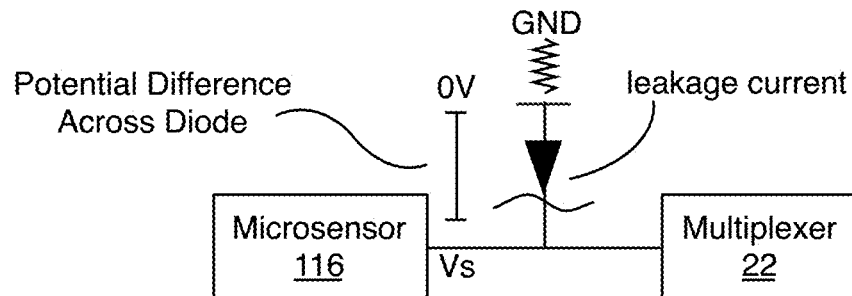
FIGS. 5A-5C depict examples of a portion of an electronics subsystem in an embodiment of a system for monitoring body chemistry.
Figure 5B:
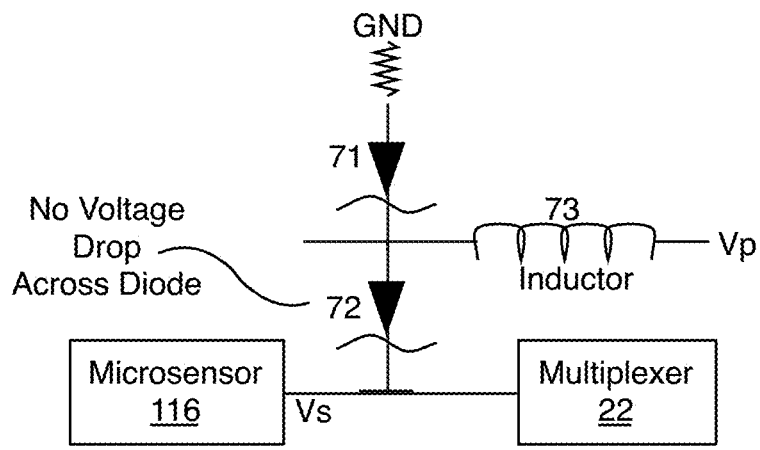
Figure 5C:
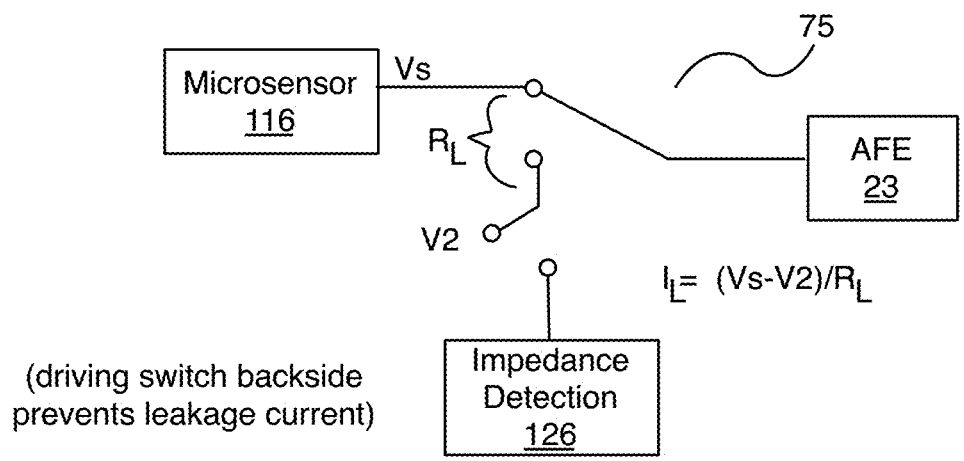

In variations, an interface between the microsensor 116 and other elements of the electronics subsystem 120 can be configured in a manner that prevents or otherwise reduces leakage current effects due to a redox potential of the microsensor 16 in relation to other elements electronics subsystem 120. In a first configuration, a leakage current effect can result when a diode to ground (e.g., an ESD-diode to ground) is configured at an interface between the microsensor 116 and a multiplexer 22, as shown in FIG. 5A. To prevent or otherwise reduce the leakage current effect, a set of diodes 70, comprising a first diode 71 (e.g., a first ESD-diode) and a second diode 72 (e.g., a second ESD-diode), configured at an interface between the microsensor 116 and the multiplexer 22 can be coupled to an element 73 (e.g., inductor, ferrite bead, resistor, etc.) that provides a high resistance to transient voltage spikes and directs any discharge through the second diode 72 to ground (instead of damaging the electronics subsystem 120), as shown in FIG. 5B. The multiplexer 22 can also comprise a switch 75, as shown in FIG. 5C, that allows altering of potentials within the analog front end 23. As shown in FIG. 5C, eliminating a voltage difference (i.e., between Vs and V2) eliminates or otherwise reduces leakage currents that can affect readings from the microsensor 110.

The power management module 124 functions to provide dynamic modulation of power transfer to and from elements of the microsensor patch 110, in a manner that enables efficient operation of the system 100. Preferably, the power management module 124 interfaces with a battery 138 and elements of the transmitting unit 130 requiring power (e.g., by way of a microprocessor 113, as shown in FIG. 4), as described in further detail below. Additionally, the power management module 124 can further interface with an external processing element of the processing subsystem 160, such that the power management module 124 can be at least partially implemented in firmware. In one such variation of the power management module 124, wherein power management is achieved in firmware, the power management module 124 can be configured to anticipate power requirements of one or more elements, and to automatically operate at the highest demanded power mode (e.g., voltage) required, while never dropping below a minimum power level required by the elements. The power management module 124 can also facilitate efficient switching of components to an "off" state when not needed, in order to contribute to lower current consumption. Additionally or alternatively, the power management module 124 can be configured to dynamically trigger high current draw sensing components (e.g., the impedance detection module 126) to an "on" state, only when needed, by monitoring other system components (e.g., voltage of a counter electrode 13).

Figure 6A:
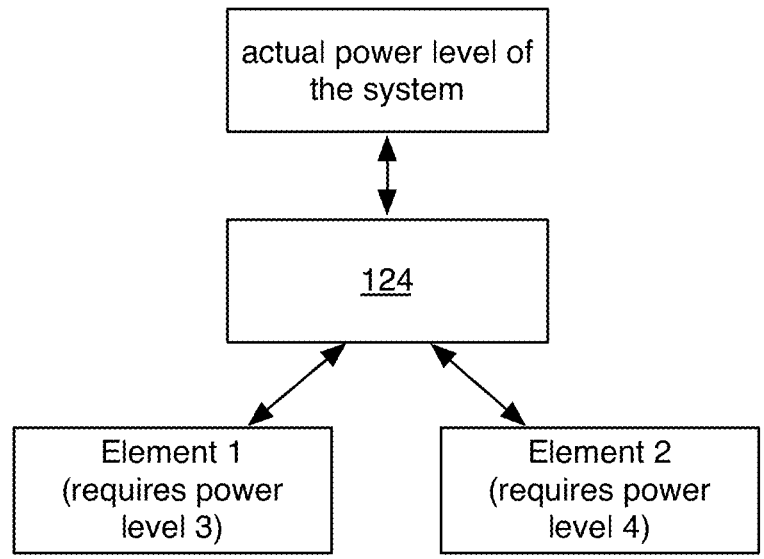
FIGS. 6A-6B depict examples of power management modules in an embodiment of a system for monitoring body chemistry.

In an example, as shown in FIG. 6A, a group of elements requiring different operating power levels can be coupled to the power management module 124, and the power management module 124 can output power at the highest operating power level anticipated among the elements. Disparate elements can also set a minimum level of power they require, and as elements vary their power requirements, the power management module 124 can then automatically adjust power output such that a power level provided never drops below the lowest power level required. In this variation, elements of the microsensor patch 110 requiring power are thus dynamically provided with their highest demanded power level, to substantially limit energy wasted by the system 100 and to satisfy power level requirements of all running elements. In another variation of the power management module 124, wherein power management is achieved in firmware, the power management module 124 can be configured to detect elements requiring power, and to automatically operate at the highest demanded power mode (e.g., voltage) required. In an example, a group of elements requiring different operating voltages can be detected, and the power management module 124 can output power at the highest operating voltage detected. As elements vary their voltage requirements, the power management module 124 can then automatically adjust voltage output to meet the highest demanded voltage. In this variation, elements of the microsensor patch 110 requiring power are thus dynamically provided with their highest demanded voltage, to substantially limit energy wasted by the system 100.

Figure 6B:
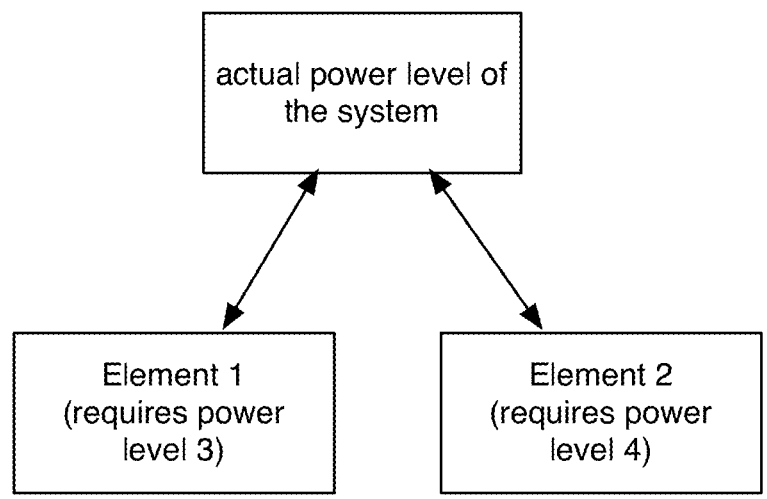

In other variations, power management can be achieved by the power management module 124 without implementation in firmware, such that power management occurs in circuitry. In these other variations, an example of which is shown in FIG. 6B, power management can comprise providing a set amount of power to elements requiring power, and completely eliminating power transfer to elements not requiring power. The system 100 can, however, comprise any other suitable variation of the power management modules 124.

In relation to the power management module 124, the electronics subsystem 120 can comprise a battery 138, which functions to serve as a power source for the electronics subsystem 120. The battery 138 is preferably coupled to a fuel gage 38 and a charging detection module 39, each of which is coupled to the microprocessor 113 (described in further detail below). The battery 138 is preferably a lithium-ion battery that is configured to be rechargeable, but can be any appropriate rechargeable battery (e.g., nickel-cadmium, nickel metal hydride, or lithium-ion polymer). Alternatively, the battery 138 may not be a rechargeable battery. Preferably, the battery 138 is configured to have a profile with a low aspect ratio, contributing to a thin form factor of the microsensor patch 110. However, the battery 138 can be configured to have any appropriate profile such that the battery 130 provides adequate power characteristics (e.g., cycle life, charging time, discharge time, etc.) for the system 100. In some variations, a thin-film battery can be integrated with the microsensor patch 110 in order to facilitate substantially continuous analyte detection by the system 100, independent of the microprocessor 113 and digital electronics of the electronics subsystem 120.

In embodiments where the battery 138 is rechargeable, the electronics subsystem 120 can also comprise a charging coil 140 that functions to provide inductive charging for the battery 138, and a charging detection module 39, in communication with the microprocessor 113, that enable detection of charging of the battery 138. The charging coil 140 is preferably coupled to the battery 138 and converts energy from an electromagnetic field (e.g., provided by an element of a base station, as described in further detail below), into electrical energy to charge the battery 138. Inductive charging provided by the charging coil 140 thus facilitates user mobility while interacting with the system 100. In alternative variations, however, the charging coil 140 can altogether be omitted (e.g., in embodiments without a rechargeable battery), or replaced by a connection configured to provide wired charging of a rechargeable battery.

Additionally or alternatively, in some variations, the microsensor patch 110 can comprise a semi-active or fully-active power cell (e.g., implementing microelectromechanical system elements) that functions to absorb and/or release generated energy from any one or more of: body heat of the user, body movement of the user (e.g., with piezoelectric elements, with capacitive elements), static voltage from the environment of the user, light in the environment of the user (e.g., using solar cells), magnetic energy flux, galvanic differentials, and any other suitable energy source to provide secondary backup energy for the system 100.

The impedance detection module 126 is in communication with the signal conditioning module 122 and the power management module 124, and functions to enable detection of a proper interface between the microsensor 116 and body fluid (e.g., interstitial fluid) of the user. In facilitating monitoring of impedance, the impedance detection module 126 can thus provide signals that indicate that the microsensor patch 110 is properly coupled to the user (e.g., interfacing with interstitial fluid and experiencing an ~80% moisture environment) or improperly coupled to the user (e.g., not interfacing properly with interstitial fluid and experiencing a low-moisture environment). Signals from the impedance detection module 126 can further be used to trigger an error correction action (e.g., notification for the user to reapply the microsensor patch 110, automatic manipulation of the microsensor patch 110 to re-establish interface with body fluid, etc.). In one variation, as shown in FIG. 4, the impedance detection module can comprise electronic circuitry configured to communicate with the multiplexer 22, the ADC 24, and the power management module 124, in receiving an impedance signal from the microsensor 116. However, the impedance detection module 126 can additionally or alternatively be configured relative to other elements of the electronics subsystem 120 in any other suitable manner.

Figure 7:
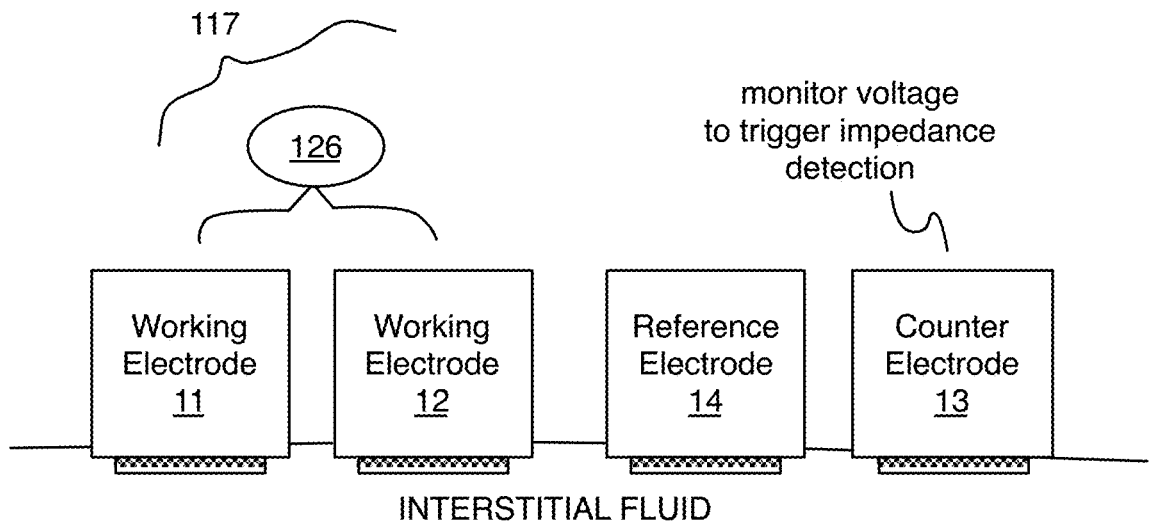
FIG. 7 depicts a variation of an impedance detection module in an embodiment of a system for monitoring body chemistry.

In generating the impedance signal, the impedance detection module 126 can be configured to detect impedance between two electrodes of the array of filaments 117 in response to an applied voltage provided in cooperation with the power management module 126 and the microprocessor 113. In one variation, wherein the microsensor 116 comprises a first working electrode 11, a second working electrode 12, a counter electrode 13, and a reference electrode, the impedance detection module 126 can be configured to detect impedance from two of the first working electrode 11, the second working electrode 12, the counter electrode 13, and the reference electrode 14, examples of which are shown in FIG. 7. In a specific example, an applied signal can be injected into the system in a working electrode and detected in the reference electrode 14. However in other configurations of the microsensor 116, the impedance detection module 126 can be configured to detect impedance from electrodes of the microsensor 116 in any other suitable manner.

Figure 8:
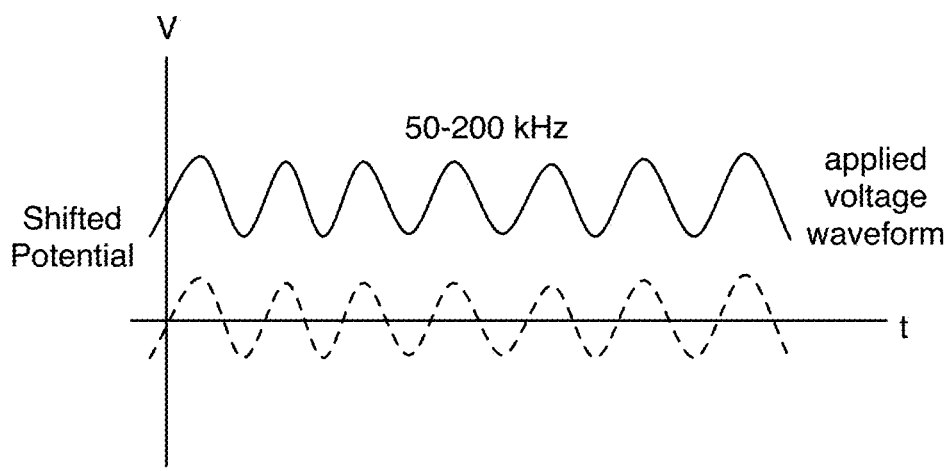
FIG. 8 depicts an example of an applied voltage waveform in an embodiment of a system for monitoring body chemistry.

In relation to the applied voltage used for generation and reception of the impedance signal (i.e., for purposes of perturbation), the electronics subsystem 120 is preferably configured to provide an applied voltage waveform having a characteristic value (e.g., average value) near the operating potential of the signal conditioning module 122 of the electronics subsystem 120. In a variation wherein the signal conditioning module 122 (e.g., an analog front end 23 of the signal conditioning module 122) operates at a shifted potential relative to a potential of an electrode of the microsensor 116 (e.g., a reference potential of a reference electrode), the applied voltage waveform preferably has a characteristic value (e.g., average value) near or equal to that of the shifted potential, in order to improve stability of the microsensor 110 when switching back to a current sensing mode (i.e., the primary detection mode). The offset (i.e., shifted potential) is configured to reduce or minimize any disruption to signal integrity when the microsensor 110 is switched from a current sensing mode to an impedance detection mode, and then back to a current sensing mode. In a specific example, as shown in FIG. 8, the applied voltage waveform is shifted about a characteristic value and has a frequency from 50-200 kHz, in relation to a shifted potential of the analog front end 23 relative to the reference electrode 14. However, the applied voltage can alternatively have any other suitable characteristics (e.g., characteristic voltage values, frequencies, etc.) defined in relation to the operating potential(s) of any other suitable element of the electronic subsystem 120 related to the microsensor 116.

In relation to triggering of a measurement using the impedance detection module 126, triggering can occur with any suitable frequency (e.g., in relation to the lifespan of usage of the system 100), any suitable regularity (e.g., at regular time intervals, at irregular time intervals, etc.), and/or upon any suitable triggering event. In one variation, the impedance detection module 126 can be configured to provide an impedance signal in association with monitoring of an electrode (e.g., monitoring voltage of the counter electrode 13) of the microsensor 116, wherein detection of an out-of-range parameter (e.g., voltage) of the electrode triggers the applied voltage waveform and generation of an impedance signal. As such, the electronics subsystem 120 and the processing subsystem 160 (described further below) can be configured to cooperate in continuously detecting a voltage parameter of the counter electrode 13, and the electronics subsystem 120 can be configured to apply the applied voltage waveform and detect the impedance signal when the voltage parameter of the counter electrode satisfies a voltage threshold condition.

Additionally or alternatively, in another variation, the impedance detection module 126 can be configured to provide an impedance signal upon initial application of the system 100 to the body of the user. Additionally or alternatively, in another variation, the impedance detection module 126 can be configured to provide impedance signals at regular time intervals (e.g., once every hour) over the course of use of the system 100 by the user. Additionally or alternatively, in relation to other sensors (e.g., of a mobile computing device associated with the user and the system 100, of a wearable computing device associated with the user and the system 100, of the system 100, etc.) the impedance detection module 126 can be configured to provide an impedance signal in response to a sensor signal that indicates performance of an action by the user. For instance, monitoring of signals provided by an accelerometer and/or gyroscope can be used to indicate that the user is exercising, and that an impedance measurement should be taken (e.g., during exercise, after exercise, etc.) to ensure proper coupling of the system 100 to the user. In another example, monitoring of body temperature of the user can be used to indicate that the user is showering, and that an impedance measurement should be to ensure proper coupling of the system 100 to the user. The impedance detection module 126 can, however, be configured in any other suitable manner.

The impedance detection module 126 can further be used to generate notifications pertaining to impedance signal measurements that indicate improper coupling. For instance, a notification can be generated (and transmitted to a mobile computing device of the user) in response to detection of unsuitable impedance derived from comparison between the impedance signal and an impedance threshold condition. However, use of the impedance signal in performing an error correction action can be performed in any other suitable manner.

The transmitting unit 130 functions to receive signals generated by the microsensor patch 110 (e.g., by way of the microprocessor 113), and to interface with at least one of a mobile computing device 150, a data processing and/or storage module (e.g., a module external to an on-board storage module, a cloud-based computing module, etc.) by outputting signals based on at least one analyte parameter. The transmitting unit 130 thus cooperates with other elements of the electronics subsystem 120 to transmit signals based on sensed analyte parameters, which can be used to facilitate analyses of the user's body chemistry. In variations, the transmitting unit 130 includes an antenna 132, a radio 134 coupling the antenna to the microprocessor 113, and can additionally or alternatively include a linking interface 136 (e.g., wireless or wired interface, as described in further detail below).

Preferably, the transmitting unit 130 and the microsensor patch 110 are integrated as a cohesive unit; however, the transmitting unit 130 and the microsensor patch 110 can alternatively form a modular unit, wherein one of the transmitting unit 130 and the microsensor patch 110 is disposable, and wherein one of the transmitting unit 130 and the microsensor patch 110 is reusable. In variations of the microsensor patch 110 and the transmitting unit 130, elements of the microsensor patch 110 aside from the microsensor 116 can alternatively be integrated with the transmitting unit 130, such that the transmitting unit 130 is configured to be reusable and the microsensor 116 of the microsensor patch 110 is configured to be disposable. Modularity in the system 100 is described in further detail in relation to the housing 190 below.

Additionally, the transmitting unit 130 is preferably configured to output signals based on at least one analyte parameter characterizing body chemistry continuously over the lifetime usage of the transmitting unit 130; however, the transmitting unit 130 can alternatively be configured to output signals based on at least one analyte parameter at a set of time points (e.g., minutes, hours, days). Still alternatively, the transmitting unit 130 can be configured to output signals in a manner that does not interfere with other operations (e.g., signal collection operations) of the electronics subsystem 120. In one such example, the transmitting unit 130 can be configured to stop signal transmission whenever the ADC 24 is collecting signal data from the microsensor 116, in coordination with timing enabled by a clock/watchdog module associated with the microprocessor 113. In variations, the transmitting unit 130 can be further configured to output signals upon a user prompt, and/or can comprise a variable sampling rate. For example, the sampling rate can be lower when user is asleep, higher during activity (e.g., exercise), higher when there is a sudden change in a value, higher in response to other stimuli (e.g., if glucose spikes, sampling rate increases for all analytes).

The antenna 132 of the transmitting unit 130 functions to convert electrical signals from the microsensor patch 110 into radio waves, to facilitate communication with one or more devices external to the microsensor patch 110 and/or transmitting unit 130 assembly (e.g., by a Bluetooth Low Energy connection). The antenna 132 preferably interfaces with a radio 134 coupled to the microprocessor 113, as shown in FIG. 4, but can additionally or alternatively interface with other elements of the transmitting unit 130. The antenna is preferably an omnidirectional antenna that radiates radio wave power uniformly primarily in one plane, with the power decreasing with elevation angle relative to the plane; however, the antenna can alternatively be an isotropic antenna that has a spherical radiation pattern. Other variations of the antenna can include any appropriate antenna that can be integrated with the form factor of the transmitting unit, while providing appropriate communication with external devices.

Because the system 100 can transmit in configurations where the system 100 is proximal/near/coupled to the body of the user, the antenna 132 can be configured, with other components of the transmitting unit 130, in order to promote undisrupted signal transmission due to signal interactions with the body of the user. For instance, one or more of the following can be implemented: the antenna 132 can be decoupled from the ground plane of the printed circuit board of the electronics subsystem, the antenna 132 can be positioned near an edge region of the housing 190 described below, the antenna/transmitting unit 130 can have a configuration of DC coupling to skin of the user (e.g., thereby providing an offset and using the body of the user as an RF ground), and any other suitable antenna design can be implemented to reduce signal disruption.

The radio 134 functions to transmit and receive signals from the antenna 132, and also facilitates communication with elements of the transmitting unit 130 and external devices. The radio 134 and the antenna 132 can additionally or alternatively be supplemented with a linking interface 136, as described in further detail below, but can additionally or alternatively interface with other elements of the electronics subsystem 120.

The linking interface 136 functions to transmit an output of at least one element of the microsensor patch 110/ transmitting unit 130 assembly to a mobile computing device 150. Additionally, the linking interface 136 can function to transmit and output of at least one element of the microsensor patch 110 and transmitting unit 130 assembly to another element external to the microsensor patch 110 and transmitting unit 130. Preferably, the linking interface 136 is a wireless interface; however, the linking interface 136 can alternatively be a wired connection. In a first variation, the linking interface 136 can include a first module that interfaces with a second module included in a mobile computing device 150 or other external element (e.g., wrist-borne mobile computing device, head-mounted mobile computing device), wherein data or signals (e.g., microsensor or transceiver outputs) are transmitted from the transmitting unit 130 to the mobile computing device 150 or external element over non-wired communications. The linking interface 136 of the first variation can alternatively implement other types of wireless communications, such as 3G, 4G, radio, or Wi-Fi communication. In the first variation, data and/or signals are preferably encrypted before being transmitted by the linking interface 136. For example, cryptographic protocols such as Diffie-Hellman key exchange, Wireless Transport Layer Security (WTLS), or any other suitable type of protocol can be used. The data encryption can also comply with standards such as the Data Encryption Standard (DES), Triple Data Encryption Standard (3-DES), or Advanced Encryption Standard (AES). In variations with data encryption, data can be unencrypted upon transmission to the mobile computing device 150 associated with the user. However, in an alternative variation, data can remain encrypted throughout transmission to a mobile computing device (associated with the user, not associated with the user) and unencrypted at another module of a processing subsystem 160 (e.g., unencrypted in the cloud), wherein information derived from analysis of the data can then be transmitted back to the mobile computing device associated with the user in a secure manner. In this variation, a user can thus pair his/her microsensor patch 10 with a mobile computing device unassociated with the user for transmission of encrypted data, and then later receive personalized body information at his/her own mobile computing device 150 after processing in the cloud.

In a second variation, the linking interface 136 is a wired connection, wherein the linking interface 136 includes a wired jack connector (e.g., a ⅛" headphone jack, a USB connection, a mini-USB connection, a lightning cable connection, etc.) such that the transmitting unit 130 can communicate with the mobile computing device 150 and/or an external element through a complementary jack of the mobile device and/or external element. In one specific example of the linking interface 136 that includes a wired jack, the linking interface is configured only to transmit output signals from the transmitting unit 130/microsensor patch 110. In another specific example, the linking interface 136 is configured to transmit data to and from at least one element of transmitting unit 130/transdermal path 110 assembly and a mobile computing device 150. In this example, the linking interface 136 can transmit output signals into the mobile computing device 150 through an input of the jack of the mobile computing device 150 and can retrieve data from an output of the jack of the mobile computing device 150. In this example, the linking interface 136 can communicate with the mobile computing device 150 via inter-integrated circuit communication (I2C), one-wire, master-slave, or any other suitable communication protocol. However, the linking interface can transmit data in any other way and can include any other type of wired connection that supports data transfer between the transmitting unit 130 and/or microsensor patch 110, and the mobile computing device 150.

Figure 25:
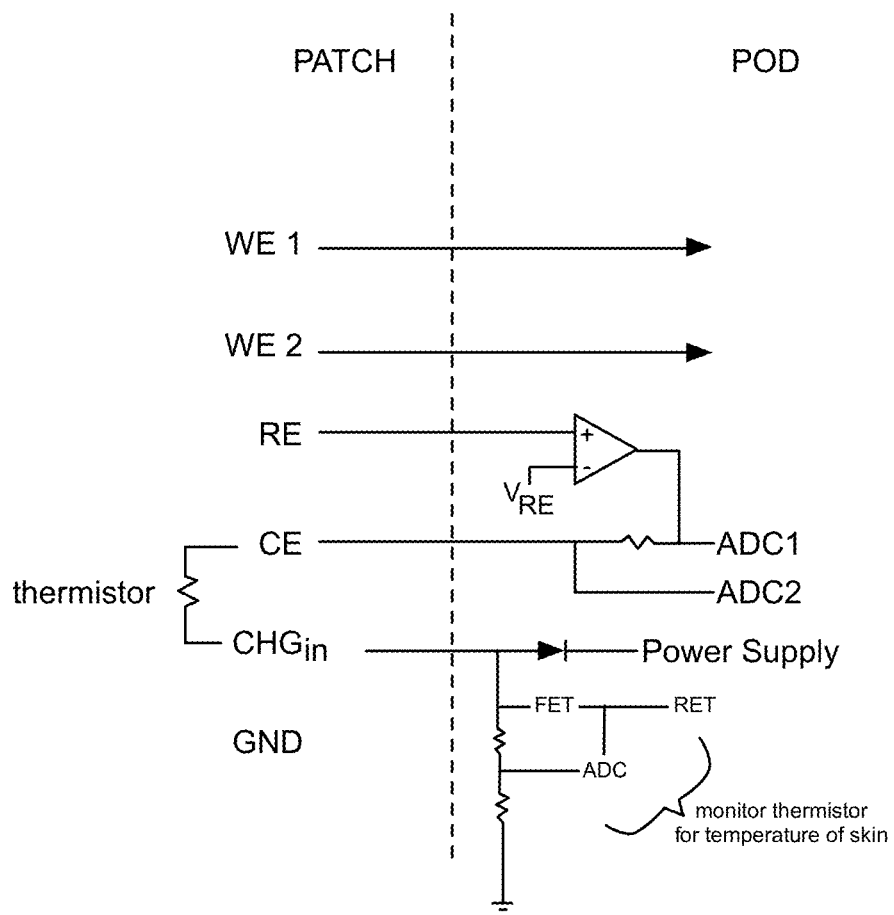
FIG. 25 depicts an example of a portion of an electronics subsystem in a system for monitoring body chemistry.

The electronics subsystem 120 can further include a thermistor/potentiostat component 20, which functions to enable temperature monitoring of skin of the user, in order to improve signal processing by accounting for thermal fluctuations of the body of the user. The thermistor/potentiostat component 20 can further function to enable detection of proper application of the system 100 at the body of the user, based upon monitoring of the temperature of the body of the user. As shown in FIG. 25, in one variation, the thermistor/potentiostat component 20 can interface components of the microsensor 116/first housing portion (e.g., patch coupled to the user) and components of the second housing portion 196 (e.g., pod for signal acquisition and transmission). However, variations of the thermistor/potentiostat component 20 can additionally or alternatively be configured in any other suitable manner. For instance, measurement of temperature using the thermistor/potentiostat component 20 can be additionally or alternatively used to assist with measurement of analyte readings (e.g., glucose readings), in relation to other biological or physiological phenomena of the user (e.g., fertility, fever, diurnal variations in temperature, etc.).

As noted above, the electronics subsystem 120 can include any other suitable module(s) and/or be configured in any other suitable manner. For instance, the electronics subsystem 120 can include or be in communication with an actuator configured to automatically perform an action (e.g., vibration, provision of a biasing force) that biases the microsensor into communication with interstitial fluid of the user, in response to detection of unsuitable impedance derived from comparison between an impedance signal and an impedance threshold condition.

1.1.3 System—Housing

The housing 190 supports the microsensor 116 and the electronics subsystem 120, and functions to facilitate robust coupling of the microsensor patch 110 to the user in a manner that allows the user to wear the microsensor patch 110 for a sufficient period of time (e.g., one week, one month, etc.). The housing 190 can also function to protect elements of the microsensor patch 110 from physical damage over the lifetime usage of the microsensor patch 110. Preferably, at least one portion of the housing 190 is flexible to facilitate adhesion to the user and compliance with skin of the user as the user moves in his/her daily life; however, at least a portion of the housing 190 can alternatively be rigid in order to provide more robust protection against physical damage. In an embodiment where a portion of the housing 190 is flexible, other elements of the microsensor patch 110 can also be flexible (e.g., using a thin film battery, using flexible electronics, etc.) to facilitate adhesion to the user and compliance as the user moves about in his/her daily life. In one variation, the housing 190 can comprise a single unit that entirely houses the microsensor 116 and the electronics subsystem 120. In this variation, the housing 190 can be configured to couple to the user using any suitable coupling mechanism (e.g., adhesive coupling mechanism, strap-based coupling mechanism, etc.). However, in other variations, the housing 190 can alternatively be modular and comprise a set of portions, each portion configured to enable coupling of the microsensor 116 to the user and/or to house elements of the electronics subsystem 120. Modularity of the housing 190 can thus allow portions of the system 100 to be disposable and/or reusable.

In some variations, modularity of the housing 190 can include housing components that are configured to break or otherwise prevent future recoupling after separation. For instance, with multiple housing portions, the system 100 can comprise coupled operation modes, wherein the multiple housing portions are coupled together during use (e.g., body chemistry monitoring), but once the system needs to be decoupled from the user and/or the housing portions need to be decoupled from each other (e.g., for charging of a module of the system, etc.), one or more of the multiple housing portions can break in a way that prevents re-coupling. In a first example, microsensor-supporting portions of the housing 190 can be configured to break apart (e.g., an opening of a first housing portion can comprise a perforation or other stress concentration region operable to break apart) after other electronics/power management/signal transmission components of the system 100 are separated from the microsensor-supporting portions of the housing 190. However, the system 100 can additionally or alternatively be configured in any other suitable manner in relation to modularity/reusability.

Figure 9:
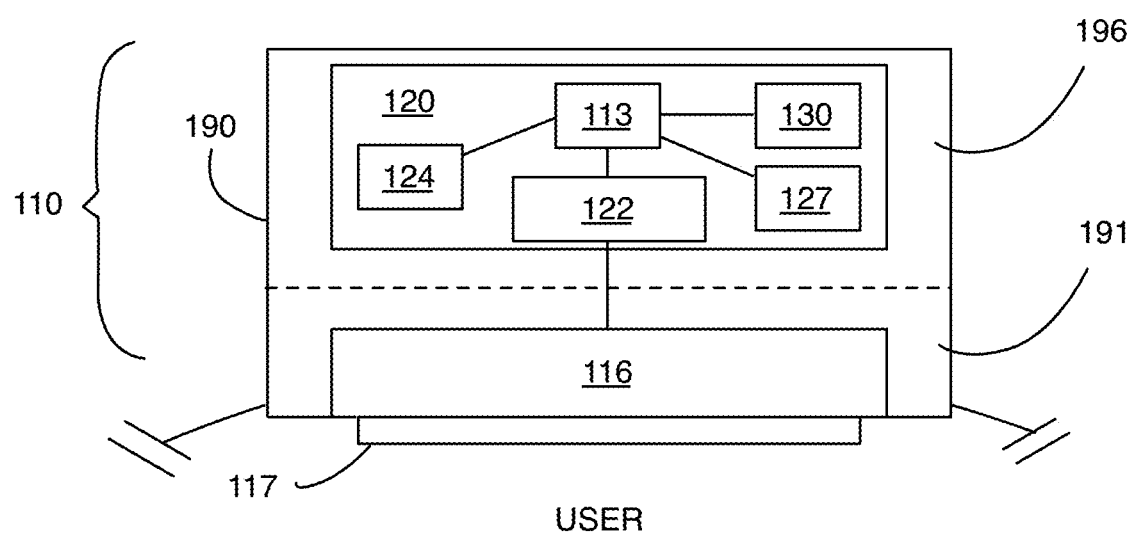
FIG. 9 depicts a variation of a housing in an embodiment of a system for monitoring body chemistry.
Figure 10A:
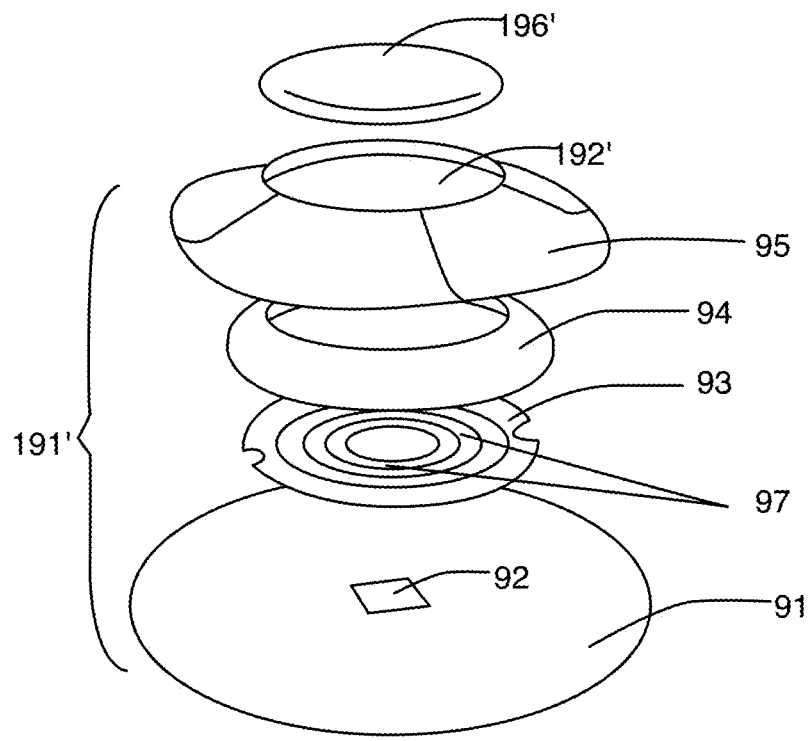
FIGS. 10A-10B depict specific examples of a housing in an embodiment of a system for monitoring body chemistry.
Figure 10B:
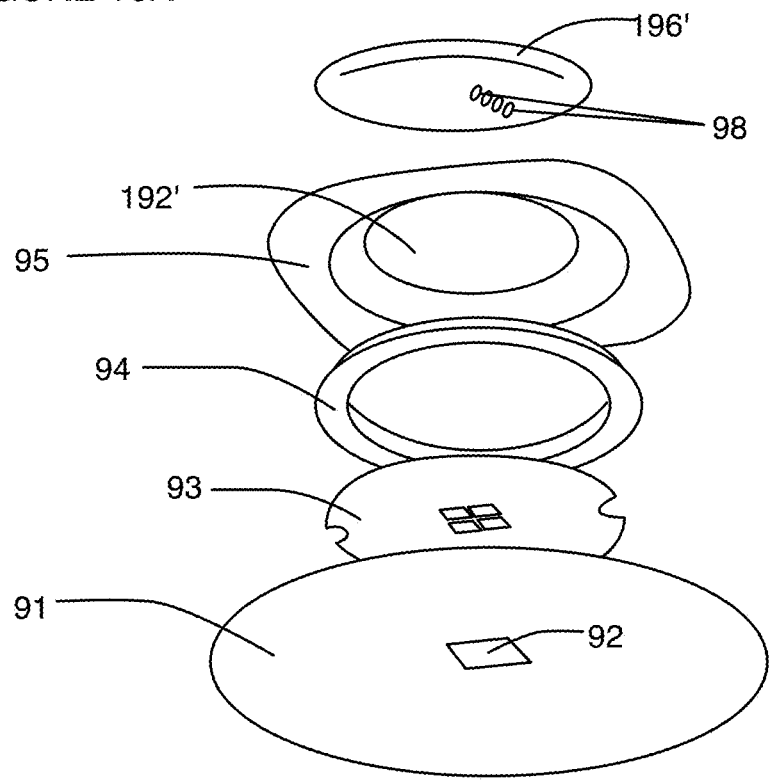
Figure 10C:
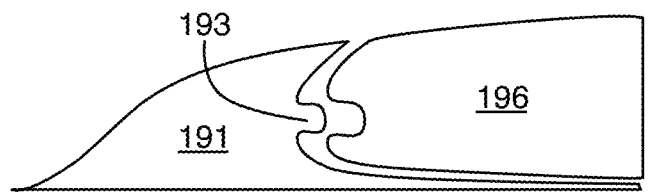
FIG. 10C depicts a specific portion of a housing in an embodiment of a system for monitoring body chemistry.

In one modular variation of the housing 190, as shown in FIG. 9, the housing can comprise a first housing portion 191 and a second housing portion 196, wherein the first housing portion 191 is configured to facilitate coupling of filaments of the microsensor 116 to the user, and the second housing portion 196 is configured to house elements of the electronics subsystem 120 and to couple the electronics subsystem 120 to the microsensor 116 by way of the first housing portion 191. As such, the first housing portion 191 and the second housing portion 196 of this variation are preferably configured to mate with each other in a complementary manner (e.g., with a male-female coupling mechanism, with a magnetic coupling mechanism, with a latch-based coupling mechanism, with a lock-and-key based coupling mechanism, etc.). In a specific example, as shown in FIGS. 10A-10B, the first housing portion 191' includes an opening 192', and a second housing portion 196' is insertable into the opening of the first housing portion in a first configuration, wherein coupling between the first housing portion 191' and the second housing portion 196' provides a hermetic seal between the first housing portion 191 and the second housing portion 196 (e.g., in a manner that prevents water or other fluids from passing into a region between the second housing portion 196 and the first housing portion 191). In more detail, as shown in FIG. 10C, the first housing portion 191 can include an o-ring 193 (e.g., an o-ring co-molded onto the material of the first housing portion) at a perimeter of the opening 192, and a perimeter region of the second housing portion 196 can include a recessed region 197 that interfaces with the o-ring 193 in a manner that provides a hermetic seal. As such, the o-ring 193 can be physically coextensive with the material of the first housing portion 191 near the opening 192 in order to facilitate coupling between the first housing portion 191 and the second housing portion 196. Alternatively, the o-ring 193 can be physically coextensive (e.g., go-molded) on material of the second housing portion) at a region configured to interface with the opening 192, or can be coupled to one or more of the first housing portion 191 and the second housing portion 196 in any other suitable manner.

Figure 10D:
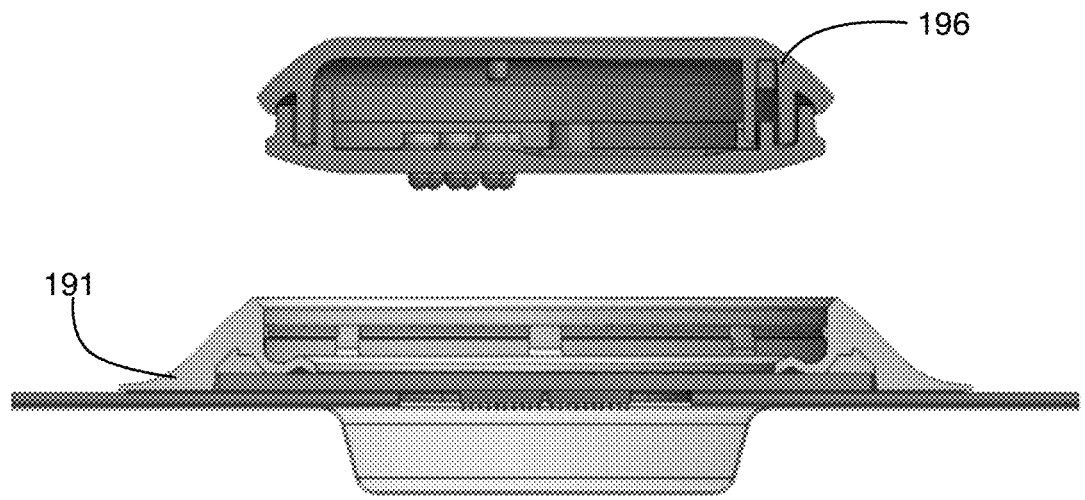
FIGS. 10D and 10E depict specific portions of a housing in an embodiment of a system for monitoring body chemistry.
Figure 10E:
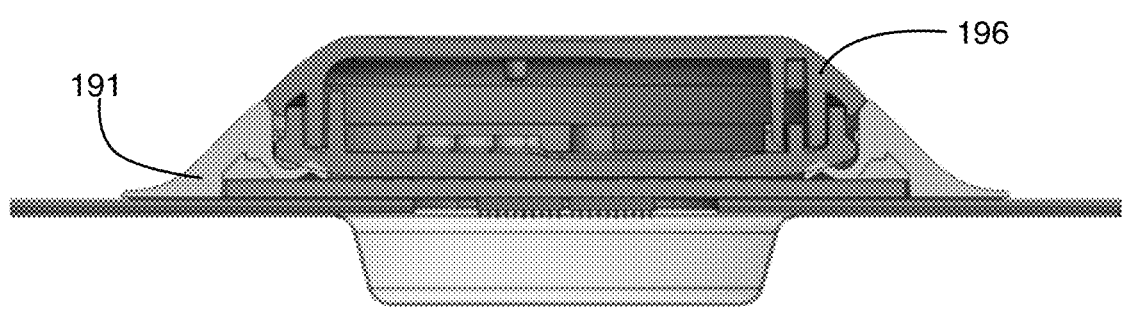

In an alternative example, as shown in FIGS. 10D and 10E, the second housing portion 196 can include an o-ring 193 internal to the outer diameter of the second housing portion 196, wherein the second housing portion 196 is configured in a manner that produces a crush seal when the second housing portion 196 is inserted into the opening of the first housing portion 191 (e.g., as in FIG. 10E). In this example, the first housing portion 191 can thus be manufactured (e.g., molded) without undercuts, in order to facilitate manufacturability with respect to reduced tooling complexity and cycle time.

Additionally or alternatively, the interface between the first housing portion 191 and the second housing portion 196 can be sealed using a covering 96 that adequately spans the interface/opening 192 between the first housing portion 191 and the second housing portion 196, in order to prevent water or any other undesired material from entering the interface. In variations, the covering 96 can be flexible or rigid, and can be comprised of any suitable material or composite of materials. Furthermore, the covering 96 can be coupled to one or more of the first housing portion 191 and the second housing portion 196 using an adhesive coupling mechanism or any other suitable coupling mechanics that promotes sealing of the opening/interface. In a specific example, the system 100 can include a covering 96 comprising a flexible polymer layer that is coupled to surfaces of both the first housing portion 191 and the second housing portion 196 proximal the opening 192, wherein the flexible polymer layer is coupled to the housing portions with an adhesive backing. However, variations of the covering 96 can be configured in any other suitable manner, or some variations of the system 100 can entirely omit a covering 96.

Figure 26A:
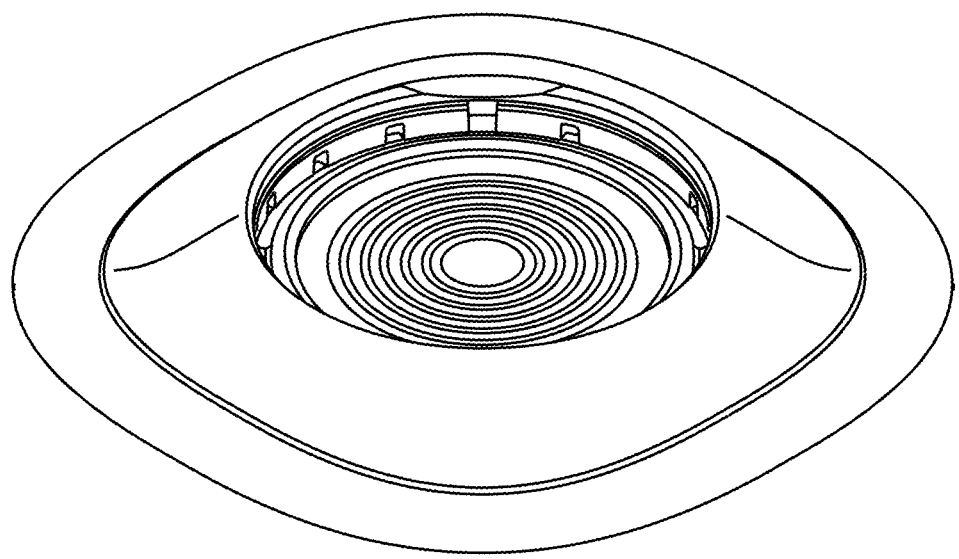
FIGS. 26A and 26B depict an example of a portion of a system for monitoring body chemistry.
Figure 26B:
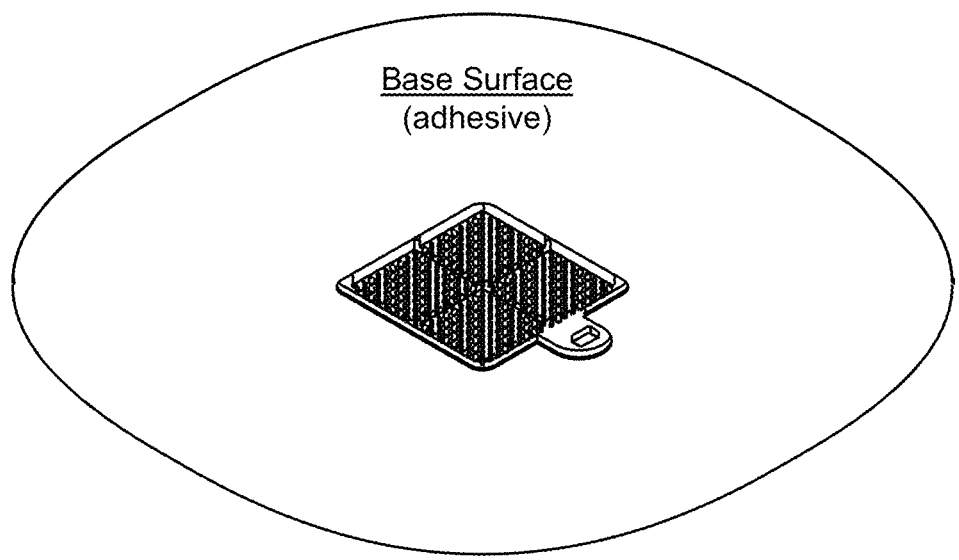

The first housing portion 191 preferably exposes the microsensor 116 through a base surface of the first housing portion 191, an example of which is shown in FIGS. 26A and 26B, such that portions of the microsensor 116 for accessing body fluid of the user are exposed at the base surface of the first housing portion 191. In a first variation, only microsensor filament portions operable to penetrate the body of the user may be exposed through the base surface of the first housing portion 191. In another variation, the entire microsensor 116, including portions that do not penetrate the body of the user can be exposed at the base surface of the first housing portion. However, portions of the microsensor 116 can be exposed through the base surface of the first housing portion 191 in any other suitable manner. In variations wherein at least a portion of the microsensor 116 is exposed at the base surface of the first housing portion 191, the system 100 can include a cap that is temporarily coupled to the base surface, wherein the cap protects the microsensor 116 from damage (e.g., in packaging, during shipping, etc.).

The first housing portion 191 can additionally or alternatively include an adhesive substrate 91 that substantially surrounds the microsensor 116 and is coupled to the base surface of the first housing portion 191, wherein the adhesive substrate 91 facilitates coupling of the first housing portion to the user and facilitates retention of a state of coupling between the microsensor 116 and the user after portions of the microsensor have been inserted into the user's body.

Figure 27:
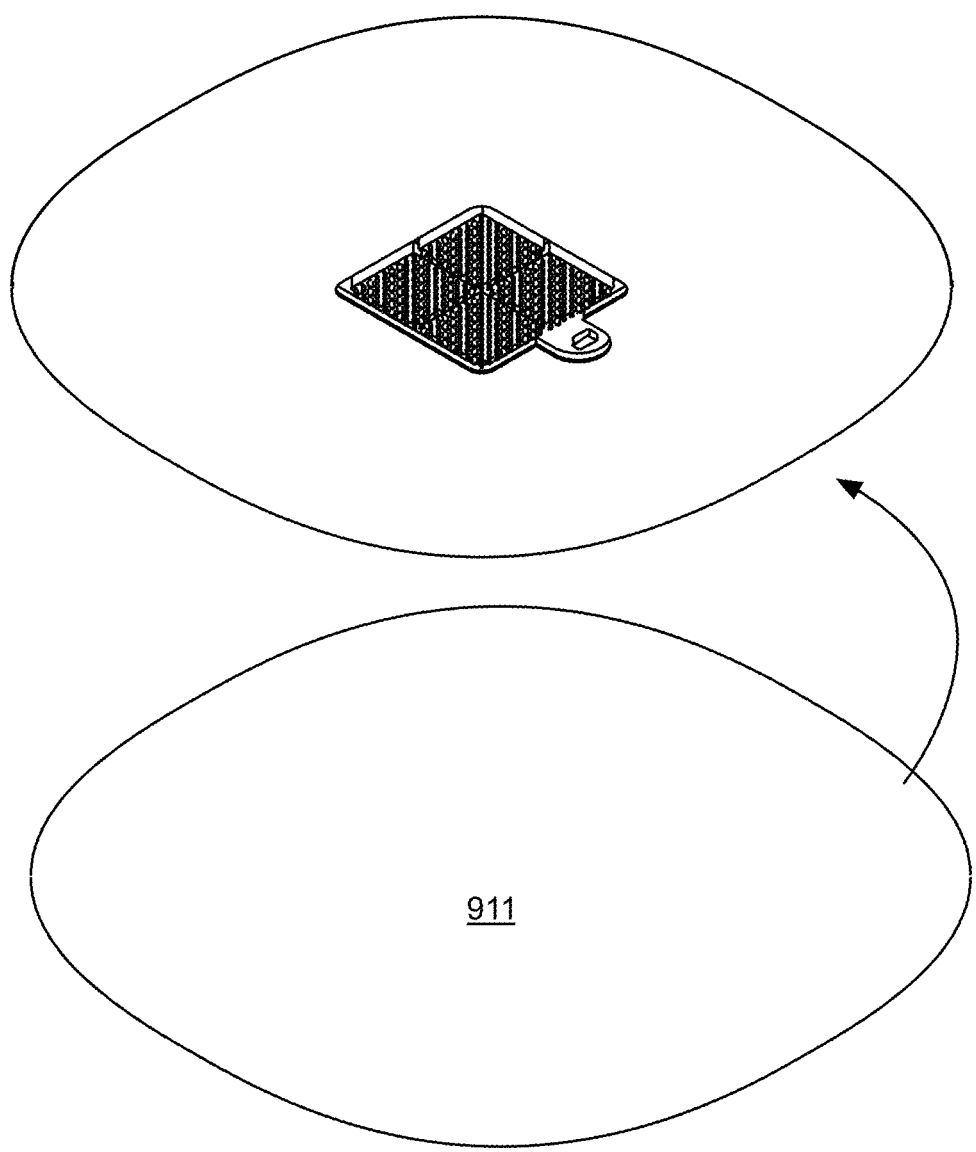
FIG. 27 depicts an example of a liner in an embodiment of a system for monitoring body chemistry.

Prior to application of the system 100 onto the user's body, the adhesive substrate 91 of the first housing portion 191 can be covered with or otherwise coupled to a liner 911, as shown in FIG. 27, wherein the liner 911 prevents the adhesive substrate 91 from prematurely sticking to objects and/or prevents the adhesive substrate 91 from losing its tack. The liner 911 can additionally or alternatively be designed to be easily separated from the adhesive substrate 91 by the user, such that removal of the liner 911 by the user does not interfere with application of the system 100 onto the body of the user. In some variations, the liner 911 can include multiple parts. For instance, the liner 911 can include overlapping or non-overlapping leaves, each leaf configured to be separated from the adhesive substrate 91 independently of the other leaves. Alternatively, the liner 911 can be a single liner designed to be separated from the adhesive substrate along a path that does not interfere with a process for applying the system 100 onto the body of the user. The liner 911 is preferably configured to be separated in a central-to-peripheral direction, in relation to the adhesive substrate 91. In another variation, the liner 911 can be configured to be separated in a peripheral-to-central direction in relation to the adhesive substrate 91. However, in still other variations, the liner 911 can be configured to be released from the adhesive substrate 91 in any other suitable direction or along any other suitable path.

Figure 28A:
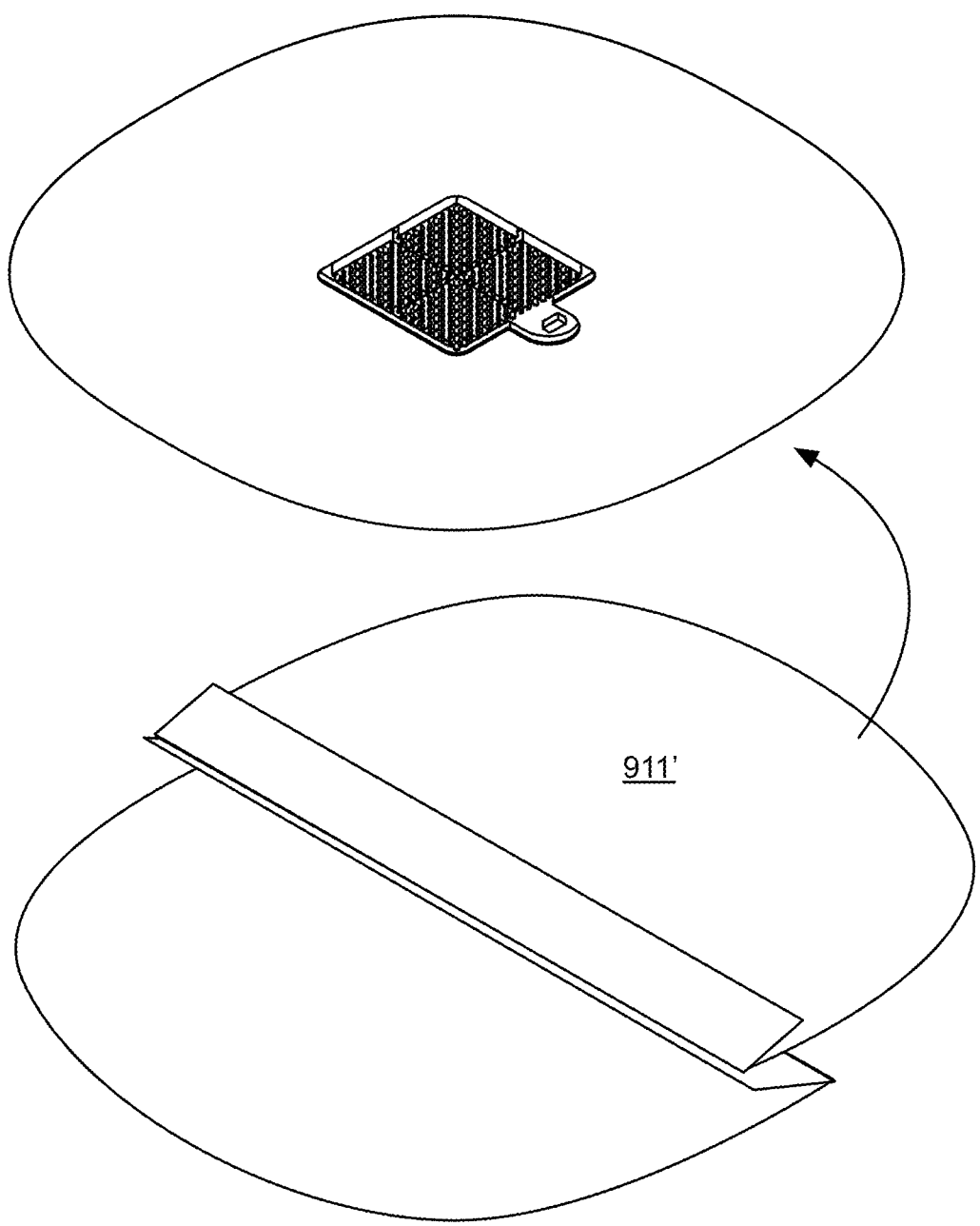
FIGS. 28A-28B depict examples of liners in an embodiment of a system for monitoring body chemistry.

In a first example, as shown in FIG. 28A, the liner 911' includes two overlapping leaves, wherein the two overlapping leaves includes 1) a first leaf spanning a first portion of the adhesive substrate 91 and including a first valley fold configured to be used as a pull-tab, and 2) a second leaf spanning a second portion of the adhesive substrate 91 and including a second valley fold overlapping the first valley fold configured to be used as a pull-tab. As such, in this example, each of the first leaf and the second leaf is configured to be pulled away in a central-to-peripheral direction in relation to the adhesive substrate 91. In relation to the cap described above, the first leaf and the second leaf can each include cutaways, such that the leaves do not touch exposed portions of the microsensor 116; however, the first leaf and the second leaf can alternatively be configured in any other suitable manner.

Figure 28B:
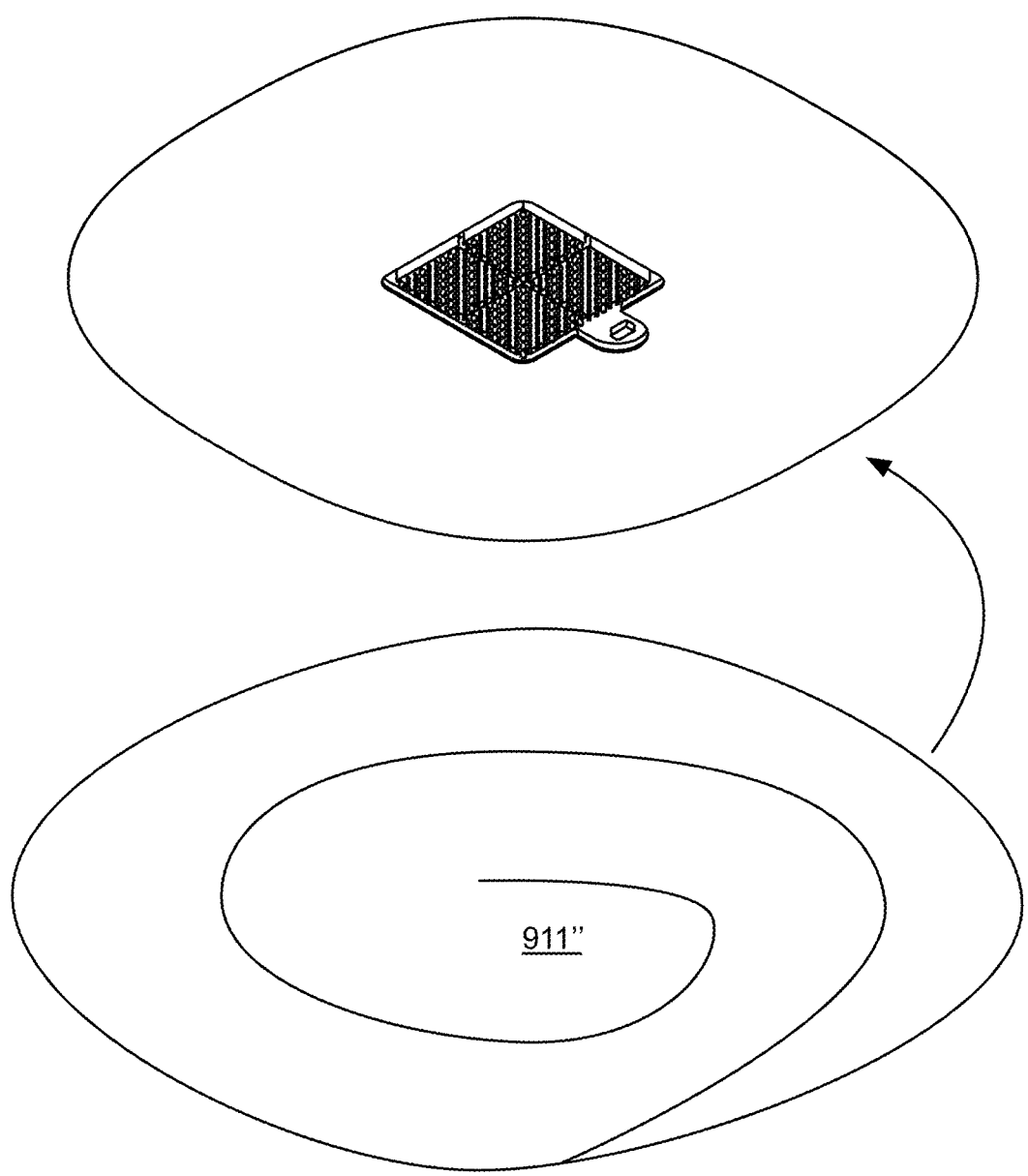

In a second example, as shown in FIG. 28B, the liner 911' can include a single liner having a spiral path initiating at a central region of the adhesive substrate and terminating at a peripheral region of the adhesive substrate, wherein the central region portion of the liner has a pull-tab to indicate that this is where separation should initiate. As such, in this example, the liner is configured to be pulled away in a central-to-peripheral direction in relation to the adhesive substrate 91. In relation to the cap described above, the liner can include a cutaway, such that the liner does not touch exposed portions of the microsensor 116; however, the liner can alternatively be configured in any other suitable manner.

The opening 192 of the first housing portion 191 and the second housing portion 196 can each have substantially circular footprints; however, the opening 192 and the second housing portion 196 can additionally or alternatively have any other suitable footprints or be configured in any other suitable manner.

In the specific example, as shown in FIGS. 10A-10B, the first housing portion 191' can comprise an adhesive substrate 91 having a microsensor opening 92, a microsensor interface substrate 93 superior to the adhesive substrate and configured to pass the microsensor 92 through the microsensor opening 92, a coupling ring 94 configured to retain the position of the microsensor interface substrate 93 relative to the adhesive substrate 91 and to provide an interface for mating with the second housing portion 196, and a flexible cover 95 ensheathing the coupling ring 94, coupled to the adhesive substrate 91, and configured to maintain coupling between the adhesive substrate 191, the microsensor interface substrate 93, and the coupling ring 94. In relation to the configuration described above, the adhesive substrate 91 is configured to facilitate adhesion of the microsensor patch 110 to the user at an inferior surface of the adhesive substrate, and the flexible cover 95 is configured to provide the opening 192' that receives the second housing portion 192.

The second housing portion 196 of the specific example is rigid, and configured to form a shell about the electronics subsystem 120, while including openings that provide access for a set of contacts 98 that interface the electronics subsystem 120 with the microsensor interface substrate 93 when the first housing portion 191 is coupled to the second housing portion 196. In relation to the microsensor interface substrate 93 of the first housing portion 191, and in relation to a circular (or otherwise axially symmetric) configuration of an interface between the second housing portion 196 and the opening 192 of the first housing portion 191, the microsensor interface substrate 93 of the specific example can include a circular printed circuit board comprising a set of concentric ring contacts 97, as shown in FIG. 10A, that interface electronics of the second housing portion 196 with filaments of the microsensor 116. As such, the set of contacts 98 (e.g., digital contacts) of electronics of the second housing portion 196 can properly interface with the microsensor 116 in any rotational position of the second housing portion 196 within the first housing portion 191, as shown in FIG. 10B. In alternative variations of this specific example however, orientation-unspecific coupling between the first housing portion 191 and the second housing portion 196 can be achieved in any other suitable manner. In still alternative variations of this specific example, the first housing portion 191 and the second housing portion 196 can be configured to couple with a set orientation in order to ensure proper communication between the microsensor 116 and the electronics subsystem 120.

Some variations of the housing 190 can additionally or alternatively include a coating that prevents water permeation (and/or other liquid permeation), but allows electrical contact (e.g., for current passage) to be made between the set of concentric ring contacts 97 of the first housing portion 191 and contacts 98 of the second housing portion 196. In variations, the coating can include a nanocoating of colloidal suspension of silicon oxide, which allows current passage through a waterproof layer that protects electronic components from shorting; however, the housing 190 can additionally or alternatively include any other suitable coating. For instance, waterproofing of electronics with coatings can additionally or alternatively be achieved using an adhesive coating (e.g., thin film) applied to circuit board components prior to assembly. Additionally or alternatively, the coating can include a nanocoating of another suitable material (e.g., paralene, etc.).

Furthermore, in relation to coupling between printed circuit board (PCB) components and components of either or both the first and the second housing portions 191, 196, coupling can be achieved using an adhesive process (e.g., using a glue or other adhesive). Additionally or alternatively, coupling can be achieved using a thermal process (e.g., a heat staking process) to couple PCB(s) to portions of the first housing portion 191 and/or the second housing portion 196.

In variations of the housing 190 comprising a first housing portion 191 and a second housing portion 196, the first housing portion 191 and the second housing portion 196 can be coupled together and/or coupled to the user by way of a applicator system 180, as described in further detail below. Furthermore, other variations of modularity can comprise any other suitable distribution of the microsensor 116 and elements of the electronics subsystem 120 across portions of the housing in any other suitable manner. For instance, in one such variation, the microsensor 116, the multiplexer 22, and the analog front end 93 of the electronics subsystem 120 can be coupled to a separate battery (e.g., a thin film battery) within a disposable portion of the housing 190, and other elements of the electronics subsystem 120 can be supported by a reusable portion of the housing 190. The system 100 can, however, comprise any other suitable distribution of elements across the housing 190 in a modular fashion.

1.2 System—Processing Subsystem

The processing subsystem 160 is in communication with the electronics subsystem 120 and functions to generate analyses pertaining to the user's body chemistry, and to transmit information derived from the analyses to the user at an electronic device associated with the user. As shown in FIG. 1, the processing subsystem 160 can be implemented in one or more of: a computer machine, a remote server, a cloud computing system, a microprocessor, processing hardware of a mobile computing device (e.g., smartphone, tablet, head-mounted mobile computing device, wrist-borne mobile computing device, etc.) and any other suitable processing system. In one variation, the processing subsystem 160 comprises a first module 161 configured to generate an analysis indicative of an analyte parameter of the user and derived from a signal stream from the microsensor 116 and an impedance signal from the electronics subsystem 120. Additionally, in this variation, the processing subsystem 160 comprises a second module 162 configured to render information derived from the analysis at an electronic device (e.g., mobile computing device 150) associated with the user, thereby facilitating monitoring of body chemistry of the user. In this variation, the modules of the processing subsystem 160 can be implemented in a hardware module and/or a software module. In variations, a software module 163 can be implemented, at least in part, as a native software application executing on a mobile computing device 150 associated with the user, wherein the user has a user account associated with the native software application.

In more detail, the software module 163 functions to analyze an output provided by the transmitting unit 130 of the electronics subsystem 120, and to communicate an analysis of the output back to the user, so that the user can monitor his/her body chemistry. Preferably, the software module 163 analyzes at least one analyte parameter in order to determine a metric providing information about a user's body chemistry. In one variation, the software module can determine that a body analyte parameter (e.g., glucose level) of the user is too low or less than ideal, and facilitate a behavior change in the user by providing a body chemistry metric indicating a hypoglycemic state. In this variation, the software module can additionally determine that the body analyte parameter (e.g., glucose level) of the user is within a proper range based on a determined metric. The software module of this variation can additionally determine that the body analyte parameter (e.g., glucose level) of the user is too high and facilitate a behavior change in the user by providing a body chemistry metric indicating a hyperglycemic state.

In another example, the software module can analyze an output provided by the transmitting unit 130 based on a set of parameters for multiple analytes characterizing a user's body chemistry, at a set of time points, and determine at least one metric based on the set of parameters at the set of time points. The software module can then determine and output at least one of a temporal trend in a metric, a temporal trend in an analyte parameter, absolute values of a metric, changes in value of a metric, absolute values of an analyte parameter, and changes in value of an analyte parameter. The software module 163 in this example can further be configured to communicate a suggestion to the user based on an analysis determined from the set of parameters for multiple analytes.

The software module preferably incorporates at least one of user health condition, user characteristics (e.g., age, gender, ethnicity), and user activity in analyzing an output provided by the transmitting unit 130. In one specific example, if a user sets a desired body glucose level range, which is entered into the software module, the software module can be configured to facilitate provision of alerts notifying the user of short-term risks (e.g., diabetic crash), long-term risks (e.g., worsening diabetic condition), and risk of exiting the desired body glucose level range. In another specific example, the software module can compare analyte parameters and/or a metric characterizing the user's body chemistry to other users with similar health conditions or characteristics (e.g., age, gender, ethnicity). In yet another example, the software module can be able to correlate at least one analyte parameter or metric to a user activity, such that the user is provided with information relating a value of the analyte parameter and/or metric to an activity that he or she has performed. The software module can additionally or alternatively provide an analysis that includes any other health- and/or user-related information that can be useful in treating, maintaining, and/or improving a health condition of a user.

Figure 11A:
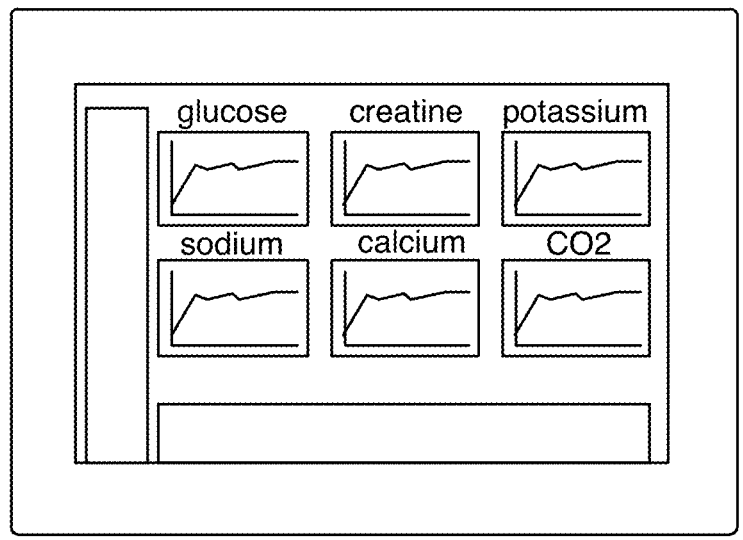
FIGS. 11A-11B depict examples of user interfaces implemented using a software module in an embodiment of a system for monitoring body chemistry.
Figure 11B:
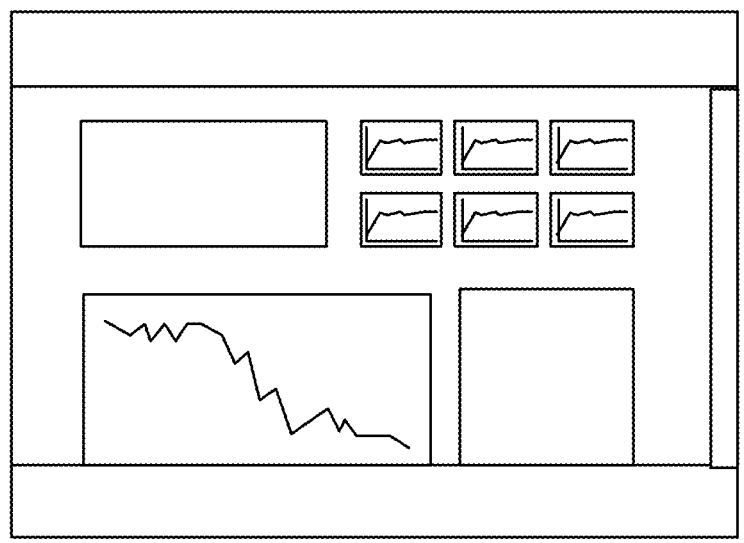

As shown in FIGS. 1, 11A, and 11B, the software module can be implemented, at least in part, as an application executable on a mobile computing device 150. As described above, the mobile computing device 150 is preferably a smartphone but can also be a tablet, laptop computer, PDA, e-book reader, head-mounted computing device, smartwatch, or any other mobile device. The software module can alternatively be an application executable on a desktop computer or web browser. The software module preferably includes an interface that accepts inputs from the user (e.g., user health condition, user characteristics, user activity), and uses these inputs in analyzing an output provided by the transmitting unit 130. Preferably, the software module also includes an interface that renders an analysis based on sensed analytes and/or user inputs in some form. In an example, the software module includes an interface that summarizes analyte parameter values in some manner (e.g., raw values, ranges, categories, changes), provides a trend (e.g., graph) in at least one analyte parameter or body chemistry metric, provides alerts or notifications, provides additional health metrics, and provides recommendations to modify or improve body chemistry and health metrics. In another example, the software module can implement two interfaces: a first interface accessible by a user, and a second interface accessible by a health care professional servicing the user. The second interface can provide summarized and detailed information for each user that the health care professional interacts with, and can further include a message client to facilitate interactions between multiple users and the health care professional. The software module can additionally or alternatively access a remote network or database containing health information of the user. The remote network can be a server associated with a hospital or a network of hospitals, a server associated with a health insurance agency or network of health insurance agencies, a server associated with a third party that manages health records, or any other user- or heath-related server or entity. The software module can additionally or alternatively be configured to accept inputs from another entity, such as a healthcare professional, related to the user.

The software module 163 can additionally or alternatively execute fully or in part on a remote server. In a first variation, the software module can be a cloud-computing-based application that performs data analysis, calculations, and other actions remotely from the mobile computing device 150. In one example of the first variation, the mobile computing device 150 can receive an output of the transmitting unit 130 via the linking interface 136 and then transfer the output to the remote server upon which the software module executes. In the first variation, signals are preferably transferred via a wireless connection, such as a Bluetooth connection, 3G or 4G cellular connection, and/or via a Wi-Fi internet connection. In another example of the first variation, a mobile computing device 150 can function to transmit data to and/or receive data from the software module. In a second variation, the software module can include a first software component executable on a mobile computing device 150, such as an application that manages collection, transmission, retrieval, and/or display of data. In the second variation, the software module can further include a second software component that executes on the remote server to retrieve data, analyze data, and/or manage transmission of an analysis back to the mobile computing device 150, wherein the first software component manages retrieval of data sent from the second software component and/or renders of a form of the analysis on a display of the mobile computing device 150. However, the software module can include any number of software components executable on any mobile computing device 150, computing device, and/or server and can be configured to perform any other function or combination of functions.

Figure 12A:
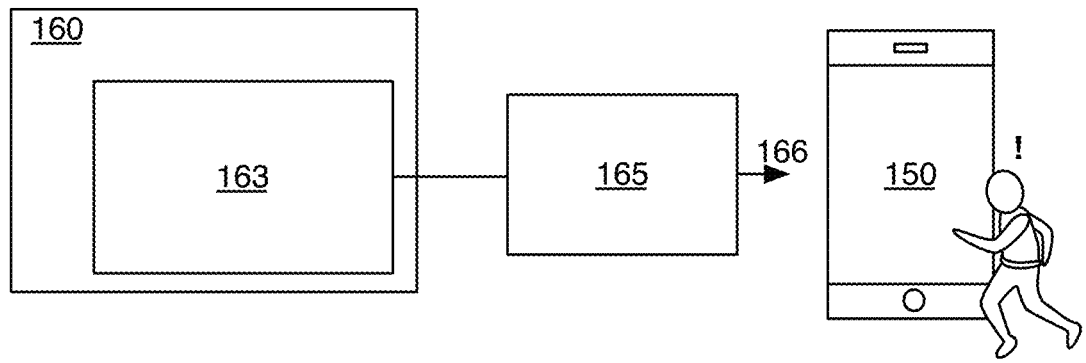
FIG. 12A depicts a notification module of an embodiment of a system for monitoring body chemistry.

As shown in FIG. 12A, the software module 163 can further be integrated with a notification module 165 configured to provide an alert or notification to a user and/or health care professional based on the analysis of the output. The notification module 165 functions to access an analysis provided by the software module and to control transmission of a notification 166 to at least one of a user and a healthcare profession interacting with the user. In one variation, the notification module 165 receives an analysis of the software module being executed on a mobile computing device 150, and generates a notification 166 based upon the analysis. In this variation, a form of the analysis is preferably transmitted from the software module, executing on the mobile computing device 150, to the notification module 165, wherein the mobile computing device 150 accesses the analysis either from the software module executing on the mobile computing device 150 or from the software module executing on a remote server and in communication with the mobile computing device 150. The notification module 165 preferably controls transmission of the notification 166 to the user, such as by triggering a display of the mobile computing device 150 to display a form of the notification, or by generating and/or transmitting an email, SMS, voicemail, social media platform (e.g., Facebook or Twitter) message, or any other message accessible by the user and which contains the notification 166. The notification module 165 can also convey the notification 166 by triggering a vibration of the mobile device 160, and/or by altering the state (i.e., ON or OFF) of one or more light sources (e.g., LEDs) of the mobile computing device 150. However, the notification module 165 can alternatively manage the transmission of any other information and function in any appropriate manner.

The notification 166 preferably contains information relevant to a body chemistry status of the user. The notification 166 can additionally include an explicit directive for the user to perform a certain action (e.g., eat, rest, or exercise) that affects the body chemistry of the user. Therefore, the notification 166 preferably systematically and repeatedly analyzes a body chemistry status of the user based on at least one analyte parameter of the user and provides and alert and/or advice to manage and monitor a user's body chemistry substantially in real time. In one example, the notification 166 can further include information related to what or how much to eat, where and how long to run, level of exertion, and/or how to rest and for how long in order to appropriately adjust body chemistry. In other examples, the notification 166 can include any appropriate information relevant to monitoring a body chemistry metric of the user.

Figure 12B:
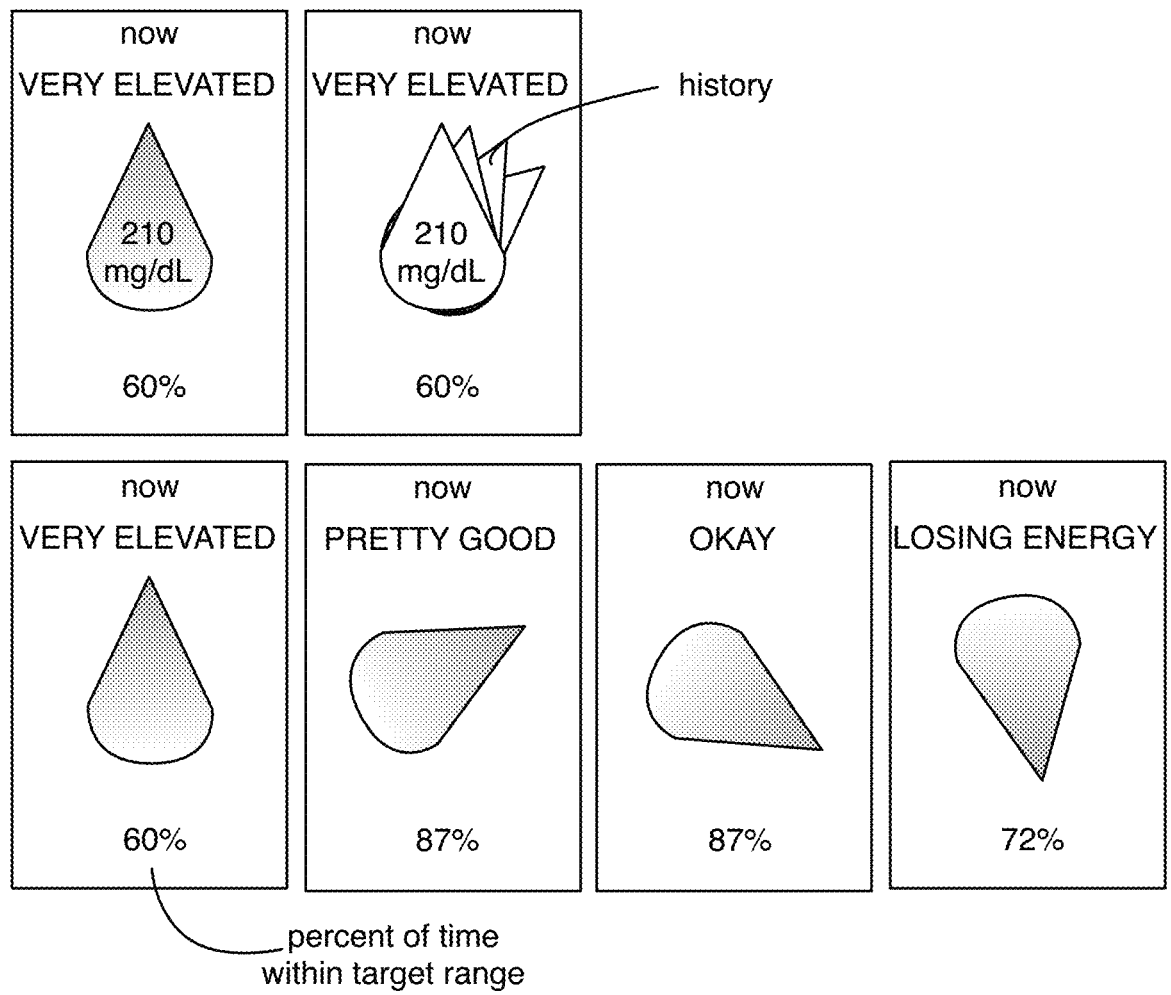
FIGS. 12B-12C depict specific examples of notifications in an embodiment of a system for monitoring body chemistry.

In still other examples, as shown in FIG. 12B, the notification 166 can indicate one or more of: a current level of a measured analyte (e.g., represented in hue, represented in saturation, represented in intensity, etc. of a graphical rendering); a trending direction for the level of the measured analyte (e.g., represented in a feature gradient within a graphical rendering); a lower bounding level and an upper bounding level between which the level of the measured analyte is traversing; a trending direction of a level of a measured analyte (e.g., represented in an arrow of a graphical rendering); a quantification of a level of a measured analyte (e.g., represented as rendered text); a summary of a level of a measured analyte (e.g., represented as rendered text); a percent of time within a time duration (e.g., one day) that the level of the measured analyte is within a target range (e.g., healthy range); and historical behavior of a level of a measured analyte (e.g., represented as historical "ghosting" of a rendering based upon a previous analyte level).

Figure 12C:
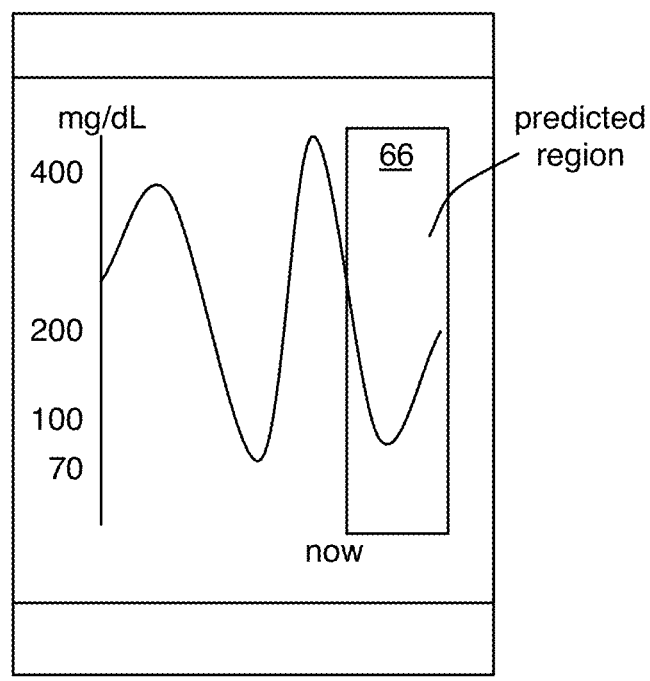

Additionally or alternatively, in still other examples, as shown in FIG. 12C, the notification 166 can include a graphical rendering that shows analyte data from past to present using a line graph representation, wherein an amount (e.g., concentration) of the analyte is represented along a first axis and time is represented along a second axis. In these examples, the graphical rendering can further include a "predicted region" based upon the analysis of the processing subsystem 160, wherein the predicted region 66 depicts a prediction of where the analyte level will be at a future time point, and a width of the predicted region 66 indicates confidence in the prediction.

Figure 13:
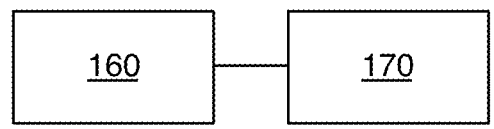
FIG. 13 depicts communication between a processing subsystem and a storage module in an embodiment of a system for monitoring body chemistry.

In relation to the processing subsystem 160 and analyses generated at the processing subsystem 160, the processing subsystem 160 can be coupled to or comprise a data storage unit 170, as shown in FIG. 13. The data storage unit 170 functions to retains data, such as an analysis provided by a software module, a notification 166, and/or any other output of any element of the system 100. The data storage unit 170 can be implemented with the microsensor patch 110, transmitting unit 130, mobile computing device 150, personal computer, web browser, external server (e.g., cloud), and/or local server, or any combination of the above, in a network configured to transmit, store, and receive data. Preferably, data from the data storage unit 170 is automatically transmitted to any appropriate external device continuously; however, data from the data storage unit 170 can alternatively be transmitted only semi-continuously (e.g., every minute, hourly, daily, or weekly). In one example, data generated by any element can be stored on a portion of the data storage unit 170 when the linking interface 136 is not coupled to an element external to the microsensor patch 110/transmitting unit 130 assembly. However, in the example, when a link is established between the linking interface 136 and an external element, data can then be automatically transmitted from the storage unit 170. In other examples, the data storage unit 170 can alternatively be prompted to transmit stored data by a user or other entity. Operation modes related to device pairing and information transfer are further described in relation to the base station of Section 1.4 below.

1.3 System—Applicator

Figure 14A:
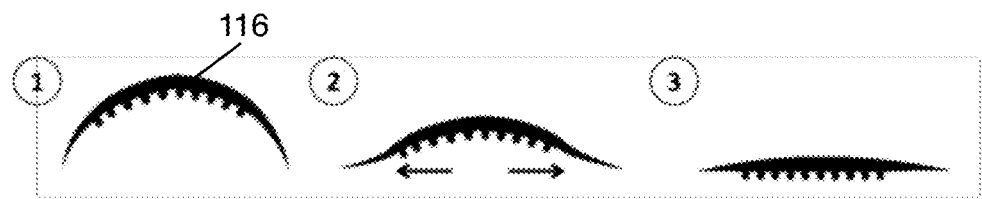
FIGS. 14A-14C depict examples of an arch application method and an end-to-end application method, respectively, in an embodiment of a system for monitoring body chemistry.
Figure 14B:
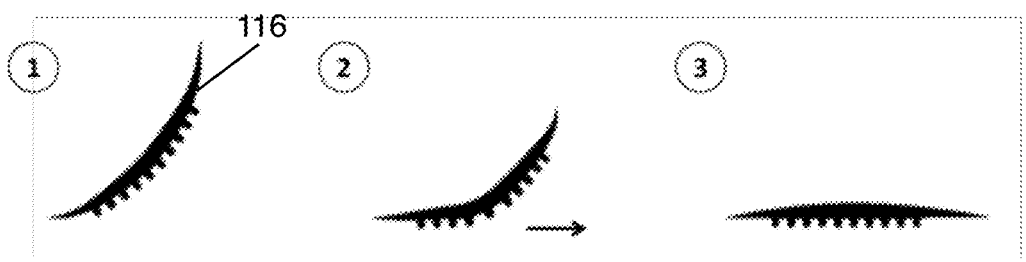
Figure 14C:
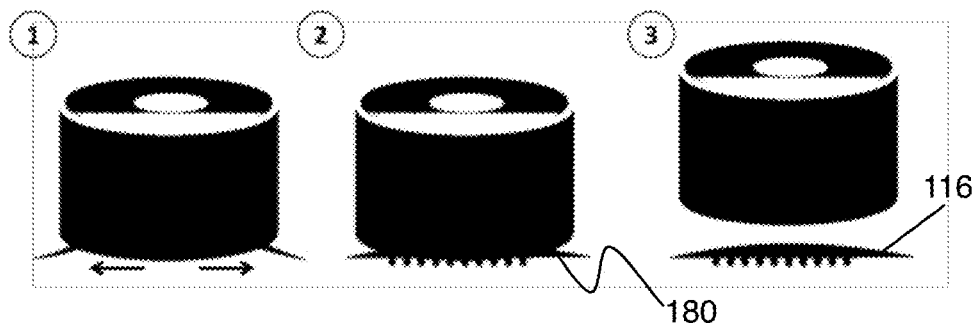

As shown in FIG. 1, the system 100 can further comprise a applicator system 180, which functions to facilitate application of at least one of the microsensor patch 110 and the transmitting unit 130 onto a body region of the user. The applicator system 180 preferably accelerates the a portion of the housing with the microsensor 116 toward skin of the user, thereby causing the microsensor 116 to penetrate skin of the user and sensing regions of the microsensor to access interstitial fluid of the user. However, the applicator system 180 can additionally or alternatively facilitate coupling of the microsensor 116 to the user using one or more of: skin stretching, skin permeabilization, skin abrasion, vibration, and/or any other suitable mechanism, variations of which are shown in FIGS. 14A-14C.

In variations, as shown in FIG. 15, the applicator system 180 can include a first applicator portion 81 comprising a coupling interface 811; a second applicator portion 82 comprising a retainer 821; an elastic coupler 83 between the first applicator portion 81 and the second applicator portion 82; and a trigger 84 operable between a loaded mode 84a and a released mode 84b; wherein, in the loaded mode, the elastic coupler is in a first compressed state between the first applicator portion and the second applicator portion, the first applicator portion is retained by the retainer of the second applicator portion, and the coupling interface is coupled to the second housing portion; and wherein, in the released mode, the elastic coupler is in a second compressed state (e.g., a state of lower compression or non-compression) between the first applicator portion and the second applicator portion, the first applicator portion is released from the retainer of the second applicator portion, and the coupling interface is uncoupled from the second housing portion, with the microsensor portions coupled to the user.

These variations of the applicator system 180 function to provide a mechanism that promotes proper application of the microsensor patch 110 at the body of the user. As such, these variations are configured for ease of use and/or error-preventing use in relation to one or more of: transitioning the applicator system into a loaded mode; initial positioning of the microsensor patch 110 at portions of the applicator system; positioning the applicator system 180 with the microsensor patch 110 at a body region prior to insertion of microsensor portions into the body; transitioning the applicator system from the loaded mode to the released mode, thereby properly inserting microsensor into the body of the user; and moving the applicator system 180 away from the body of the user.

1.3.1 Applicator—First Applicator Portion

The first applicator portion 81 functions to reversibly retain the microsensor patch 110 prior to coupling of the microsensor patch 110 to the user. The first applicator portion 81 can thus function to retain the microsensor patch as the microsensor patch is loaded and then accelerated toward the body of the user for microsensor insertion. Then, the first applicator portion 81 can release the microsensor patch 110 such that the microsensor patch 110 can be left at the body of the user.

As such, the first applicator portion 81 can include a coupling interface 811 that couples to one or more portions of the microsensor patch 110 prior to insertion. The coupling interface 811 can include: a suction interface operable to temporarily retain a surface of the microsensor patch 100 using negative pressure and by forming a temporary seal with the surface of the microsensor patch 100. Additionally or alternatively, the coupling interface 811 can interface with the microsensor patch 110 by any one or more of: an adhesive interface formed by an adhesive region of the first applicator portion and/or the microsensor patch 110; a magnetic interface between magnetic regions of the first applicator portion and the microsensor patch 110; a locking interface between the first applicator portion and the microsensor patch 110, a press-fit interface between the first applicator portion and the microsensor patch 110; and any other suitable interface between the first applicator portion and the microsensor patch.

The coupling interface 811 preferably couples to the second housing portion 196, which as described above, supports the electronics subsystem 120 and is insertable into an opening of the first housing portion 191. However, the coupling interface 81 can alternatively couple to the first housing portion 191 and/or to both the first housing portion 191 and the second housing portion. In a specific example, the coupling interface 811 comprises a suction interface that couples to a surface of the second housing portion 196 opposing a second surface of the second housing portion 196 that interfaces with electronics of the first housing portion 191; however, variations of the specific example can be configured in any other suitable manner.

Figure 16A:
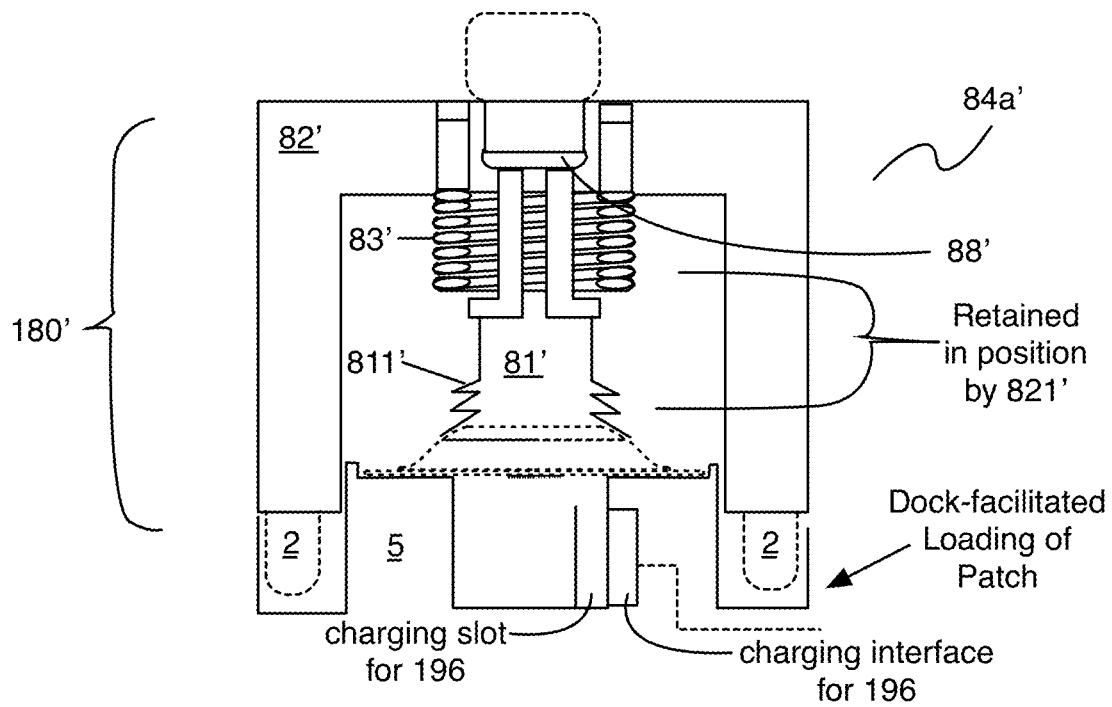
FIGS. 16A and 16B depict a first specific example of an applicator system in an embodiment of a system for monitoring body chemistry.
Figure 16B:
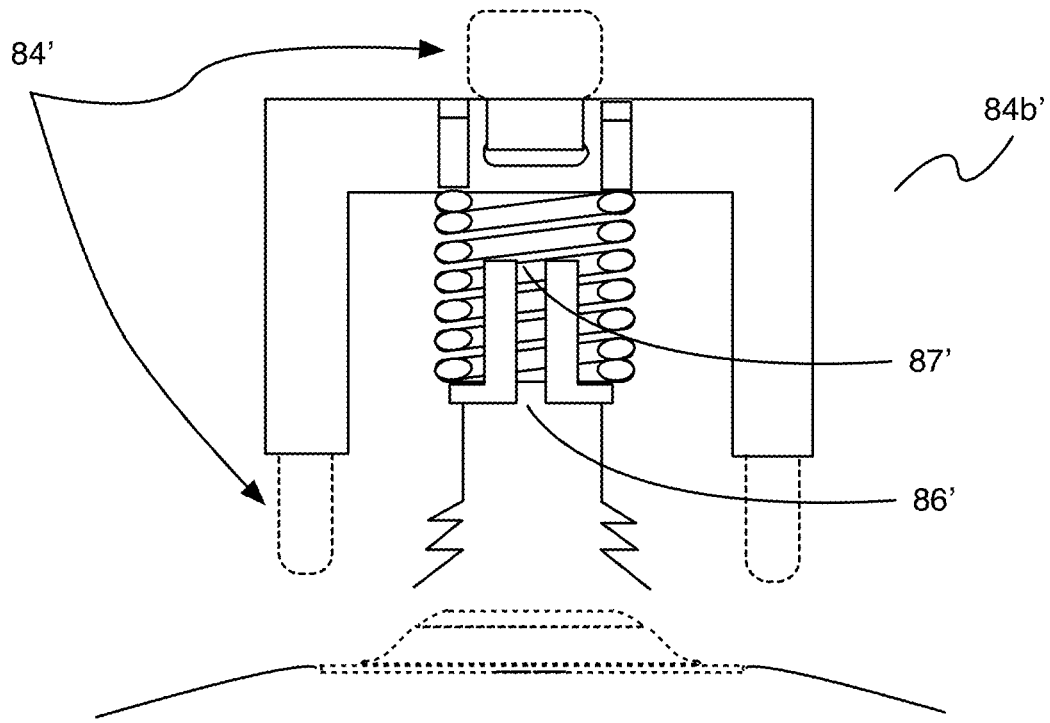

In variations of the coupling interface 811 including a suction interface, the coupling interface 811 can further include a venting channel having a first opening into a concave portion of the suction interface (that couples to the microsensor patch) and a second opening at a distal end. The venting channel facilitates release of the microsensor patch 110 from the applicator system 180 during and/or after acceleration of the microsensor patch toward the body of the user. The venting channel preferably has a shaft, an example of which is shown in FIGS. 16A and 16B, and a pathway through the shaft that connects the first opening to the second opening. As described below, the second opening of the venting channel preferably interfaces with a sealing interface at one or more of the second applicator portion 82 and the trigger 84 of the applicator system 180 in order to provide 1) a sealed state that supports coupling between the microsensor patch 110 and the applicator system 180 and 2) an unsealed state that supports uncoupling between the microsensor patch 110 and the applicator system 180. However, the venting channel 86 can alternatively be configured in any other suitable manner.

1.3.2 Applicator—Second Applicator Portion

The second applicator portion 82 functions to support the first applicator portion 81, the elastic coupler 83, and the trigger 84, and functions to cooperate with one or more portions of the applicator system 110 to reversibly lock the first applicator portion 81 into place and to release the first applicator portion 81 to accelerate a microsensor patch 110 coupled to the first applicator portion 81 along a path toward the body of the user. The second applicator portion 82 can thus circumscribe or otherwise surround the first applicator portion 81 in a manner that controls a path of motion of the first applicator portion 81 within the second applicator portion 82. However, any other suitable relationship can exist between the first applicator portion 81 and the second applicator portion 82, such that acceleration of the microsensor patch 110 toward the body of the user occurs as desired.

In relation to retention of the first applicator portion 81 (with the coupled microsensor patch 110) by the second applicator portion 82, the second applicator portion 82 can include or be coupled to a retainer 821 that provides a mechanism for reversibly locking the first housing portion 81 with the second housing portion 82 (e.g., during the loading mode described below).

The retainer 821 can include a mechanical latching mechanism, that, when engaged by the first housing portion 81, retains the position of the first housing portion in a loaded mode; then, with activation of the trigger 84 described below disengages the latching mechanism to release the first housing portion 81. In specific examples, the retainer can thus include one or more of: a wedge-shaped protrusion biased laterally toward a corresponding recessed region of the first housing portion 81, whereby the wedge-shaped protrusion engages the recessed region as the first housing portion 81 transitions into the loaded mode; a ram-and-catch mechanism whereby twisting of at least one of the second housing portion 82 and the first housing portion 81 engages a retaining region of the retainer 821; and any other suitable mechanical latching mechanism. In more detail, a ram-and-catch mechanism (or other twisting mechanism) can be used, in combination with a elastic component (as described below), to adjust the acceleration of the first applicator portion 81, with the microsensor patch 110, toward the body of the user. Such an adjustment can be based upon an amount of potential energy stored in a spring that is compressed by the rotation mechanism, or any other suitable mechanism, and can be used to ensure proper insertion of the microsensor for a variety of skin types or user demographics.

Figure 17A:
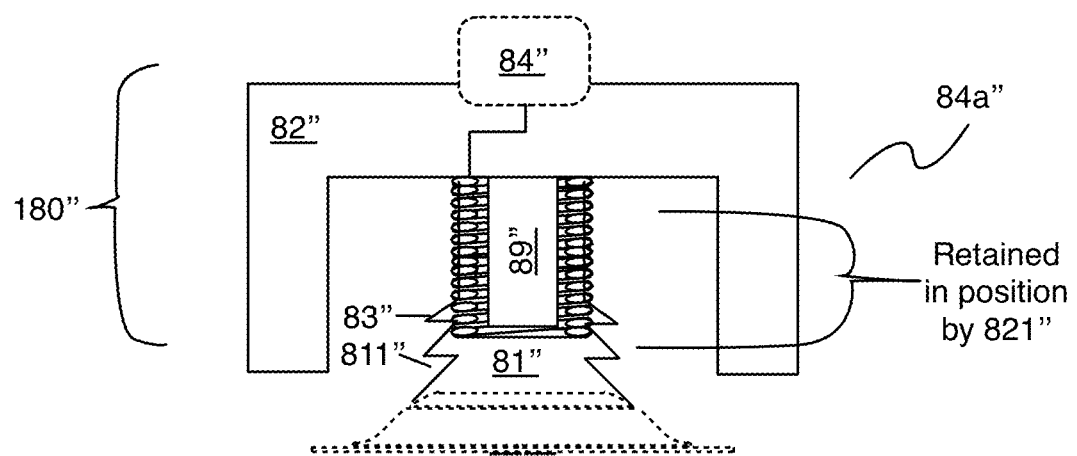
FIGS. 17A and 17B depict a second specific example of an applicator system in an embodiment of a system for monitoring body chemistry.
Figure 17B:
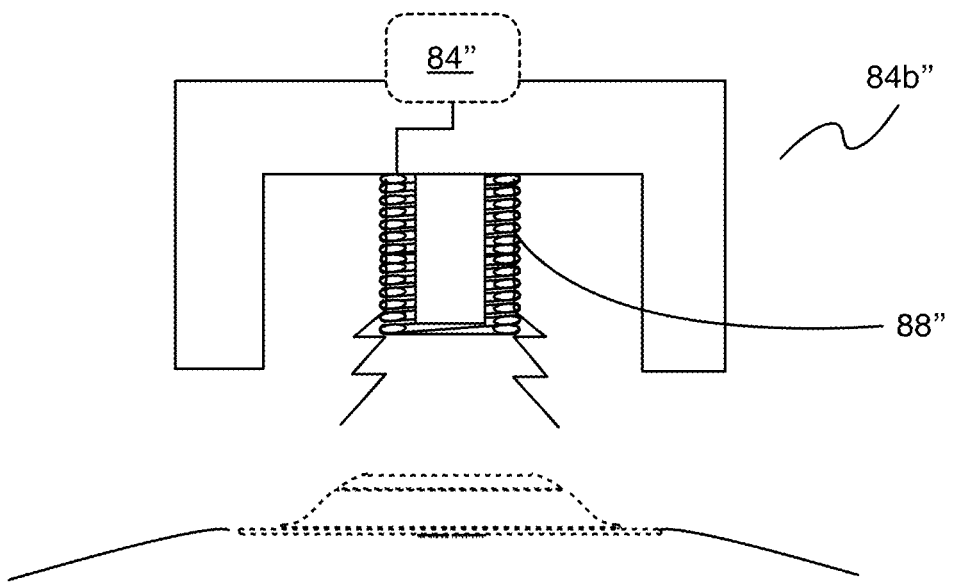

The retainer 821 can additionally or alternatively include a magnetic retention mechanism that reversibly retains a position of the first housing portion 81 relative to the second housing portion 82. The magnetic retention mechanism can include a magnet of a first polarity coupled to the second applicator portion 82 that interfaces with a magnet of a second polarity coupled to the first applicator portion 81, such that the two magnets provide a configuration that reversibly retains the first housing portion 81 in position relative to the second housing portion 82. Alternatively, at least one magnet of the magnetic retention mechanism can include an electromagnetic element. In a specific example, as shown in FIGS. 17A and 17B, the magnetic retention mechanism can interface with a coil element that passes current in a manner where the current magnitude affects an acceleration profile of the first housing portion 81, with the coupled microsensor patch 110, toward the body of the user. This mechanism is described in further detail in relation to the elastic coupler 83 below.

In variations, the second applicator portion 81 can be composed of a polymeric material (e.g., plastic), a metallic material, and/or any other suitable material. In variations of the applicator system 180 incorporating mechanical mechanisms, the second applicator portion 81 can be at least partially composed of plastic. In variations of the applicator system 180 incorporating magnetic and/or electromagnetic mechanisms, the second applicator portion 81 can be at least partially composed of a metal (e.g., steel, etc.). However, any applicator portion can additionally or alternatively be composed of any other suitable material.

1.3.3 Applicator—Support Elements and Other Elements

The applicator system 180 can also include an elastic coupler 83 between the first applicator portion 81 and the second applicator portion 82, wherein the elastic coupler 83 functions to store potential energy in the loaded mode of the trigger, which can be released to accelerate the first housing portion 81, with the microsensor patch 110, toward the body of the user. In variations wherein the first applicator portion 81 is situated within the second applicator portion 82, the elastic coupler 83 can be positioned such that translation of the first applicator portion 81 within the second applicator portion 82 adjusts a state of compression of the elastic coupler, thereby transitioning between a state of high potential energy in the loaded mode and a state of low potentially in the released mode, as described below. In a specific example, as shown in FIGS. 15, 16A, and 16B, the elastic coupler 83 can reside within a space laterally between a venting channel 86 of the first applicator portion 81 and an interior wall of the second housing portion, wherein the elastic coupler 83 is retained in position at either a base surface of the venting channel 86 of the first applicator portion 81 or a base surface of the second applicator portion 82; however, the elastic coupler 83 can additionally or alternatively be configured relative to the first applicator portion 81 and the second applicator portion 82 in any other suitable manner.

The elastic coupler 83 can include a spring with a suitable spring force in relation to storage of a maximum amount of potential energy to provide proper acceleration of the microsensor patch 110 toward the body of the user. Additionally or alternatively, the elastic coupler 83 can comprise any other suitable material that can transition between a state of high potential energy and low potential energy. In other variations, the elastic coupler 83 can include a pair of magnets with like polarity oriented toward each other, an elastomeric element, or any other suitable component that stores and releases potential energy.

As indicated above, in some variations wherein the second applicator portion 82 includes or is coupled to a magnet, the applicator system 180 can further include a coil of conductive material that passes current in a manner that causes an interaction between a magnetic field formed by the current and the magnet. In a specific example, as shown in FIGS. 17A and 17B, the elastic coupler 83 can be replaced or in some manner supplemented by a coil of wire (e.g., voice coil) coupled to a current source and operable to pass a desired amount of current, thereby affecting acceleration parameters (e.g., a velocity profile) of the first applicator portion 81, with the microsensor patch 110, toward the body of the user. As such, the second applicator portion can be operable between different modes, each mode associated with a different amount of current passage, wherein the current magnitude changes acceleration parameters of the first applicator portion 81, with the microsensor patch 110, toward the body of the user.

In still other variations, however, the elastic coupler 83 can additionally or alternatively include or replaced with any other suitable element that promotes an acceleration of the first applicator portion 81, with the microsensor patch 110, toward the body of the user. In one alternative example, the first applicator portion can be pneumatically driven using compressed air; however, any other suitable mechanism can be incorporated.

As indicated above, in some variations, the applicator system 180 can include a trigger 84 operable between a loaded mode 84*a* and a released mode 84*b*, wherein the trigger 84 functions to enable release of the first applicator portion 81 to accelerate the microsensor patch 110 toward the body of the user. The trigger 84 can be mechanically controlled or electrically controlled. For instance, in a first variation, the trigger 84 can be entirely mechanical and used to transition the retainer 821 of the second applicator portion 82 into a configuration that unlatches the first applicator portion 81 from the second applicator portion 82, allowing the compressed elastic coupler 83 to be released and accelerate the first applicator portion 81, with the microsensor patch 110, toward the user. In a second variation, the trigger 84 can be electronic and, when activated, allow current to pass through a conductive coil about a magnet of the second applicator portion 82, thereby generating a magnetic field that interacts with the magnet and creating a driving force to accelerate the first applicator portion 81, with the microsensor patch 110, toward the user. However, other variations of the trigger 84 can be configured in any other suitable manner, some examples of which are described in Sections 1.3.4 and 1.3.5 below.

The applicator system 180 can additionally or alternatively include any other suitable support elements. For instance, the applicator system 180 can include components that support the microsensor patch 110 and/or the applicator system 180 against the skin of the user prior to coupling of the microsensor to the user. In one variation, the applicator system 180 can include a compressible support material situated behind the coupling interface/suction interface of the first applicator portion 81, wherein the compressible support material complies with the user's body during the process of coupling the microsensor patch 110 to the user's body. The applicator system 180 can additionally or alternatively include structures that obscure the microsensor patch 110 from the user's view during the insertion process, in order to prevent apprehension of the user during the insertion process. Additionally or alternatively the applicator system 180 can include noise-dampening elements operable to prevent apprehension of the user during the insertion process. Additionally or alternatively, the applicator system 180 can include an audio detection element (e.g., a microphone coupled to an element of the applicator system) operable to detect a sound output from the elastic coupler 83 during a transition from the loaded mode to the released mode, thereby facilitating assessment of proper The system can, however, include any other suitable element(s).

1.3.4 Applicator—Specific Examples

In a first specific example, as shown in FIGS. 16A and 16B, the applicator system 180' includes a first applicator portion 81' including a suction interface 811' coupled to a venting channel 86' with an opening 87'; a second applicator portion 82' including a retainer; a spring 83' between the first applicator portion 81' and the second applicator portion 82'; and a trigger 84' including a sealing interface 88', the trigger 84' operable between a loaded mode 84*a*' and a released mode 84*b*'; wherein, in the loaded mode, as shown in FIG. 16A, the elastic coupler is in a first compressed state between the first applicator portion and the second applicator portion, the first applicator portion is retained by the retainer of the second applicator portion, and the suction interface is coupled to the second housing portion with the opening of the venting channel sealed by the sealing interface. As shown in FIG. 16A, transitioning to the loaded mode 84*a*' can be facilitated using an example of the base station 5 described in section 1.4 and shown in FIGS. 1 and 16A, wherein the base station 5 includes a recessed platform for receiving and positioning the first housing portion 191 within a substantially horizontal plane. In this example, the recessed platform includes a central opening into a cavity, wherein the cavity provides clearance for portions of the microsensor 116 coupled to the first housing portion 191, and wherein the cavity includes a charging slot that can accept units of the second housing portion 196 for charging (e.g., even when the first housing portion 191 is positioned at the recessed platform). As such, the base station 5 can include a charging station within the cavity and a platform, such that the base station 5 facilitates loading of a patch assembly and charging of a battery of the second housing portion. Then, as shown in FIG. 16A, pressing the second applicator portion 82' downward can transition the applicator 180' to the loaded mode 84*a*' by way of a trigger ring 2 of the second applicator portion 82' that translates upon being compressed by a recessed ring in the base station 5 that is concentric with the trigger ring 2.

After the applicator 180' is in the loaded mode 84*a*', it can then be transitioned to the released mode 84*b*', wherein, in the released mode, as shown in FIG. 16B, the spring 83' is in a second compressed state (e.g., a state of low compression) between the first applicator portion 81' and the second applicator portion 82', the first applicator portion is released from the retainer 821' of the second applicator portion, the suction interface 811' is released from the second housing portion with the opening 87' of the venting channel 86' unsealed by the sealing interface 88', and microsensor portions of the body chemistry monitor are coupled to the user. In the specific example, pressing the second applicator portion 82' downward against the user's skin can transition the applicator 180' to the released mode 84*b*' by way of the trigger ring 2 of the second applicator portion 82' that translates upon being compressed against the user's skin. In variations of this specific example, the trigger ring can have an adjustable set position that affects a travel distance between the loaded patch assembly and skin of the user, such that the acceleration profile of the applicator 180' can be adjusted depending on specific needs of the user. However, the trigger ring can alternatively be adjusted in any other suitable manner. In the specific example, the velocity of the microsensor 16 upon impact can be between 3 and 15 m/s; however, the velocity can alternatively be any other suitable velocity to provide coupling between the microsensor 116 and skin of the user.

In a broader use case for the applicator system 180' described above, the microsensor patch 110 can be loaded into the applicator system 180 with the second housing portion 196 coupled to a suction interface of the first housing portion, wherein in the loaded mode the venting channel 86 is sealed by a sealing interface of the second applicator portion 82/trigger 84. An adhesive portion of the first housing portion 191 can then be exposed, and the applicator system 180 can be positioned, in the loaded mode 84*a* and with the microsensor exposed and facing the body of the user. Then, the trigger 84 can be activated to transition the applicator system 180 to the released mode 84, thereby using converted potential energy from the compressed spring of the loaded mode 84*a* to accelerate portions of the microsensor into the body of the user. However, variations of the use case described above can be configured in any other suitable manner.

In a second specific example, as shown in FIGS. 17A and 17B, the applicator system 180" includes a first applicator portion 81" including a coupling interface 811" that couples to the microsensor patch by suction; a second applicator portion 82" composed of steel and including a magnet 89"; a spring 83" between the first applicator portion 81" and the second applicator portion 82"; a coil 88" operable to pass current and interact with the magnet 89"; and a trigger 84" operable between a loaded mode 84a" and a released mode 84b"; wherein, in the loaded mode, as shown in FIG. 17A, the elastic coupler is in a first compressed state between the first applicator portion and the second applicator portion, the first applicator portion is retained by the retainer of the second applicator portion, and the coupling interface is coupled to the microsensor patch; and wherein in the released mode, as shown in FIG. 17B, the spring 83" is in a second compressed state (e.g., a state of low compression) between the first applicator portion 81" and the second applicator portion 82", the first applicator portion is released from the retainer 821' of the second applicator portion with passage of current through the coil 88", the coupling interface 81" is released from the second housing portion 82", and microsensor portions of the body chemistry monitor are accelerated into to the user.

In a use case for the applicator system 180" described above, the microsensor patch 110 can be loaded into the applicator system 180" with the second housing portion 196 coupled to the coupling interface of the first housing portion. An adhesive portion of the first housing portion 191 can then be exposed, and the applicator system 180" can be positioned, in the loaded mode 84a and with the microsensor exposed and facing the body of the user. Then, the trigger 84 can be activated to transition the applicator system 180 to the released mode 84 with passage of current through the coil 88", thereby using electromagnetic interactions between the magnet 89" and the coil 88 to accelerate portions of the microsensor into the body of the user. However, variations of the use case described above can be configured in any other suitable manner However, variations of the specific examples and/or use cases described above can be configured in any other suitable manner. For instance, some variations of the applicator system 180 can include speaker components (or other components) operable to generate audible signals (or other signals, such as light signals, haptic signals, etc.) indicative of correct or incorrect application of the microsensor at the user's body.

1.3.5 Applicator—Other Variations

Figure 18A:
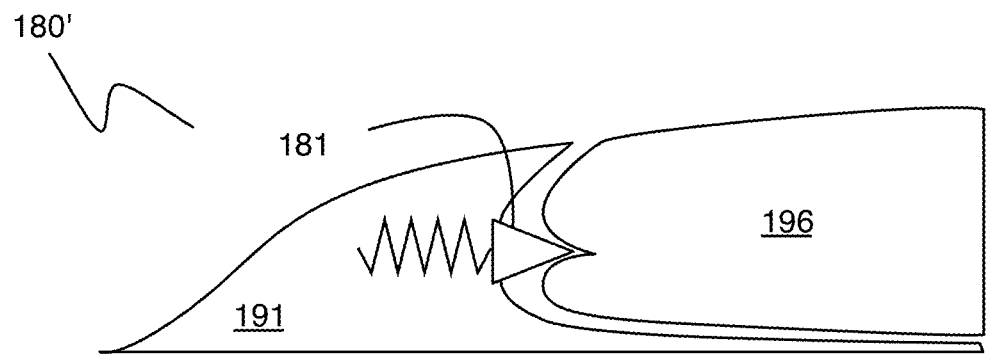
FIGS. 18A-18B depict variations of a applicator system in an embodiment of a system for monitoring body chemistry.

In another variation, as shown in FIG. 18A, the applicator system 180' can be incorporated into a first housing portion 191 of a housing 190 of the system 100 and can comprise an elastic pin 181 (e.g., spring-loaded pin) configured to complement a recess of a second housing portion 196. In this variation, a normal force applied to a broad surface of the second housing portion 196 initially causes the elastic pin 181 to retract, and rebounding of the elastic pin 181 into the recess of the second housing portion 196 biases and accelerates the microsensor 116 into the skin of the user.

Figure 18B:
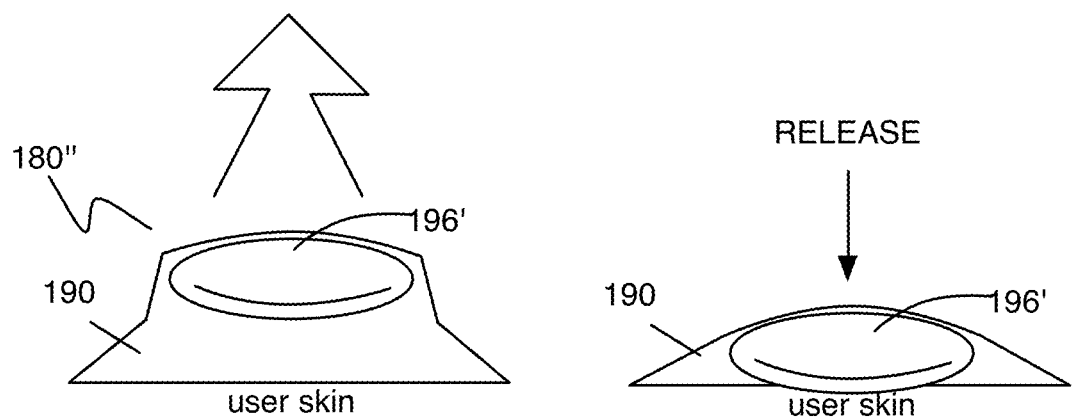

In another variation, as shown in FIG. 18B, the applicator system 180" implements elastic portions of the housing 190, which can be used to retract a housing portion with the microsensor 116 and to release the housing portion, thereby accelerating the microsensor 116 into skin of the user.

Figure 19A:
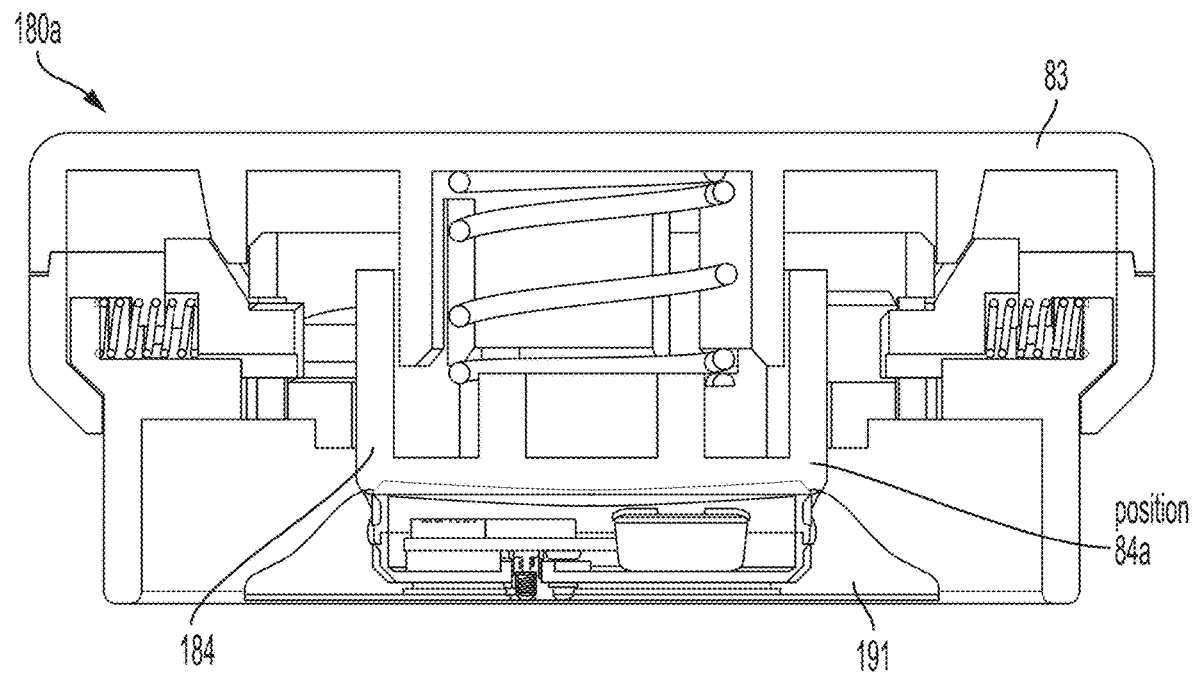
Figure 19B:
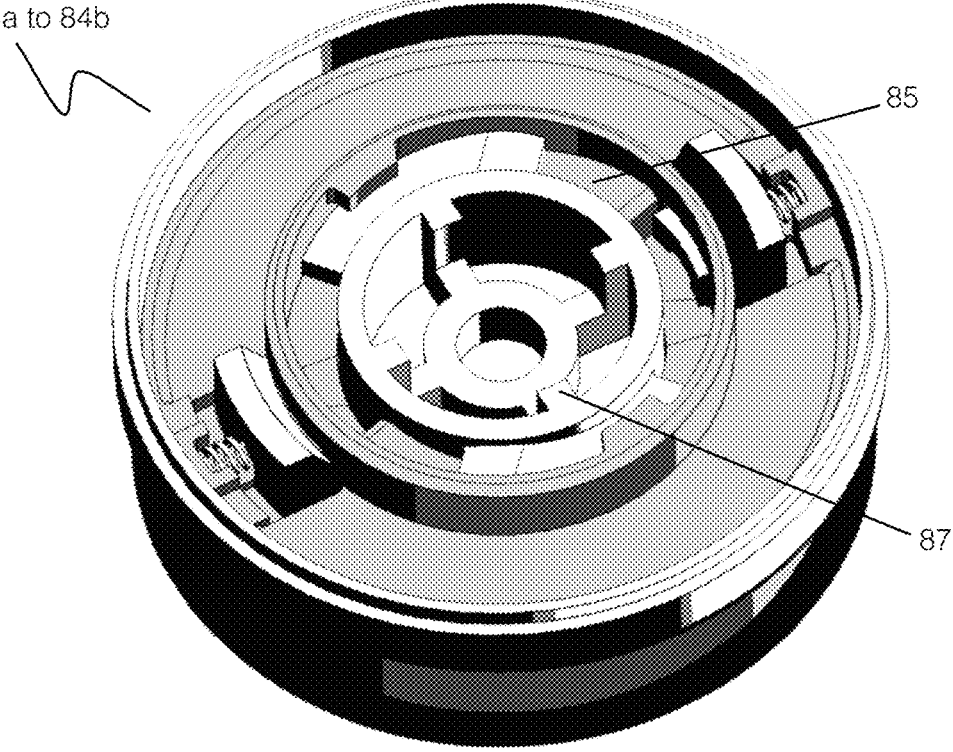

In another variation, the applicator system cooperates with a first housing portion 191 and a second housing portion 196, wherein the applicator system comprises a first applicator portion configured to surround the housing 190 and interface with the second housing portion 196, and a second applicator portion configured to accelerate the second housing portion toward skin of the user. In a first specific example of this variation, as shown in FIG. 19A, the applicator system 180a comprises a ram-and-catch mechanism, wherein twisting of a rotatable component 83 of the applicator system 180a transitions a plunger 184 of the applicator system 180a from a resting configuration 84a to a loaded configuration 84b, as shown in FIGS. 19B and 19C, and pushing of the rotatable component 83 of the applicator system 180a releases the plunger 184 back to the resting configuration 84a (as shown in FIG. 19D), thereby accelerating the microsensor 116 toward skin of the user during application of the microsensor patch 110 to the user. In more detail, in the first specific example, twisting of the rotatable component 83 transitions the plunger 184 along ramped surfaces 85 of the applicator system 180a to the loaded configuration 84a, where the plunger 184 rests on triggers 86 of the applicator system 180a. Then, as shown in FIG. 19D, pressing of the rotatable component 83 provides an outward biasing force on the triggers 86 (e.g., due to wedge-shaped morphology of the triggers that interacts with a complementary portion of the rotatable component 83), thereby releasing the plunger 184 to the resting configuration 84a. In this specific example, a set of ribs 87 coupled to a wall of the applicator system 180 surrounding the plunger 184 maintain plunger alignment.

Figure 20:
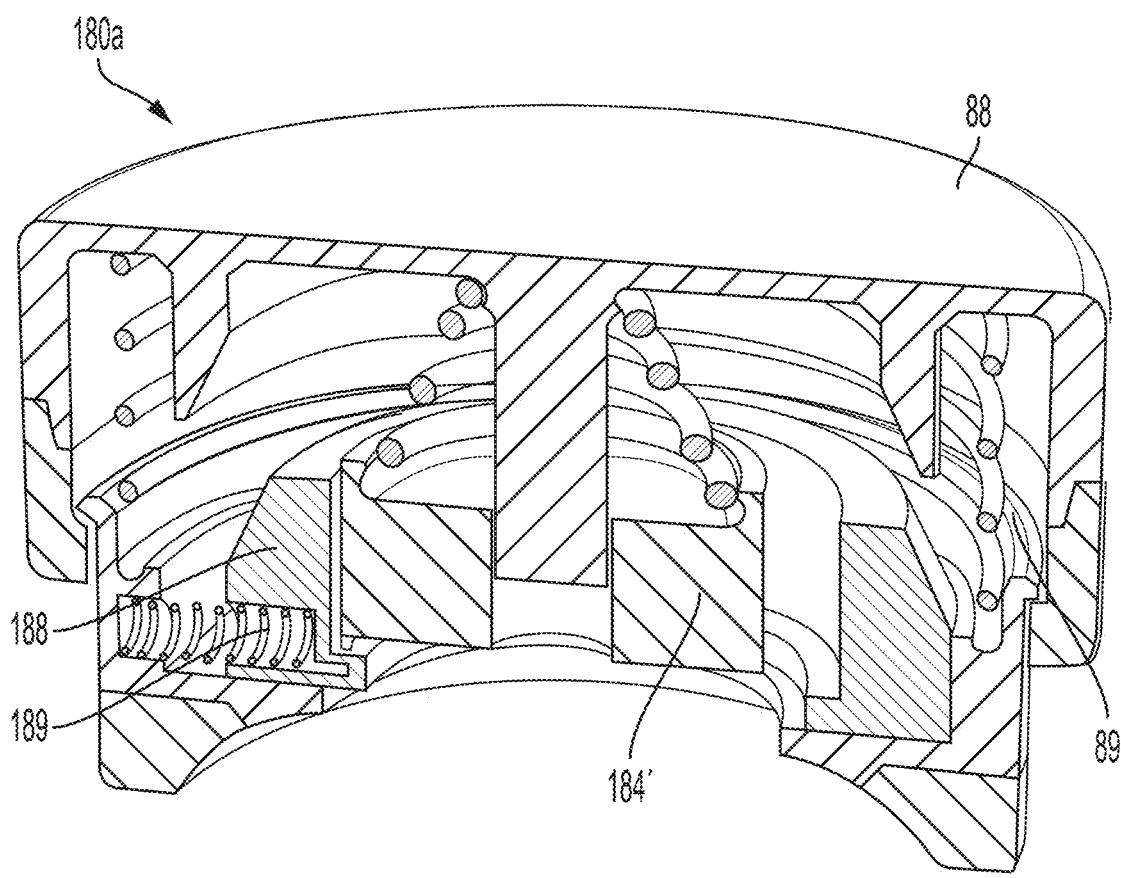
FIG. 20 depicts a second specific example of a applicator system in an embodiment of a system for monitoring body chemistry.

In a second specific example of this variation, as shown in FIG. 20, the applicator system 180b comprises an elastic component 89 housed within and coupled to a translating component 88 of the applicator system 180b, wherein the translating component 88 comprises a plunger 184' and is configured to translate along a first axis. The applicator system 180b further comprises a trigger 188 coupled to a biasing spring 189 and configured to translate along a second axis perpendicular to the first axis, between a holding position 188a and a releasing position 188b. In the second specific example, the translating component 88 is biased in holding position 188a, and pushing of the translating component 88 places a lateral biasing force on the trigger 188 against the biasing spring 189 (e.g., due to wedge-shaped morphology of the trigger 188 that interacts with a complementary portion of the translating component 88), thereby releasing the plunger 184' to accelerate the microsensor 116 toward skin of the user. In pushing the translating component 88, compression of the elastic component 89 creates a reverse biasing force that automatically releases the translating component 88 toward the resting configuration 88a.

The applicator system 180 can alternatively be configured to receive the microsensor patch 110, to stretch the skin of the user isotropically in two dimensions to facilitate application, and to push the microsensor patch 110/transmitting unit 130 assembly onto the user's stretch skin. Still alternatively, the applicator system 180 can include any other suitable applicator, variations and examples of which are described in U.S. App. No. 62/025,174 entitled "System for Monitoring Body Chemistry" and filed on 16 Jul. 2014. Still other variations of the system 100 can entirely omit a applicator system 180.

1.4 System—Base Station

Figure 21A:
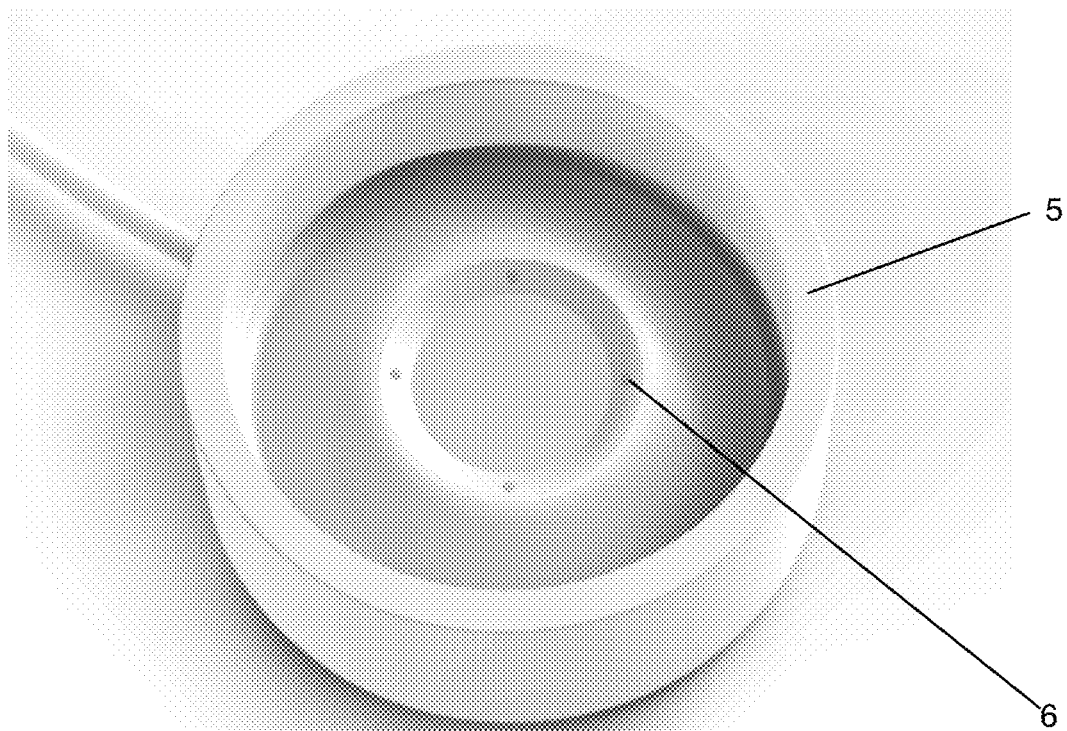
FIGS. 21A-21B depict a specific example of a base station in an embodiment of a system for monitoring body chemistry.
Figure 21B:
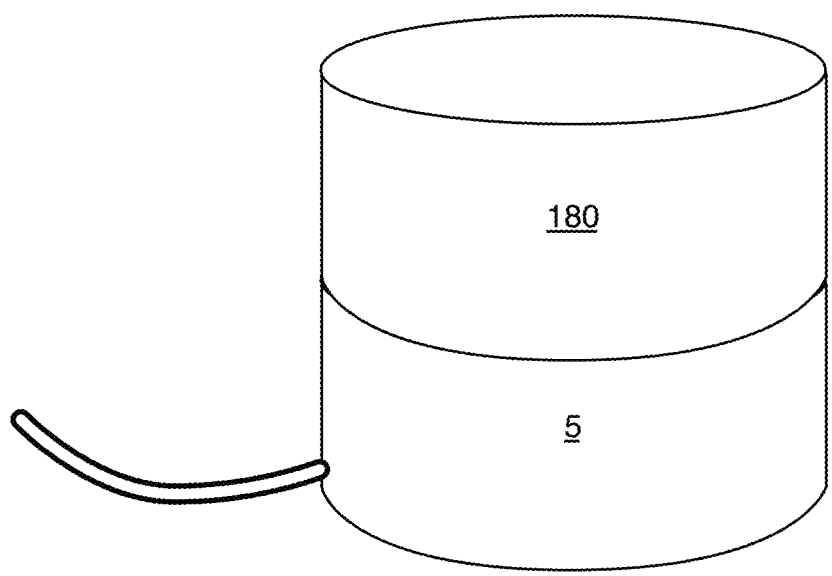

As shown in FIG. 1, the system can include a base station 5 that functions to receive the microsensor patch 110 (e.g., within a second housing portion 196). In receiving the microsensor patch 110, the base station 5 can include alignment elements 6 (e.g., protrusions, recesses, magnetic alignment elements, etc.) that facilitate alignment of the microsensor patch 110 within the base station, as shown in FIG. 18A. The base station 5 can additionally or alternatively facilitate charging of a rechargeable battery of the microsensor patch 110 by including elements that generate an electromagnetic field that interacts with a charging coil coupled to the battery, thereby charging the battery 138. In more detail, as described above, the base station 5 can include a cavity with a slot that accepts the second housing portion 196 (or any other portion of the system 100 containing the battery) for charging, where by contacts of the charging unit can detect a feedback loop between the an analog front end (AFE) circuit of the second housing portion 196 and charging contacts, in order to initiate charging. The base station 5 can additionally or alternatively be used to transition the microsensor patch between different operational states, in relation to data transfer between the microsensor patch 110, a mobile computing device 150 associated with the user, and modules of a processing subsystem 160 (e.g., cloud module) as shown in FIGS. 21A and 21B. In a first operation mode Sa, the transmitting unit 130 of the microsensor patch 110 and the mobile computing device 150 can pair/bond only when the second housing portion 196 of the microsensor patch 110 is in communication with the base station 5 (e.g., aligned within the base station 5). Thus, in the first operation mode 5a, the microsensor patch 110 can transmit and receive data (e.g., compact raw data compounded into a plurality of bits over Bluetooth communication). In a second operation mode 5b wherein the microsensor patch 110 is not in communication with the base station 5, the microsensor patch 110 can be configured to only transmit data (but not receive data), thereby reducing energy usage, preventing man-in-the-middle attack, and preventing tampering. As such, the second operation mode 5b prevents reading of data from the microsensor patch 110 by a fraudulent entity, without gaining physical access to the microsensor patch 110.

Figure 22:
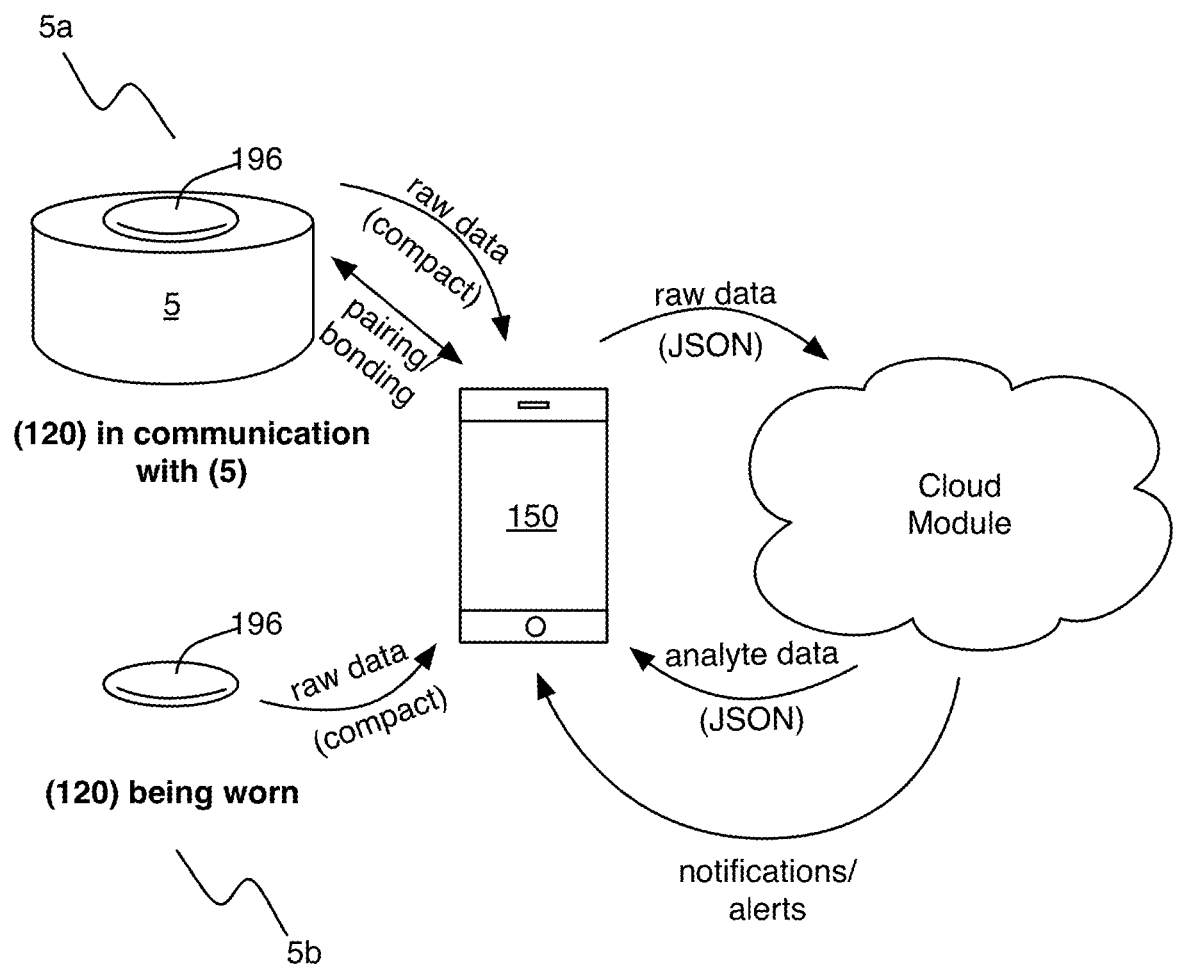
FIG. 22 depicts operation modes of components of an embodiment of a system for monitoring body chemistry.

The operation modes of the system 100 enabled by the microsensor patch, the base station 5, the mobile computing device 150, and the processing subsystem 160 are further detailed in FIGS. 21A and 21B and 22. In relation to pairing with the microsensor patch 110 in the first operation mode Sa, the mobile computing device 150 functions to provide one or more of: data relay, data visualization, data storage, notification, and action functions (e.g., as described in relation to the software module 163 described above). In communicating information between the mobile computing device 150 and a cloud module of the processing subsystem 160, the mobile computing device 150 can be configured to transmit raw data in Javascript Object Notation (JSON) format (or any other suitable format) to be processed in the cloud, and analyte data, notifications, and alerts (e.g., as derived from an analysis) can be transmitted back to the mobile computing device 150 in JSON format (or any other suitable format). The cloud module of the processing subsystem 160 can thus serve to enable authentication of the user (e.g., in association with a user account of a native application) and/or data, data storage, data processing, notification, and prediction functions, as described in relation to the processing subsystem 160 described above. Thus, the system 100 is configured for fault tolerance, wherein the microsensor patch 110 stores data when faulty operation of the mobile computing device 150 occurs, and failure of the processing subsystem 100 results in data storage at the mobile computing device. The system 100 can, however, be configured in any other suitable manner.

As shown in FIG. 21B, the base station 5 and the applicator system 180 can be configured to couple together, thus facilitating portability of the base station 5 and applicator system 180. However, the base station 5, applicator system 180, and microsensor 110 can alternatively be configured to couple or not couple together in any other suitable manner.

1.5 System—Calibration

The microsensor patch 110 is preferably calibrated to prevent signal degradation and to mitigate the effects of transient effects experienced during analyte sensing. The primary sensing mechanism is potentiometric for small analytes (e.g., potassium, sodium, calcium), and amperometric for large molecules (e.g., glucose, lactic, creatinine). In a first variation, the microsensor patch 110 passively detects analytes by detecting an impedance and/or capacitance change, as well as a voltage change when an analyte or analyte concentration contacts the microsensor 116. Calibration can occur by normalizing sensing measurements relative to a grounded portion of the microsensor 116, such as a reference electrode.

In a second variation, the microsensor patch 110 can implement active impedance calibration, wherein a drive voltage is implemented by the electronics subsystem in of the microsensor patch 110, and voltage and impedance and/or capacitance changes are detected. The drive voltage is preferably applied in a sinusoidal pattern, but can alternatively be applied in any appropriate pattern. In the second variation, sensed analytes or analyte concentrations are characterized by changes in impedance, and noise is characteristically distinguished from analyte detection by monitoring changes in voltage unaccompanied by changes in impedance or capacitance. The second variation thus employs a conductometric measurement to calibrate the microsensor patch 110. Impedance measurements can also be used to address shift in a reference electrode (e.g., in the first variation described above).

In a third variation, the microsensor patch 110 can employ injection of a volume of a calibration solution with a known concentration of at least one analyte, in order to calibrate the microsensor patch 110. In an example of the third variation, the calibration solution can have a known concentration of at least one analyte, such that changes (e.g., changes in electrical parameters) detected by the microsensor patch 110 in response to the calibration solution can be used to normalize measurements resulting from sensed analytes or analyte concentrations occurring after injection of the volume of calibration solution. In the third variation, the calibration solution can be injected automatically and periodically over the lifetime usage of the transdermal patch; however, the calibration solution can alternatively be injected when prompted by a user or other entity.

In a fourth variation, the microsensor patch 110 can include a membrane comprising a known concentration and/or release profile of at least one analyte, in order to calibrate the microsensor patch 110. In an example of the fourth variation, the membrane can have a known concentration and release profile of at least one analyte, such that changes (e.g., changes in electrical parameters) detected by the microsensor patch 110 in response to the membrane can be used to normalize measurements resulting from sensed analytes or analyte concentrations. In the fourth variation, the membrane can be a degradable membrane, such that degradation of the membrane over time releases analytes from the membrane. Alternatively, the membrane can be manufactured with specific porosity, contributing to a certain analyte release profile.

In a fifth variation, the microsensor patch 110 can include a coating or a cap comprising a soluble species (e.g., analyte/ion) with a well-known solubility, in order to calibrate the microsensor patch 110. In an example of the fifth variation, the soluble species maintains a known concentration of the species within the vicinity of a filament that can be used to normalize and/or calibrate a signal. Examples of soluble species include low solubility, biocompatible calcium salts, such as calcium carbonate, calcium phosphate, and dicalcium phosphate for calcium sensing. Other suitable soluble species can be used to calibrate other analytes.

In alternative variations, the microsensor patch 110 can use any other suitable calibration method. For instance, the transdermal patch can be pre-staged, prepped, loaded, or activated to have a set calibration state enabling calibration of the system after application to the user within a desired period of time (e.g., an 85 mg/dl calibration state equilibrated after insertion within a period of 2 hours).

As a person skilled in the art will recognize from the previous detailed description and from the figures and claims, modifications and changes can be made to the described embodiments, variations, and examples of the system 100 without departing from the scope of the system 100.

2. Method

As shown in FIG. 23, a method 200 for monitoring body chemistry of a user comprises: receiving a second housing portion into an opening of a first housing portion S210, the first housing portion supporting a microsensor including a first working electrode, a second working electrode, a reference electrode, and a counter electrode, and the second housing portion supporting an electronics subsystem configured to receive a signal stream from the microsensor; after interfacing with the second housing portion, accelerating the second housing portion toward skin of the user S220, thereby delivering sensing regions of the microsensor into interstitial fluid of the user; generating an impedance signal, from two of the first working electrode, the second working electrode, the reference electrode, and the counter electrode, in response to applying a voltage, near a shifted potential different than a reference potential of the reference electrode S230, wherein the shifted potential is associated with a signal conditioning module of the electronics subsystem; at a processing system in communication with the electronics subsystem, receiving the signal stream and the impedance signal S240; at the processing system, generating an analysis indicative of an analyte parameter of the user and derived from the signal stream and the impedance signal S250; and transmitting information derived from the analysis to an electronic device associated with the user, thereby facilitating monitoring of body chemistry of the user S260.

The method 200 functions to provide continuous monitoring of a user's body chemistry through reception and processing of signals associated with of one or more analytes present in the body of the user, and to provide an analysis of the user's body chemistry to the user and/or an entity (e.g., health care professional, caretaker, relative, friend, acquaintance, etc.) associated with the user. Alternatively, the method 200 can function to detect a user's body chemistry upon the user's request or sporadically, and/or can provide an analysis of the user's body chemistry only to the user. The method is preferably implemented, at least in part, using an embodiment, variation, or example of elements of the system 100 described in Section 1 above; however, the method 200 can additionally or alternatively be implemented using any other suitable system.

Variations of the system 100 and method 200 include any combination or permutation of the described components and processes. Furthermore, various processes of the preferred method can be embodied and/or implemented at least in part as a machine configured to receive a computer-readable medium storing computer-readable instructions and/or in the cloud. The instructions are preferably executed by computer-executable components preferably integrated with a system and one or more portions of a control module and/or a processor. The computer-readable medium can be stored on any suitable computer readable media such as RAMs, ROMs, flash memory, EEPROMs, optical devices (CD or DVD), hard drives, floppy drives, or any suitable device. The computer-executable component is preferably a general or application specific processor, but any suitable dedicated hardware device or hardware/firmware combination device can additionally or alternatively execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the preferred embodiments of the invention without departing from the scope of this invention defined in the following claims.

We claim:

1. A health monitoring system, comprising:
a reusable applicator having a loaded mode for holding a wearable microsensor patch and a release mode for applying the wearable microsensor patch to a user, the reusable applicator including:
an access opening;
a plunger including a coupling interface having
a suction element configured to sealingly contact and hold the wearable microsensor patch such that an adhesive substrate and microneedles of the wearable microsensor patch face the access opening, wherein the microneedles are configured to access interstitial fluid of the user and detect at least one analyte in the interstitial fluid in the user, and
a venting channel configured to facilitate release of the wearable microsensor patch from the suction element during and/or after acceleration of the wearable microsensor patch toward the user, and
a user-activated trigger mechanism configured to cause the plunger to push the wearable microsensor patch toward the access opening and to drive the microneedles into the user's skin when the reusable applicator transitions from the loaded mode to the release mode, wherein the suction element is configured to release the wearable microsensor patch while the adhesive substrate is adhered to the user's skin and the microneedles extend into the user's skin.

2. The health monitoring system of claim 1, further comprising the wearable microsensor patch including
a patch assembly having the adhesive substrate and the microneedles; and
a pod configured to be releasably coupled to the patch assembly to establish electrical communication with the patch assembly, wherein the pod includes:
a power supply, and
an electronics module in electrical communication with the power supply and programmed to automatically perform signal conditioning and analysis of one or more signals from the patch assembly generated by detection of the at least one analyte.

3. The health monitoring system of claim 1, wherein the suction element is configured to hold the wearable microsensor patch such that the microneedles are positioned directly between the user's skin and the plunger.

4. The health monitoring system of claim 1, wherein when the reusable applicator is positioned against the user's skin, the user-activated trigger mechanism is configured to apply the microsensor patch in response to the user pressing on a backside of the reusable applicator.

5. The health monitoring system of claim 1, wherein the user-activated trigger mechanism includes
a ram-and-catch mechanism configured to move the plunger, and
a depressable component configured to be pressed upon by the user to release the plunger such that the plunger moves the microsensor patch toward the access opening.

6. The health monitoring system of claim 5, wherein the depressable component rotates relative to a housing of the applicator to set a level of patch acceleration for applying the microsensor patch to the user.

7. The health monitoring system of claim 1, wherein the plunger includes a spring that is compressed when the reusable applicator is in the loaded mode, wherein the reusable applicator is transitionable to the release mode to allow the compressed spring to bias the microsensor patch toward the user's skin.

8. The health monitoring system of claim 1, further comprising an adjuster operable to set an acceleration profile for accelerating the microsensor patch toward the user's skin.

9. The health monitoring system of claim 1, wherein the reusable applicator is configured to move the microsensor patch at speed in a range of 3 m/sec to 15 m/sec at which the microsensor patch contacts the user's skin.

10. The health monitoring system of claim 1, wherein the suction element is configured to hold a backside of the wearable microsensor patch located opposite of the microneedles.

11. The health monitoring system of claim 1, wherein the plunger accelerates the wearable microsensor patch toward the user's skin to cause sensing regions of the microneedles to access the interstitial fluid.

12. The health monitoring system of claim 1, wherein the reusable applicator is configured to be held against the user's skin while inserting the microneedles into the user's skin.

13. The health monitoring system of claim 1, wherein the user-activated trigger mechanism is spring-loaded to bias the wearable microsensor patch toward the user's skin upon activation.

14. The health monitoring system of claim 1, wherein the reusable applicator includes
a lower housing surrounding the plunger; and
an upper housing coupled to the lower housing and upon which a user applies a compressive force to trigger the trigger mechanism.

15. The health monitoring system of claim 1, wherein the plunger is configured to be pressed against the wearable microsensor patch to retain the microsensor patch.

16. The health monitoring system of claim 1, wherein the applicator is configured to draw suction to hold the wearable microsensor patch.

17. The health monitoring system of claim 1, further comprising a base station configured to receive the reusable applicator and to charge a power source of the wearable microsensor patch.

18. A health monitoring system, comprising:
a wearable microsensor patch including:
an adhesive substrate, and
a pod including:
a power supply, and
an electronics module in electrical communication with the power supply and programmed to automatically perform signal conditioning and analysis of one or more signals generated by at least one sensing element when the adhesive substrate is coupled to a user's skin;
an applicator having a loaded mode for retaining the wearable microsensor patch and a release mode for automatically applying the wearable microsensor patch to the user, the reusable applicator including:
an opening,
an actuator including:
a plunger, and
a coil spring configured to cause the plunger to move along an axis toward the wearable microsensor patch, wherein the axis is generally perpendicular to the opening and surrounded by the coil spring, and
a trigger mechanism configured to cause the actuator to move the at least one sensing element into the user's skin when the reusable applicator transitions from the loaded mode to the release mode, wherein the applicator is configured to be separated from the wearable microsensor patch after the adhesive substrate is adhered to the user's epidermis and the at least one sensing element that extends into the user's tissue for detecting at least one analyte in interstitial fluid,
wherein the plunger includes a suction element and a venting channel in communication with the suction element, wherein the venting channel is configured to facilitate release of the wearable microsensor patch from the suction element.

19. The health monitoring system of claim 18, wherein the trigger mechanism includes
a ram-and-catch mechanism configured to move the actuator, and
a depressable component configured to be pressed upon by the user to release the actuator to move the actuator, thereby moving the microsensor patch toward the user's body.

20. The health monitoring system of claim 19, wherein the depressable component rotates relative to a housing of the applicator to set a level of microsensor patch acceleration for applying the microsensor patch.

21. A health monitoring system, comprising:
a reusable applicator having a loaded mode for retaining a wearable microsensor patch and a release mode for automatically applying the wearable microsensor patch to a user, the reusable applicator including:
an opening,
an actuator positioned to hold the wearable microsensor patch to face the opening, wherein the actuator includes a plunger including a coupling interface having a suction element and a venting channel configured to facilitate release of the wearable microsensor patch from the suction element during and/or after acceleration of the wearable microsensor patch toward the user; and
a trigger mechanism configured to cause the actuator to move microneedles of the wearable microsensor patch into the user when the reusable applicator transitions from the loaded mode to the release mode, wherein the actuator is configured to release the wearable microsensor patch after an adhesive substrate of the wearable microsensor patch is adhered to the user's skin and the microneedles extend into the user's tissue for detecting at least one analyte in interstitial fluid.

22. The health monitoring system of claim 21, wherein the reusable applicator is configured to create suction sufficient to hold the wearable microsensor patch.

23. The health monitoring system of claim 21, wherein when the reusable applicator is positioned against the user's skin, the trigger mechanism is configured to apply the microsensor patch in response to the user pressing on a backside of the reusable applicator.

24. The health monitoring system of claim 21, further comprising the comprising the wearable microsensor patch including:
a patch assembly having the adhesive substrate and the microneedles; and
a pod configured to be releasably coupled to the patch assembly to establish electrical communication with the patch assembly, wherein the pod includes an electronics module programmed to automatically analyze one or more signals from the patch assembly generated by detection of the at least one analyte.

25. The health monitoring system of claim 21, further comprising a base station configured to receive the reusable applicator and to charge a power source of the wearable microsensor patch held within the reusable applicator.

26. A health monitoring system, comprising:
an applicator having a loaded mode for holding a wearable analyte sensor patch and a release mode for applying the wearable analyte sensor patch to a user, the applicator including:
an access opening;
a plunger configured to grip the wearable analyte sensor patch such that an adhesive substrate of the wearable sensor patch faces the access opening and at least one needle is spaced apart from the access opening, wherein the at least one needle is configured to access fluid of the user to detect at least one analyte in the fluid, wherein the plunger includes a coupling interface with a suction element and a venting channel in communication with the suction element to facilitate release of the wearable microsensor patch from the coupling interface during and/or after acceleration of the wearable microsensor patch toward the user; and
a user-activated trigger mechanism configured to cause the plunger to push the wearable sensor patch toward the access opening to adhere the wearable sensor patch to the user's skin when the reusable applicator transitions from the loaded mode to the release mode, wherein the applicator is configured to release the wearable sensor patch while the adhesive substrate is adhered to the user's skin and the at least one needle is coupled to wearable sensor patch and extends into the user's skin.

27. The health monitoring system of claim 26, further comprising a coil spring that is compressed when the applicator is moved toward the loaded mode and holds the wearable sensor patch.

28. The health monitoring system of claim 26 wherein the plunger is configured to grip a housing of the wearable analyte sensor patch when the plunger is moved into contact with the housing.

29. The health monitoring system of claim 26, wherein the applicator further includes a cylindrical sidewall configured to surround the wearable analyte sensor patch to keep the wearable analyte sensor patch positioned with respect to the plunger.

30. The health monitoring system of claim 26, further comprising a base station configured to align the wearable analyte sensor patch with respect to the applicator, wherein the base station is further configured to be coupled to the applicator.

31. The health monitoring system of claim 26, wherein the applicator has a plurality of springs configured to sequentially drive components of the applicator so as to accelerate a housing of the wearable analyte sensor patch toward the user's skin in response to operation of the user-activated trigger mechanism.

32. The health monitoring system of claim 26, further comprising a filament with an analyte sensing region.

33. A health monitoring system, comprising:
an applicator having a loaded mode for holding a housing of a wearable analyte sensor patch inside the applicator and a release mode for applying the wearable analyte sensor patch to a user, the applicator including:
an opening,
a plunger with a suction element and a venting channel in communication with the suction element such that the wearable analyte sensor patch is released by the suction element during and/or after the applicator moves of the wearable microsensor patch toward the user,
at least one biasing element, and
a user-activated trigger mechanism configured to cause the at least one biasing element to move the plunger toward a housing of the wearable sensor patch to adhere the wearable sensor patch to the user's skin when the applicator, held against the user's skin, transitions from the loaded mode to the release mode, and wherein the applicator is configured to be separated from the wearable sensor patch while an adhesive substrate of the wearable sensor patch is adhered to the user's skin and a sensing element of the wearable analyte sensor patch extends into the user's tissue.

34. The health monitoring system of claim 33, further comprising a coil spring that is compressed when the applicator is moved toward the loaded mode to hold the housing directly between the plunger and the opening.

35. The health monitoring system of claim 33, wherein the plunger is configured to push against a periphery of a backside of the housing.

36. The health monitoring system of claim 33, wherein the applicator further includes a cylindrical sidewall configured to surround the wearable analyte sensor patch to keep the plunger positioned against the housing of the wearable analyte sensor, wherein electronics are positioned within the housing.

37. The health monitoring system of claim 33, wherein the applicator is configured to accelerate the at least one sensing element toward the user to position a sensing region of the at least one sensing element within the user's tissue to access interstitial fluid of the user.

38. The health monitoring system of claim 33, wherein the applicator has a plurality of springs configured to sequentially drive components of the applicator such that the a housing of the wearable analyte sensor patch is accelerated to toward the user's skin in response to operation of the user-activated trigger mechanism.

39. The health monitoring system of claim 33, wherein the sensing element is an analyte-sensing filament.

\* \* \* \* \*

UNITED STATES PATENT AND TRADEMARK OFFICE
CERTIFICATE OF CORRECTION

PATENT NO. : 11,172,851 B2
APPLICATION NO. : 17/182097
DATED : November 16, 2021
INVENTOR(S) : Ashwin Pushpala et al.

It is certified that error appears in the above-identified patent and that said Letters Patent is hereby corrected as shown below:

In the Drawings

On sheet 5 of 31, in Figure 4, reference numeral 38, Line 1, delete "Gage" and insert -- gauge --, therefor.

In the Specification

In Column 4, Line 33, delete "no" and insert -- 110 --.

In Column 4, Line 35, delete "no" and insert -- 110 --.

In Column 4, Line 38, delete "no" and insert -- 110 --.

In Column 4, Line 39, delete "no" and insert -- 110 --.

In Column 4, Line 41, delete "no" and insert -- 110 --.

In Column 4, Line 46, delete "no" and insert -- 110 --.

In Column 4, Line 48, delete "no" and insert -- 110 --.

In Column 4, Line 50, delete "no" and insert -- 110 --.

In Column 4, Line 53, delete "no" and insert -- 110 --.

In Column 11, Line 17, delete "gage" and insert -- gauge --.

In Column 15, Line 56, delete "10" and insert -- 110 --.

In Column 20, Line 62, delete "paralene," and insert -- parylene, --.

Signed and Sealed this
Thirty-first Day of January, 2023

Katherine Kelly Vidal
*Director of the United States Patent and Trademark Office*

CERTIFICATE OF CORRECTION (continued)
U.S. Pat. No. 11,172,851 B2

In Column 23, Line 9, delete "heath-related" and insert -- health-related --.

In Column 25, Line 24, delete "the a" and insert -- a --.

In Column 29, Line 50, after "proper" insert -- . --.

In Column 30, Line 47, delete "16" and insert -- 116 --.

In Column 31, Line 22, delete "81"" and insert -- 811" --.

In Column 31, Line 39, after "manner" insert -- . --.

In Column 33, Line 10, delete "the an" and insert -- an --.

In Column 33, Line 19, delete "Sa," and insert -- 5a, --.

In Column 33, Line 41, delete "Sa," and insert -- 5a, --.

In Column 34, Line 21, delete "in" and insert -- 111 --.

In the Claims

In Column 39, Line 35, in Claim 24, delete "comprising the comprising the" and insert -- comprising the --.

In Column 41, Line 17, in Claim 38, delete "the a" and insert -- the --.